US008652030B2

(12) United States Patent
Matsuura et al.

(10) Patent No.: US 8,652,030 B2
(45) Date of Patent: Feb. 18, 2014

(54) TWO-PART BENDING ENDOSCOPE

(75) Inventors: Wataru Matsuura, Fuchu (JP);
Yasuhito Kura, Hachioji (JP); Kazuki Honda, Higashiyamato (JP)

(73) Assignee: Olympus Medical Systems Corp., Tokyo (JP)

( * ) Notice: Subject to any disclaimer, the term of this patent is extended or adjusted under 35 U.S.C. 154(b) by 101 days.

(21) Appl. No.: 13/286,906

(22) Filed: Nov. 1, 2011

(65) Prior Publication Data

US 2012/0116166 A1    May 10, 2012

Related U.S. Application Data

(63) Continuation of application No. PCT/JP2011/061522, filed on May 19, 2011.

(30) Foreign Application Priority Data

May 21, 2010   (JP) ................................ 2010-117636

(51) Int. Cl.
*A61B 1/00* (2006.01)

(52) U.S. Cl.
USPC ........................................ 600/146; 600/139

(58) Field of Classification Search
USPC ................. 600/115, 116, 139, 141, 145–148; 604/528
See application file for complete search history.

(56) References Cited

U.S. PATENT DOCUMENTS

| 5,860,953 | A | 1/1999 | Snoke et al. |
| 6,074,343 | A | 6/2000 | Nathanson et al. |
| 6,638,213 | B2 * | 10/2003 | Ogura et al. ................. 600/148 |
| 6,749,560 | B1 | 6/2004 | Konstorum et al. |
| 2003/0023142 | A1 | 1/2003 | Grabover et al. |
| 2006/0252993 | A1 | 11/2006 | Freed et al. |
| 2007/0287887 | A1 * | 12/2007 | Maruyama ................. 600/147 |

FOREIGN PATENT DOCUMENTS

| EP | 1929932 A1 | 12/2006 |
| JP | A-62-047333 | 3/1987 |
| JP | A-06-114000 | 4/1994 |
| JP | A-2000-126118 | 5/2000 |

(Continued)

OTHER PUBLICATIONS

Dec. 3, 2012 Search Report issued in European Application No. 11783615.5.

(Continued)

*Primary Examiner* — Alireza Nia
*Assistant Examiner* — Timothy J Neal
(74) *Attorney, Agent, or Firm* — Oliff PLC

(57) ABSTRACT

A two-part bending endoscope includes: a first bending part which configures one side of a bending portion; a second bending part which configures the other end side of the bending portion; and a bending portion operation apparatus including a first operation device for causing the first bending part to perform a bending action and a second operation device for causing the second bending part to perform a bending action, wherein the bending portion operation apparatus includes a selective power-transmitting mechanism section which enables at least a bending action of the first bending part by the first operation device, and an interlocking operation of the second bending part and the first bending part by the second operation device.

8 Claims, 39 Drawing Sheets

(56) References Cited

FOREIGN PATENT DOCUMENTS

| | | |
|---|---|---|
| JP | A-2000-229061 | 8/2000 |
| JP | A-2001-161631 | 6/2001 |
| JP | A-2003-220022 | 8/2003 |
| JP | A-2003-250762 | 9/2003 |
| JP | A-2006-112524 | 4/2006 |
| JP | A-2007-196017 | 8/2007 |
| JP | A-2009-160211 | 7/2009 |

OTHER PUBLICATIONS

Watanabe, "Development of Interactive Clutch Lock Type," *Origin Technical Journal,* 2007, No. 70, pp. 12-17 (with English-language Abstract).

International Search Report in International Application No. PCT/JP2011/061522; dated Jun. 28, 2011 (with English-language translation).

\* cited by examiner

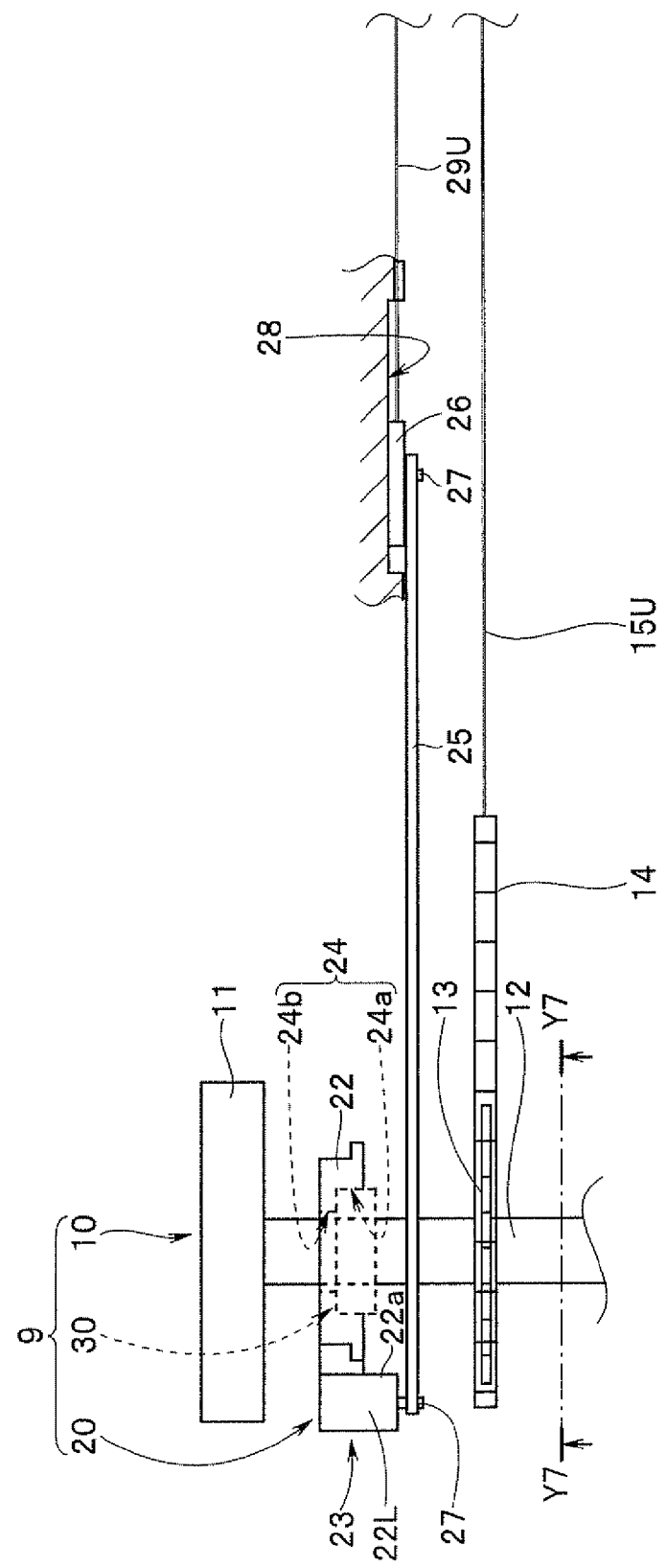

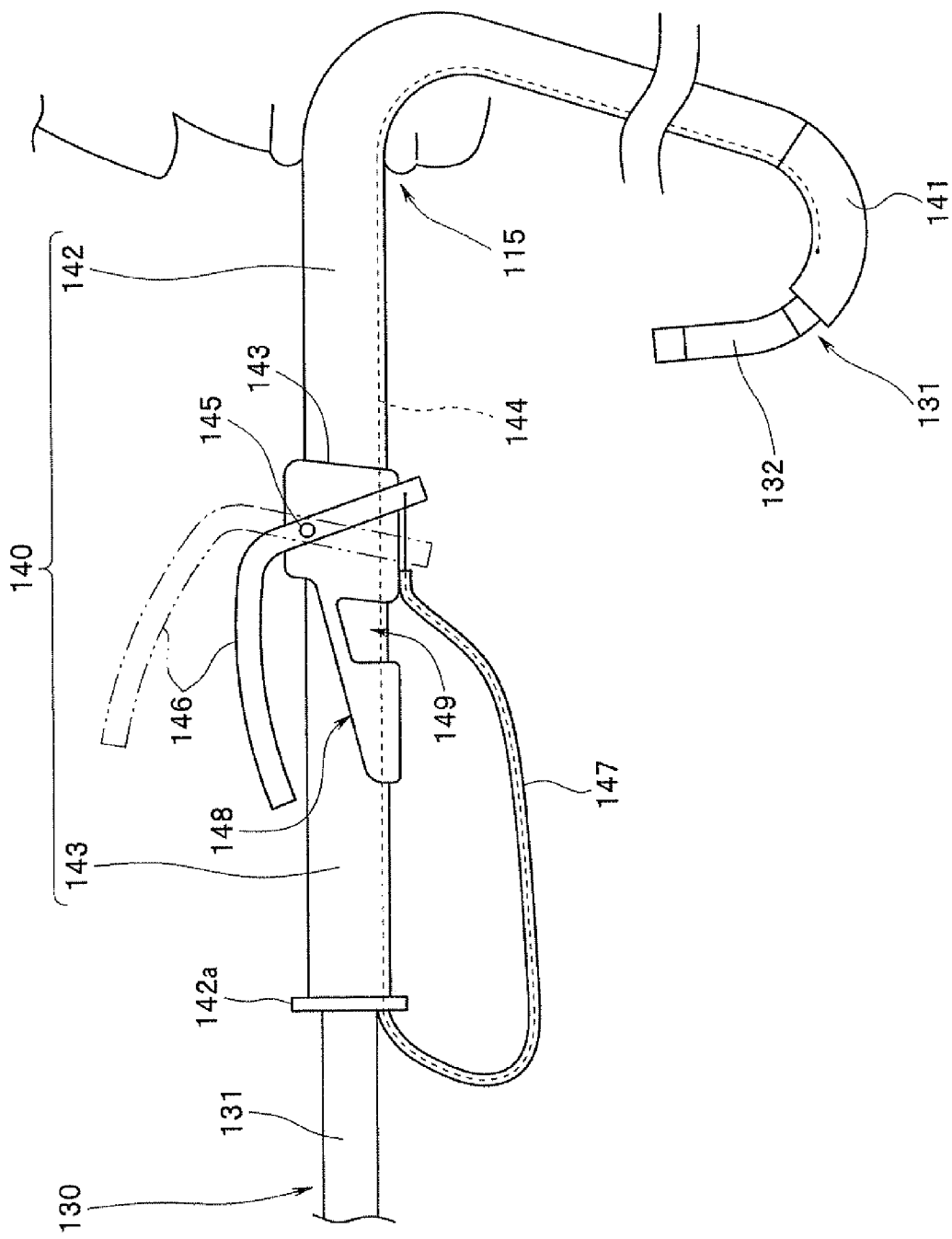

TWO-PART BENDING ENDOSCOPE

CROSS REFERENCE TO RELATED APPLICATION

This application is a continuation application of PCT/JP2011/061522 filed on May 19, 2011 and claims benefit of Japanese Application No. 2010-117636 filed in Japan on May 21, 2010, the entire contents of which are incorporated herein by this reference.

BACKGROUND OF THE INVENTION

1. Field of the Invention

The present invention relates to a two-part bending endoscope including in an insertion portion of the endoscope a bending portion configured by including a first bending part and a second bending part.

2. Description of the Related Art

An endoscope has an elongated insertion portion configured to be inserted into a body. The insertion portion is inserted into a lumen such as a stomach, intestines, or the like. A lumen has a sterically and intricately curved shape. Therefore, when the insertion portion is inserted into a deep part inside the sterically curved lumen, it is necessary to sterically curve the insertion portion in accordance with the luminal shape.

Japanese Patent Application Laid-Open Publication No. 2003-220022 (hereinafter, referred to as a patent document) discloses an endoscope with second bending part (hereinafter, referred to as a two-part bending endoscope). The two-part bending endoscope includes, on a distal end portion side of an insertion portion in the following order from the distal end, a first bending part and a second bending part which are provided in a linked manner. The two-part bending endoscope includes a first bending knob for bending the first bending part and a second bending knob for bending the second bending part at an operation portion provided on the proximal end side of the insertion portion.

According to the two-part bending endoscope, the first bending part is bent by the operation of the first bending knob, on the other hand, the second bending part is bent by the operation of the second bending knob, thereby enabling smooth insertion of the insertion portion into an intricately curved lumen.

Now, description will be made on a procedure for inserting an insertion portion from a duodenum into a biliary tract, for example, by using the two-part bending endoscope.

As shown in FIG. 1, an operator causes the first bending part 101 configuring the insertion portion 100 to bend and causes an observation optical system, not shown, of the distal end portion 103 to face an orifice portion of the biliary tract 110. Then, an image in the vicinity of the biliary tract 110 is displayed on a screen (not shown).

Next, the operator appropriately operates the first bending knob and the second bending knob, which are not shown, while observing the screen. Then, the operator causes the first bending part 101 and the second bending part 102 to bend, to insert the insertion portion 100 into the deep part of the biliary tract 110 as shown by the arrow Y2 in FIG. 2.

Note that the reference numeral 104 represents a flexible tube portion and the reference numeral 111 represents the duodenum.

The two-part bending endoscope disclosed in the above patent document has a configuration in which the first bending part independently pedal ins a bending action by the operation of the first bending knob, and the second bending part independently performs a bending action by the operation of the second bending knob. Therefore, if the operator causes the second bending part 102 to bend in a state where the first bending part 101 is bent as shown by the solid lines in FIG. 1, the first bending part 101 and the distal end portion 103 move as shown by the dashed lines in conjunction with the bending of the second bending part 102. When the distal end portion 103 moves as shown by the dashed lines, the image of the biliary tract 110 displayed at the center of the screen, for example, gradually deviates from the screen according to the bending of the second bending part 102.

A technically accomplished operator causes two bending parts to bend as shown below, in order to prevent the image of the biliary tract 110 from deviating from the center of the screen in conjunction with the bending of the second bending part 102. That is, in order to constantly display the image of the biliary tract 110 on the screen, an experienced technician has repeatedly performed a second operation for bending the second bending part 102 in a desired direction by a desired amount and a first operation for bending the first bending part 101 in a direction opposite to the bending direction of the second bending part 102 by a desired amount.

SUMMARY OF THE INVENTION

A two-part bending endoscope according to one aspect of the present invention includes: a first bending part which configures one side of a bending portion, the bending portion configuring an insertion portion of an endoscope; a second bending part which configures the other end side of the bending portion, the second bending part being provided so as to be linked with the first bending part; and a bending portion operation apparatus which is provided to an operation portion provided so as to be linked with a proximal end of the insertion portion, the bending portion operation apparatus including a first operation device for causing the first bending part to perform a bending action and a second operation device for causing the second bending part to perform a bending action, wherein: the bending portion operation apparatus includes a selective power-transmitting mechanism section which enables at least a bending action of the first bending part by the first operation device, and an interlocking operation of the second bending part and the first bending part by the second operation device; the selective power-transmitting mechanism section is an independent rotation/co-rotation mechanism section; and the independent rotation/co-rotation mechanism section includes: a first rotation body whose cross-sectional shape is a regular polygon, the first rotation body being integrally fixed to a shaft configuring the first operation device; a second rotation body which is integrally fixed to a ring-shaped member configuring the second operation device, the second rotation body including a first rotation body arranging recessed portion in which the first rotation body is rotatably arranged and whose cross-sectional shape is a regular polygon, and a hole through which the shaft passes; a plurality of stepped pillar members, each including: a globe portion which has a predetermined diameter and which is arranged in a gap formed by an inner surface of the first rotation body arranging recessed portion and an outer surface of the first rotation body; a small-diameter portion to which the globe portion is integrally fixed; and a large-diameter portion configuring a sliding portion; and a rotational force transmission switching section including a through hole through which the shaft passes, long holes in which the respective small-diameter portions of the stepped pillar members are slidable, the long holes being formed in an elongated shape in a central axis direction of the through hole, and a case body having a space portion in which the respective large-diameter portions of the stepped pillar members are slidably arranged.

A two-part bending endoscope according to another aspect of the present invention includes: a first bending part which configures one side of a bending portion provided to an insertion portion of an endoscope; a second bending part which configures the other end side of the bending portion, the second bending part being provided so as to be linked with the first bending part; a first bending part pulling wire configured to bend the first bending part by being pulled; a second bending part pulling wire configured to bend the second bending part by being pulled; a first operation device which is provided to an operation portion provided so as to be linked with a proximal end of the insertion portion and configured to cause the first bending part to perform a bending action by pulling the first bending part pulling wire; a second operation device which is provided to the operation portion and configured to cause the first and second bending parts to perform a bending action in an interloking manner by pulling both of the first bending part pulling wire and the second bending part pulling wire simultaneously; and a selective power-transmitting mechanism section which transmits a bending operation of the first operation device only to the first bending part pulling wire or transmits a bending operation of the second operation device to both of the first bending part pulling wire and the second bending part pulling wire.

BRIEF DESCRIPTION OF THE DRAWINGS

FIGS. 3 to 17D relate to an embodiment of a bending portion operation apparatus including a selective power-transmitting mechanism section. FIG. 3 is a view illustrating a two-part bending endoscope that includes at the insertion portion a bending portion configured by including the first bending part and the second bending part.

FIG. 6 is a view illustrating a bending portion operation apparatus provided with a first operation device, a second operation device, and a selective power-transmitting mechanism section.

FIG. 7 is an illustration diagram which shows the bending portion operation apparatus viewed from the direction shown by the arrows Y7 and includes a cross-sectional view taken along the Y7-Y7 line shown by the arrows in FIG. 6.

FIG. 8 is a cross-sectional view in the longitudinal direction of a knob shaft, which illustrates a configuration of an independent rotation/co-rotation mechanism section.

FIG. 9 is a cross-sectional view taken along the Y9-Y9 line shown by the arrows in FIG. 8.

FIG. 10 is a view illustrating a state where, when a first rotation body of the independent rotation/co-rotation mechanism section is rotated, an outer surface of the rotating first rotation body abuts globe portions.

FIG. 11 is a view illustrating a state where the first rotation body is further rotated.

FIG. 12 is a view illustrating a state where, when a second rotation body of the independent rotation/co-rotation mechanism section, an inner surface of the second rotation body abuts the globe portions.

FIG. 13 is a view illustrating a co-rotation state where the first rotation body rotates in conjunction with the rotation of the second rotation body.

FIG. 14 is a view illustrating a state where the distal end portion of the insertion portion of the endoscope is inserted into the vicinity of a duodenal papilla.

FIG. 15 is a view illustrating a procedure for bending the first bending part of the bending portion by operating the first operation device of the bending portion operation apparatus included in the endoscope, to observe the orifice portion of the biliary tract.

FIG. 16 is a view illustrating a procedure for bending the second bending part and the first bending part in a co-rotation manner by operating the second operation device of the bending portion operation apparatus included in the endoscope, to insert the insertion portion into the biliary tract.

FIG. 17A is a view showing the first bending part configured to be bent in four directions, i.e., in up, down, left and right directions.

FIG. 17B is a view showing the second bending part configured to be bent in two directions, i.e., in up and down directions.

FIG. 17C and FIG. 17D are views illustrating yet another configuration of the first bending part and the second bending part included in the bending portion. FIG. 17C is a view showing the first bending part configured to be bent in two directions, i.e., up and down directions; and FIG. 17D is a view showing the second bending part configured to be bent in two directions, i.e., in up and down directions.

FIG. 20 is a cross-sectional view in the longitudinal direction of the knob shaft, which illustrates the action state selective switching section.

FIG. 21 is a cross-sectional view taken along the Y21-Y21 line shown by the arrows in FIG. 20.

FIG. 23 is a view illustrating a configuration of the overtube with bending portion.

FIG. 24 is a view illustrating a configuration of a grasping portion of the overtube.

FIG. 25 is a cross-sectional view taken along the Y25-Y25 line shown by the arrows in FIG. 24.

FIG. 26 is a view illustrating a working of the overtube.

FIG. 31 is a view illustrating a state where the distal end portion of the insertion portion is inserted into the biliary tract.

FIG. 32 is a view illustrating a state where a catheter main body is led out from a treatment instrument outlet hole of the endoscope into the biliary tract and a balloon in a deflated state is arranged at a deep part of the biliary tract.

FIG. 33 is a view illustrating a state where the balloon inflated by sending air thereinto is retained at the deep part of the biliary tract.

FIG. 34 is a view illustrating a state where the pushing-in operation of the insertion portion is performed with a distal end surface of a pusher tube being abutted an abutting surface of a channel hole and the insertion portion has been moved to the vicinity of the retained balloon.

FIG. 36 is a view illustrating another configuration of the endoscope insertion assisting instrument.

FIG. 37 is a perspective view illustrating a configuration of a distal end portion of a balloon sheath.

FIG. 38 is a cross-sectional view taken along the Y38-Y38 line shown by the arrows in FIG. 36.

FIG. 39 is a cross-sectional view taken along the Y39-Y39 line shown by the arrows in FIG. 36.

FIG. 40 is a view illustrating a state where air is sent into the balloon led out into the deep part of the biliary tract to retain the balloon at the deep part of the biliary tract.

FIG. 41 is a view illustrating a state where the pushing-in operation is performed with a pressing ring of a pusher portion being abutted an abutting surface of a channel hole and the insertion portion has been moved to the vicinity of the retained balloon.

FIG. 42 to FIG. 45D relate to views illustrating configurations and workings of the high-frequency dissection instrument for front-view endoscope. FIG. 42 is a view illustrating the high-frequency dissection instrument for front-view endoscope which includes a high-frequency dissection portion, a balloon catheter portion, and a knife portion housed in an outer-layer sheath.

FIG. 43 is a view illustrating a high-frequency dissection instrument for front-view endoscope having a knife portion protruded outside of the outer-layer sheath.

FIG. 45A to FIG. 45D relate to views illustrating the workings of the high-frequency dissection instrument for front-view endoscope. FIG. 45A is a view illustrating a state where the bending portion of the endoscope insertion portion is bent, the distal end portion is caused to face the orifice portion of the biliary tract, the balloon sheath is inserted in the biliary tract, and thereafter the balloon is retained in the biliary tract.

FIG. 45B is a view illustrating EST which is performed with the balloon being retained in the biliary tract.

FIG. 45C is a view illustrating the state where, after the EST is finished, the balloon sheath is inserted into the deep part of the biliary tract and the balloon is retained at the deep part of the biliary tract.

FIG. 45D is a view illustrating the endoscope insertion portion to be inserted by using the balloon sheath as a guide, with the balloon being retained at the deep part of the biliary tract.

FIG. 46 to FIG. 49B relate to views illustrating other exemplary configurations and workings of the high-frequency dissection instrument for front-view endoscope.

FIG. 46 is a view illustrating another configuration of the high-frequency dissection instrument for front-view endoscope.

FIG. 47 is a view illustrating a configuration of the knife portion.

FIG. 48 is a view illustrating a state where the knife portion is housed in the outer-layer sheath.

FIG. 49A and FIG. 49B relate to views illustrating the workings of a high-frequency knife for front-view endoscope. FIG. 49A is a view illustrating a positional relationship between the balloon and the outer-layer sheath when the balloon is retained in the biliary tract.

FIG. 49B is a view illustrating the EST performed with the balloon being retained in the biliary tract.

FIG. 50 to FIG. 52B relate to views illustrating exemplary configurations and workings of a high-frequency knife for front-view endoscope which is capable of easily setting a dissection direction. FIG. 50 is a view illustrating the high-frequency knife for front-view endoscope having a rotation direction restricting member at a distal end of the outer-layer sheath.

FIG. 51 is a cross-sectional view taken along the Y51-Y51 line shown by the arrows in FIG. 50.

FIG. 52A and FIG. 52B relate to views illustrating workings of the high-frequency knife for front-view endoscope. FIG. 52A is a view illustrating a best positional relationship between the orifice portion of the biliary tract and a marker which are displayed on a screen of a display apparatus.

FIG. 52B is a view illustrating the orifice portion of the biliary tract and the knife portion protruded in a desired direction, which are displayed on the screen of the display apparatus.

DETAILED DESCRIPTION OF THE PREFERRED EMBODIMENT(S)

Hereinafter, embodiments of the present invention are described with reference to FIGS. 3 to 16.

Figure 1:
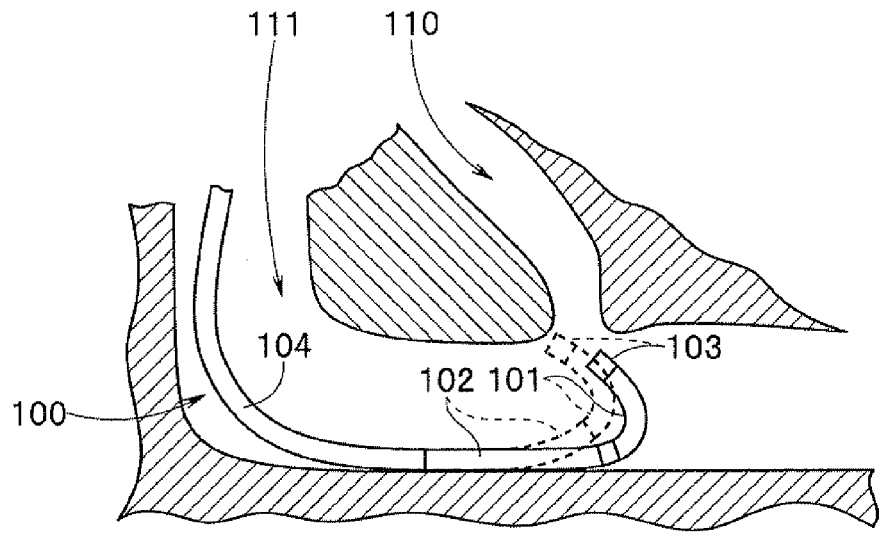
FIG. 1 is a view illustrating one state where an insertion portion provided with a first bending part and a second bending part is inserted into a duodenum and the first bending part is bent to cause an observation optical system of a distal end portion to face an orifice portion of a biliary tract, and the other state where the second bending part is bent in the one state, which causes the observation optical system to be deviated from the orifice portion of the biliary tract.
Figure 2:
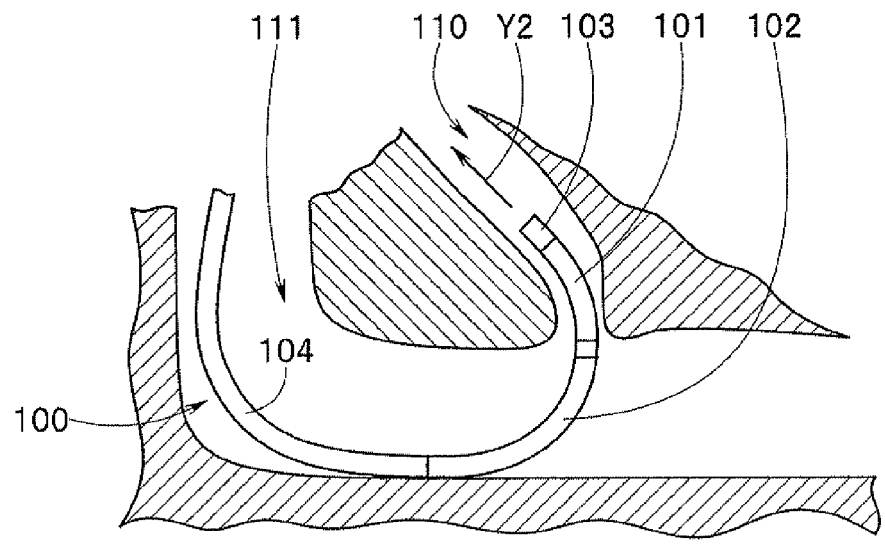
FIG. 2 is a view illustrating a state where the insertion portion provided with the first bending part and the second bending part is inserted into a biliary tract.
Figure 3:
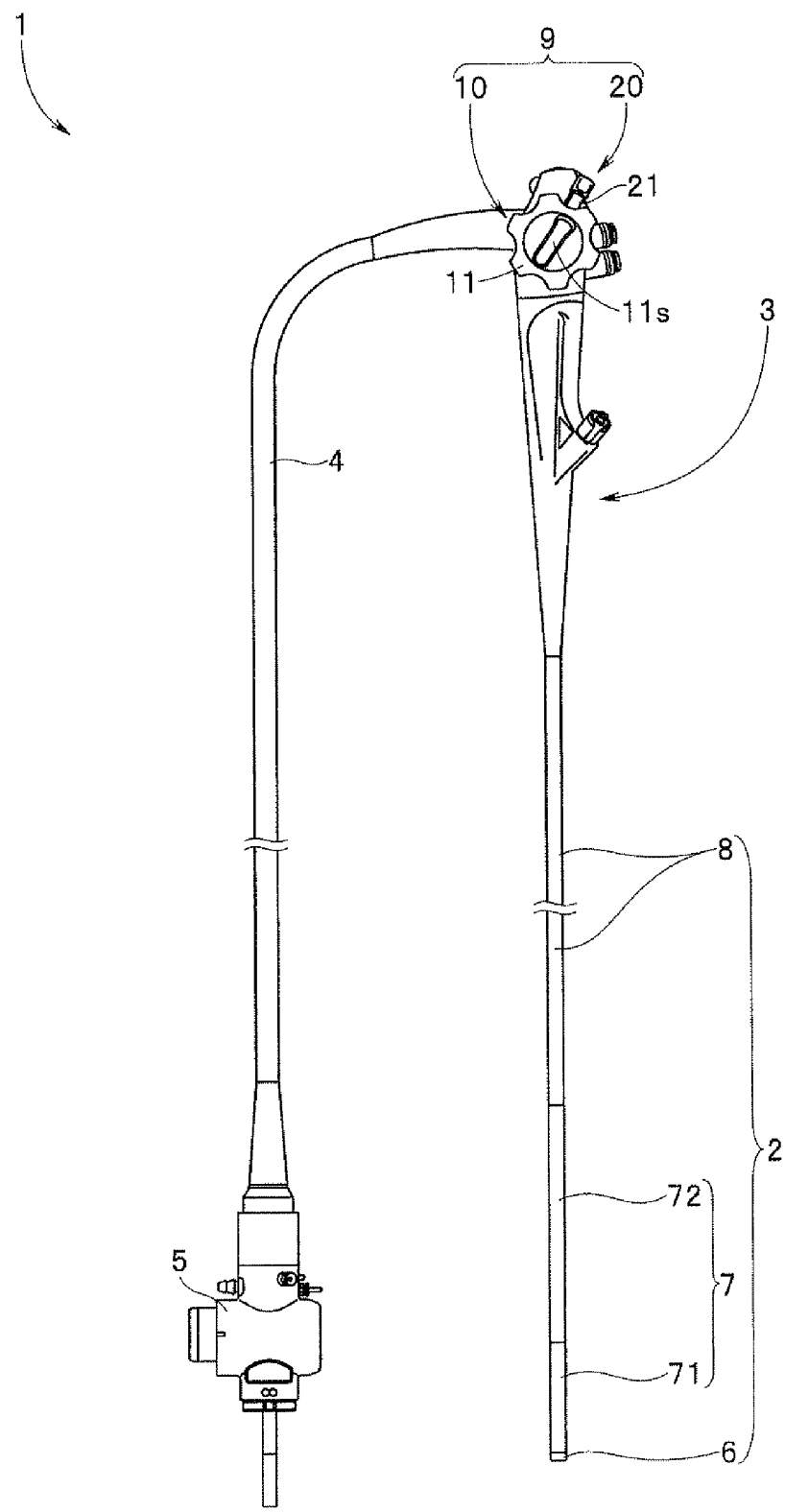

An endoscope 1 shown in FIG. 3 is a two-part bending endoscope. The endoscope 1 includes an elongated insertion portion 2, an operation portion 3, and a flexible universal cord 4. The insertion portion 2 has flexibility. The operation portion 3 is provided at the proximal end side of the insertion portion 2. The universal cord 4 extends from a side portion of the operation portion 3. An endoscope connector 5 is provided at the end portion of the universal cord 4. The endoscope connector 5 is detachably connected to a light source apparatus (not shown), for example, as an external apparatus.

The insertion portion 2 includes in the following order from the distal end side, a distal end portion 6, a bending portion 7 and a flexible tube portion 8 having flexibility, which are provided in a linked manner.

The endoscope 1 according to the present embodiment is a two-part bending endoscope, and includes a first bending part 71 and a second bending part 72 at the bending portion 7. The first bending part 71 configures the distal end side, for example, which is one side of the bending portion 7. The second bending part 72 configures the proximal end side, for example, which is the other side of the bending portion 7.

In the present embodiment, each of the first bending part 71 and the second bending part 72 has a bending piece group which includes a plurality of bending pieces arranged in a linked manner and which is configured to be bendable in at least two directions, for example, up and down directions.

Note that the endoscope of the present embodiment is intended to be inserted into a biliary tract. The positional relationship between the biliary tract and the insertion portion 2 is such that the running direction of the biliary tract is inclined in the counterclockwise direction when front-viewed from the side of the duodenal papilla into which the insertion portion 2 is inserted.

Figure 4A:
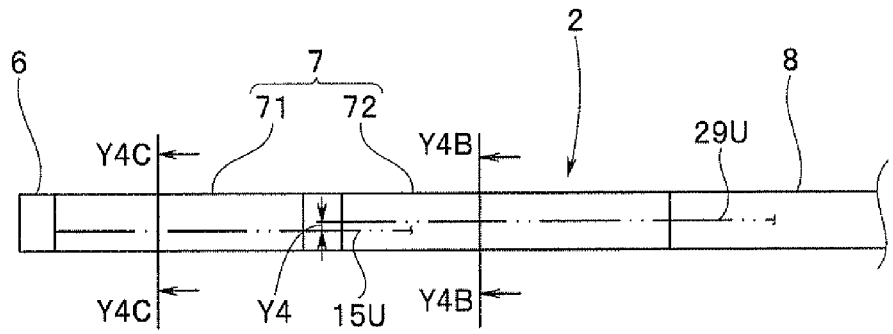
FIG. 4A is a view illustrating a positional relationship between a first bending part up-direction pulling wire of the first bending part and a second bending part up-direction pulling wire of the second bending part which configure the bending portion.
Figure 4B:
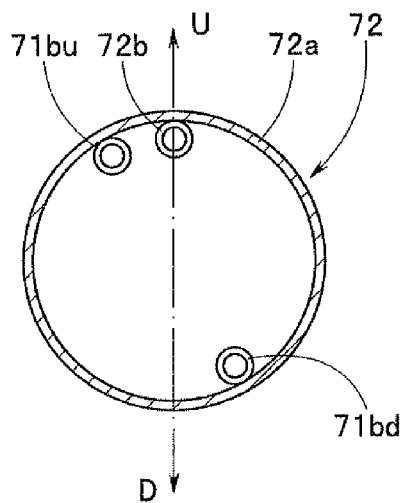
FIG. 4B is a cross-sectional view taken along the Y4B-Y4B line shown by the arrows in FIG. 4A.
Figure 4C:
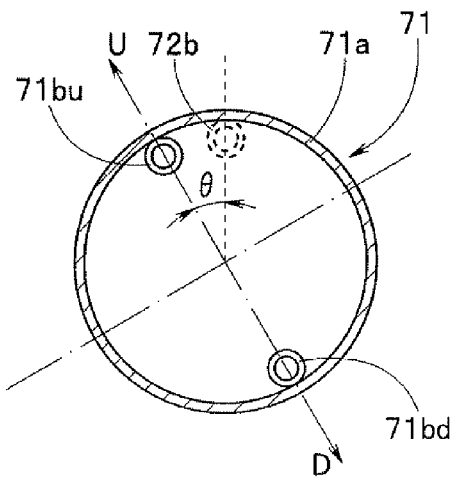
FIG. 4C is a cross-sectional view taken along the Y4C-Y4C line shown by the arrows in FIG. 4A.

Therefore, in the endoscope of the present embodiment, for the purpose of improving an introduction performance of the insertion portion 2 into the biliary tract, as shown in FIGS. 4A to 4C, a first bending part up-direction pulling wire (hereinafter, shortly referred to as first up-direction wire) 15U and a second bending part up-direction pulling wire (hereinafter, shortly referred to as second up-direction wire) 29U are arranged such that the insertion positions of the respective wires have a phase difference in the counterclockwise direction with respect to a circumferential direction, as shown by the arrow Y4. The first up-direction wire 15U is a wire of the first bending part 71, which is shown by the two-dot chain line, and the second up-direction wire 29U is a wire of the second bending part 72, which is shown by the two-dot chain line.

Specifically, a bending piece group 71a of the first bending part 71 configuring the bending portion 7 is connected to the bending piece group 72a of the second bending part 72 in a state being inclined from the side of the flexible tube portion 8 by an angle θ in the counterclockwise direction. The angle θ is within a range larger than 5 degrees and smaller than 45 degrees.

As shown in FIG. 4B, a wire holding member 72b is fixed at an up position which coincides with the up direction of the bending piece group 72a in the drawing. The second up-direction wire 29U is inserted in the wire holding member 72b.

On the other hand, a wire holding member 71bu is fixed at an up position of the bending piece group 71a arranged so as to be inclined with respect to the up direction in the drawing by an angle θ (30 degrees, for example), as shown in FIG. 4C. In the bending piece group 71a, a wire holding member 71bd is fixed so as to oppose to the wire holding member 71bu across the central point. The first up-direction wire 15U is inserted in the wire holding member 71bu, and a first down-direction wire 15D is inserted in the wire holding member 71bd.

According to such a configuration, the first bending part 71 is caused to bend when the insertion portion 2 is inserted into the biliary tract, to make the direction of the first bending part 71 coincide with the running direction of the biliary tract, thereby capable of obtaining an excellent insertion performance. In addition, the number of wires to be inserted in the bending portion 7 including the first bending part 71 and the second bending part 72 is reduced to a minimum needed number, thereby capable of reducing a size of the diameter of the insertion portion 2.

In the two-part bending endoscope 1 according to the present embodiment, the first bending part 71 configuring the bending portion 7 is connected to the second bending part 72 so as to be displaced by a predetermined angle in the counterclockwise direction viewed from the flexible tube portion 8 side. Therefore, an image pickup device, not shown, can be arranged with the up/down direction of the first bending part 71 used as a reference, or with the up/down direction of the second bending part used as a reference.

Figure 5A:
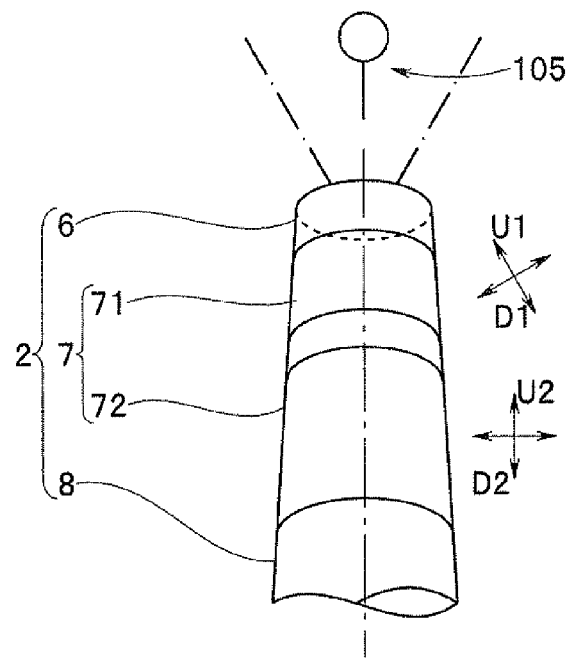
FIG. 5A is a pattern diagram showing a state where the distal end portion of the insertion portion is oriented to an observation target, the insertion portion being provided with a bending portion configured such that the up direction position of the first bending part and the up direction position of the second bending part deviate from each other in a circumferential direction.
Figure 5B:
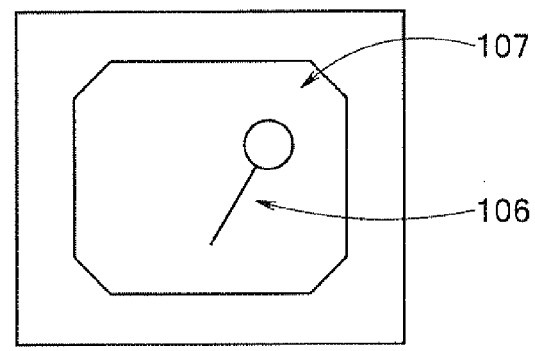
FIG. 5B is a view showing an endoscopic image picked up by an endoscope in which an up/down direction of an image pickup device which picks up an image of the observation target is made coincident with an up/down direction of the first bending part.

In the endoscope configured such that the vertical direction of the pixel alignment of the image pickup device is made coincident with the up/down direction (U1D1) of the first bending part 71 shown in FIG. 5A, the up/down direction of the endoscopic image displayed on the display screen 107 in FIG. 5B coincides with the up/down direction of the first bending part 71. Therefore, as shown in FIG. 5A, for example, when an observation target 105 standing upright so as to coincide with the up/down direction (U2D2 direction in the drawing) of the second bending part 72 is observed through an observation window (not shown) provided to the distal end surface of the distal end portion 6, an endoscopic image 106 of the observation target 105 is displayed so as to be inclined in the clockwise direction on the display screen 107.

According to such a configuration, the first bending part 71 of the endoscope 1 is operated more frequently than the second bending part 72 at the time of normal observation, thereby capable of obtaining a good observation performance at the time of normal observation.

Figure 5C:
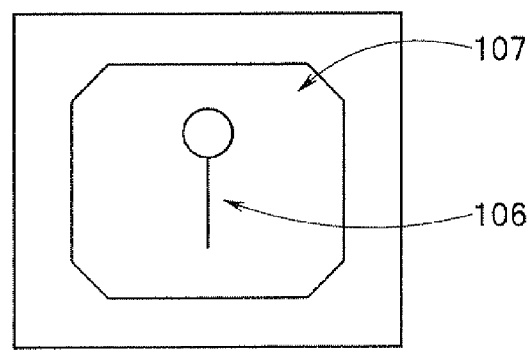
FIG. 5C is a view showing an endoscopic image picked up by an endoscope in which the up/down direction of the image pickup device which picks up an image of the observation target is made coincident with an up/down direction of the second bending part.

On the other hand, in the endoscope configured such that the vertical direction of the pixel alignment of the image pickup device is made coincident with the up/down direction (U2D2) of the second bending part shown in FIG. 5A, the up/down direction of the endoscopic image displayed on the display screen 107 as shown in FIG. 5C coincides with the up/down direction of the second bending part 72. Therefore, as shown in the above-described FIG. 5A, when the observation target 105 is observed, the endoscopic image 106 of the observation target 105 is displayed without being inclined on the display screen 107.

According to such a configuration, in a biliary tract insertion procedure which is the most difficult manual operation for an inexperienced operator, it is possible to obtain an excellent observation performance.

As shown in FIG. 3, the operation portion 3 is provided with a bending portion operation apparatus 9 for bending and operating the bending portion 7. The bending portion operation apparatus 9 includes a first operation device 10 and a second operation device 20. The first operation device 10 includes a bending knob 11 of a ring shape, for example. The second operation device 20 includes a bending lever 21 having a bar-like shape, for example.

The reference numeral 11s represents a bending knob fixing lever which fixes and holds the bending knob 11 at a desired rotation position.

Figure 7:
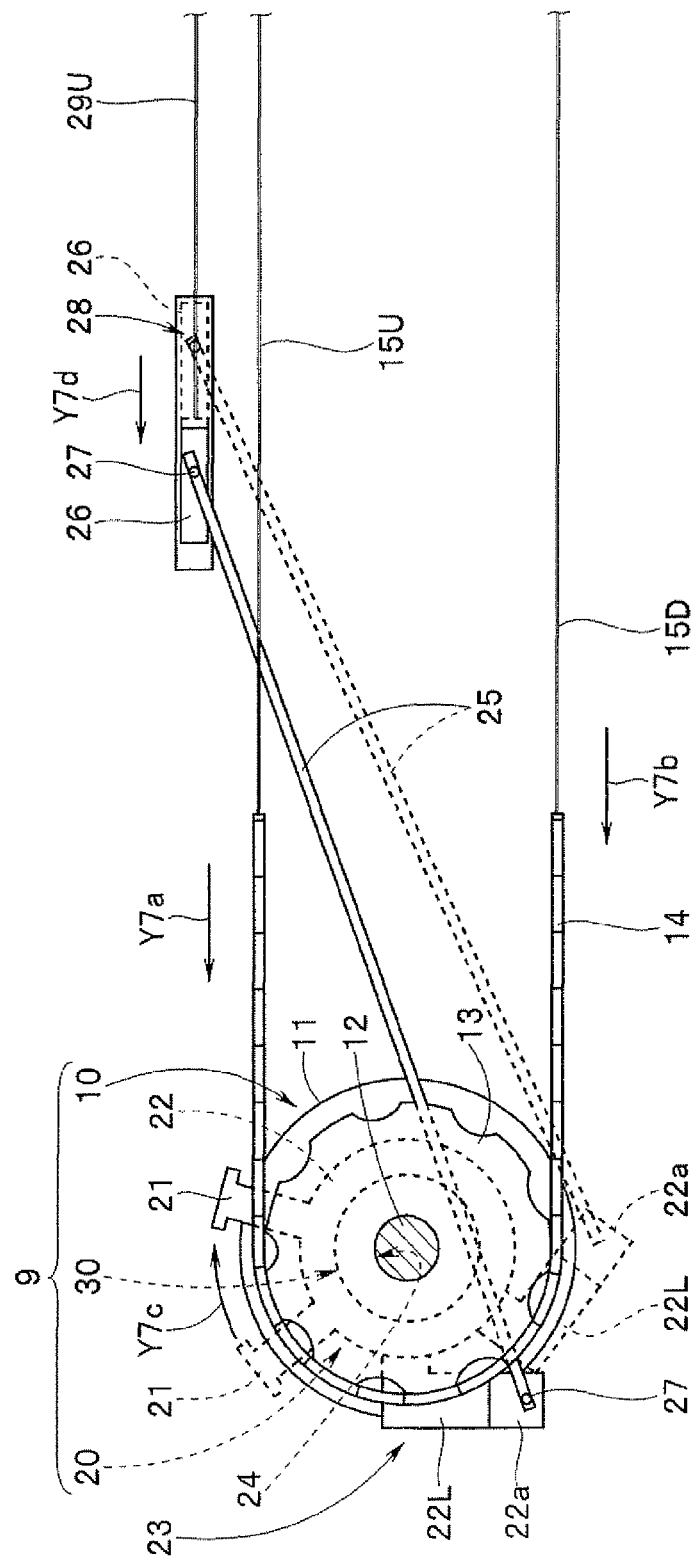

With reference to FIGS. 6 and 7, the relationship between the first operation device 10 and the second operation device 20, and the first bending part 71 and the second bending part 72 is described.

As shown in FIG. 6 and FIG. 7, the first operation device 10 includes a bending knob 11, a knob shaft 12, and a sprocket 13. On the other hand, the second operation device 20 includes the bending lever 21, a lever main body 22, and a linear motion link mechanism 23. The reference numeral 30 represents an independent rotation/co-rotation mechanism section which configures a selective power-transmitting mechanism section to be described later.

First, the configuration of the first operation device 10 will be described.

The bending knob 11 is a knob for bending the first bending part 71 in the up and down directions. When the first bending part 71 is caused to bend in the up direction, the bending knob 11 as shown in FIG. 7 is rotated in the counterclockwise direction.

The knob shaft 12 is vertically arranged on one plane of the bending knob 11. The longitudinal axis of the knob shaft 12 coincides with the center of the bending knob 11. The knob shaft 12 and the bending knob 11 are integrally fixed to each other by screwing by a screw member, adhesive bonding, welding, or the like.

The sprocket 13 is pivotally attached to a predetermined position of the knob shaft 12. The sprocket 13 is provided with a chain 14 arranged in a meshed manner. The proximal end portion of the first up-direction wire 15U is fixed to the one end portion of the chain 14. On the other hand, a proximal end portion of a first bending part down-direction pulling wire (hereinafter, shortly referred to as a first down-direction wire) 15D is fixed to the other end portion of the chain 14.

The distal end portion of the first up-direction wire 15U and the distal end portion of the first down-direction wire 15D are respectively fixed to predetermined positions of a first bending part distal end bending piece, not shown, which configures the bending piece group 71a of the first bending part 71.

According to the first operation device 10 configured as described above, when an operator operates the bending knob 11 in the counterclockwise direction, for example, the knob shaft 12 and the sprocket 13 first rotate in the counterclockwise direction in conjunction with the rotation of the knob 11. Next, the chain 14 and the first up-direction wire 15U are moved in the arrow Y7a direction in FIG. 7 in conjunction with the rotation of the sprocket 13. As a result, the first bending part 71 is bent in the up direction.

On the other hand, when the bending knob 11 is operated in the clockwise direction, for example, by the operator, the knob shaft 12 and the sprocket 13 rotate in the clockwise direction in conjunction with the rotation of the knob 11. Then, the chain 14 and the first down-direction wire 15D are moved in the arrow Y7b direction in FIG. 7 in conjunction with the rotation of the sprocket 13. As a result, the first bending part 71 is bent in the down direction.

Next, the configuration of the second operation device 20 will be described.

The bending lever 21 is a lever for bending the second bending part 72 in the up and down directions. When the second bending part 72 is bent in the up direction, the bending lever 21 is rotated from the position shown by the dashed line in the direction of the position shown by the solid line, as shown by the arrow Y7c in FIG. 7.

The lever main body 22 is a ring-shaped member having a through hole 24. The bending lever 21 is protruded from the outer circumferential surface of the lever main body 22. As shown in FIGS. 6 and 7, the through hole 24 of the lever main body 22 has a recessed portion 24a and a communicating hole 24b. The independent rotation/co-rotation mechanism section 30 is disposed in the recessed portion 24a. The communicating hole 24b communicates the recessed portion 24a with outside.

Note that the lever main body 22 and the bending lever 21 may be configured as an integrated structure or as separated structures. When the lever main body 22 and the bending lever 21 are configured as separate bodies, the lever main body 22 and the bending lever 21 are integrally configured by screwing with a screw member, adhesive bonding, welding, or the like.

The lever main body 22 is provided with a protrusion portion 22L configuring the linear motion link mechanism 23. The protrusion portion 22L is provided integrally with the bending lever 21 at a predetermined corresponding position.

Note that the lever main body 22 and the protrusion portion 22L may be configured as an integrated structure or as separated structures. When the lever main body 22 and the protrusion portion 22L are configured as separate bodies, the lever main body 22 and the protrusion portion 22L are integrally configured by screwing with a screw member, adhesive bonding, welding, or the like, similarly as in the relationship between the lever main body 22 and the bending lever 21.

The linear motion link mechanism 23 is configured by mainly including the protrusion portion 22L, a driving force transmitting rod 25, a sliding member 26, and connecting pins 27. The protrusion portion 22L is provided with a mounting portion 22a. One of the connecting pins 27 is arranged at the mounting portion 22a in a protruding manner. One end portion of the driving force transmitting rod 25 is rotatably connected to the one of the connecting pins 27.

The sliding member 26 is slidably arranged in a sliding groove 28 provided in the operation portion 3. The other one of the connecting pins 27 is provided on one surface side of the sliding member 26 in a protruding manner. The other end of the driving force transmitting rod 25 is rotatably connected to the other one of the connecting pins 27.

The proximal end portion of the second up-direction wire 29U is fixed to the distal-end-side end portion of the sliding member 26. The other end portion of the second up-direction wire 29U is fixed at a predetermined position of a second bending part distal end bending piece, not shown, which configures the bending piece group 72a of the second bending part 72.

According to the present embodiment, when the bending lever 21 is arranged at the position shown by the solid line in FIG. 7, the second bending part 72 is in the maximum bending state with respect to the up direction. At this time, the sliding member 26 configuring the linear motion link mechanism 23 is moved to the side closer to the bending portion operation apparatus 9.

Note that the bending lever 21 is configured to be fixable at a desired rotation position with a fixing tab not shown. In addition, the second bending part 72 according to the present embodiment is configured to be bent in only one direction, i.e., the up direction by the operation of the bending lever 21.

According to the second operation device 20 configured as described above, when the bending lever 21 is operated by the operator from the position shown by the dashed line in FIG. 7 in the direction of the arrow Y7c, the lever main body 22 which is configured integrally with the bending lever 21 rotates in the clockwise direction in the drawing.

In conjunction with the rotation of the lever main body 22, the protrusion portion 22L which is configured integrally with the lever main body 22 rotates from the position shown by the dashed line in the clockwise direction. Then, the driving force transmitting rod 25 connected to the mounting portion 22a of the protrusion portion 22L of the lever main body 22 through the connecting pin 27 is moved. In conjunction with the movement, the driving force transmitting rod 25 causes the sliding member 26 to move in the sliding groove 28, from the position shown by the dashed line in the direction of the arrow Y7d. As a result, the second up-direction wire 29U fixed to the sliding member 26 is pulled, which causes the second bending part 72 to bend in the up direction.

Lastly, description will be made on the independent rotation/co-rotation mechanism section 30.

Figure 8:
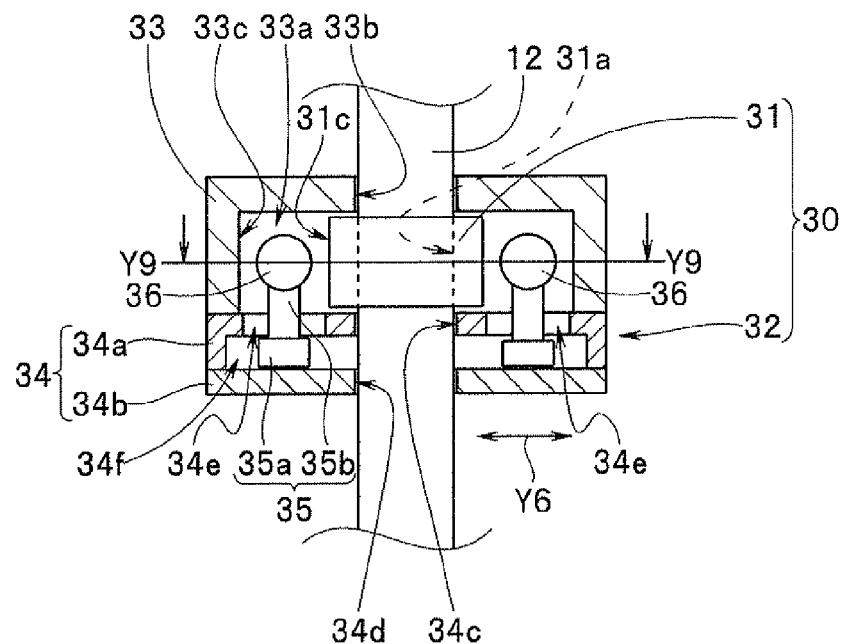
Figure 9:
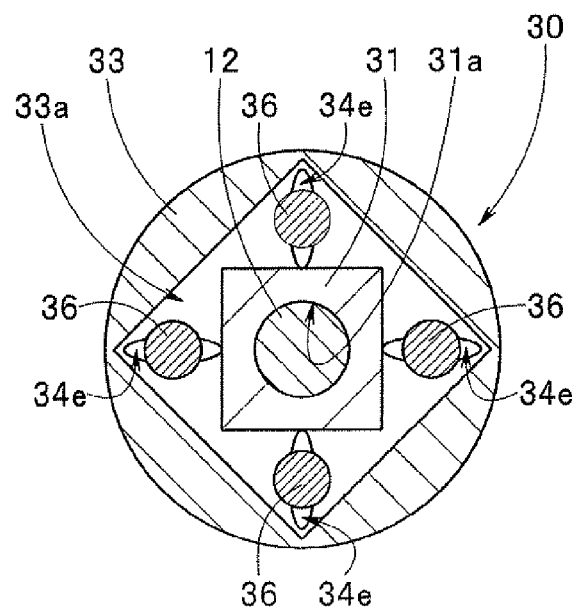

As shown in FIGS. 8 and 9, the independent rotation/co-rotation mechanism section 30 is configured by including a first rotation body 31 and a rotational force transmission switching section 32.

The first rotation body 31 is a rectangular parallelepiped, a cross sectional shape of which is a regular tetragon. The first rotation body 31 has a central through hole 31a. The knob shaft 12 is inserted in the central through hole 31a. The first rotation body 31 is integrally fixed to the knob shaft 12 with a screw member, for example, at a predetermined position of the longitudinal axis of the knob shaft 12. Therefore, the first rotation body 31 rotates integrally with the knob shaft 12 in conjunction with the rotation of the knob shaft 12.

The rotational force transmission switching section 32 includes a second rotation body 33, a case body 34, and moving members 35, and globe portions 36.

The second rotation body 33 is a cylindrical member. The second rotation body 33 is integrally fixed to the recessed portion 24a which configures the through hole 24 of the lever main body 22 by screwing with a screw member, adhesive bonding, welding, or the like. Therefore, the second rotation body 33 rotates integrally with the lever main body 22 in conjunction with the rotation of the lever main body 22.

A first rotation body arranging recessed portion (hereinafter, shortly referred to as arranging recessed portion) 33a and a communicating hole 33b are formed in the second rotation body 33. The arranging recessed portion 33a has a regular tetragonal-shaped cross section, for example. The communicating hole 33b communicates the arranging recessed portion 33a with outside.

The first rotation body 31 is rotatably disposed in the arranging recessed portion 33a. The knob shaft 12 is rotatably disposed in the communicating hole 33b.

The case body 34 has a two-body structure including a case main body 34a having a recessed portion and a lid body 34b, for example. The case main body 34a is fixed integrally to the second rotation body 33 by screwing with a screw member, adhesive bonding, welding, or the like. On the other hand, the lid body 34b is fixed integrally to the case main body 34a by screwing with a screw member, adhesive bonding, welding, or the like.

On the case main body 34a, a through hole 34c through which the knob shaft 12 is rotatably inserted is formed. Also on the lid body 34b, a through hole 34d through which the knob shaft 12 is rotatably inserted is formed. The case main body 34a has long holes 34e, which are a plurality of elongated through holes, formed from the outside of the case main body toward the direction of the central axis of the through hole 34c. The plurality of long holes 34e are formed four in number in accordance with the cross-sectional shape of the arranging recessed portion 33a. That is, in the present embodiment, the plurality of long holes 34e are formed around the central axis of the through hole 34c at intervals of 90 degrees in the circumferential direction.

Each of the moving members 35 is a stepped pillar member whose cross section is substantially T-shaped. Each of the moving members 35 includes a large-diameter portion 35a and a small-diameter portion 35b, for example. The large-diameter portion 35a is a sliding portion and slidably arranged in a space portion 34f. The space portion 34f is configured by the case main body 34a and the lid body 34b. The small-diameter portion 35b passes through one of the long holes 34e to be arranged in the arranging recessed portion 33a. The large-diameter portion 35a is slidable in the space portion 34f, and the small-diameter portion 35b is slidable with respect to one of the long holes 34e. That is, the respective moving members 35 are movable along the respective long holes 34e.

Each of the globe portions 36 is fixedly provided at the distal end portion of the small-diameter portion 35b of each of the moving members 35. The diameter dimension of the globe portions 36 is set to a predetermined dimension. Specifically, the diameter of the globe portions 36 is set based on a gap between inner surfaces 33c of the arranging recessed portion 33a and the outer surfaces 31c of the first rotation body 31, which are arranged opposed to each other.

Figure 10:
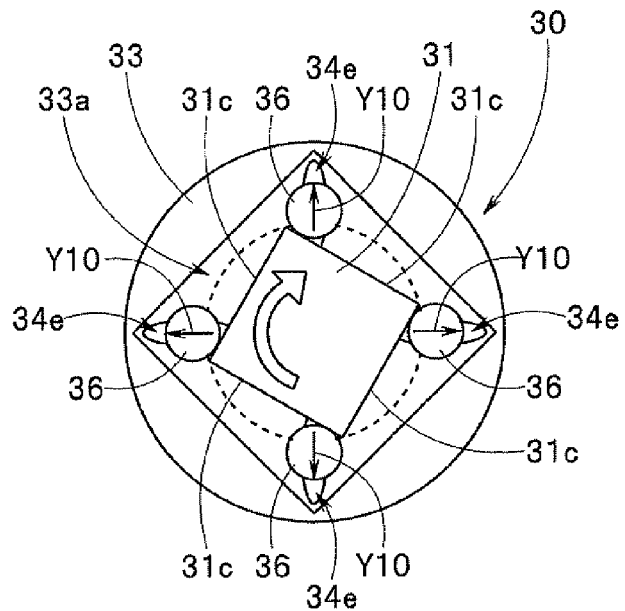

As shown in the arrow in FIG. 10, when the first rotation body 31 is rotated in the clockwise direction in the drawing, for example, the outer surfaces 31c abut the globe portions 36. After that, each of the globe portions 36 is moved along each of the long holes 34e as shown by each of the arrows Y10 in FIG. 10 in conjunction with the rotation of the first rotation body 31.

Figure 11:
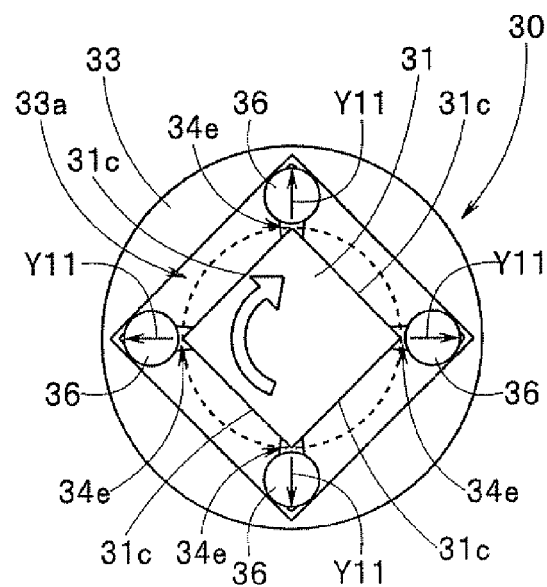

After that, the first rotation body 31 is further rotated, which causes the globe portions 36 to move to the corner portions of the arranging recessed portion 33a as shown by the arrows Y11 in FIG. 11. As a result, the first rotation body 31 independently rotates in the clockwise direction without being interfered with by the globe portions 36.

Note that, when the first rotation body 31 is rotated in the counterclockwise direction, the first rotation body 31 independently rotates in the counterclockwise direction. The circles shown by the dashed lines in FIG. 10 and FIG. 11 are moving trajectories of the four corners of the first rotation body 31. In addition, in the above-described embodiment, a recessed portion configuring the space portion 34f is provided to the case main body 34a. However, the recessed portion configuring the space portion 34f may be provided to the lid body 34b.

Figure 12:
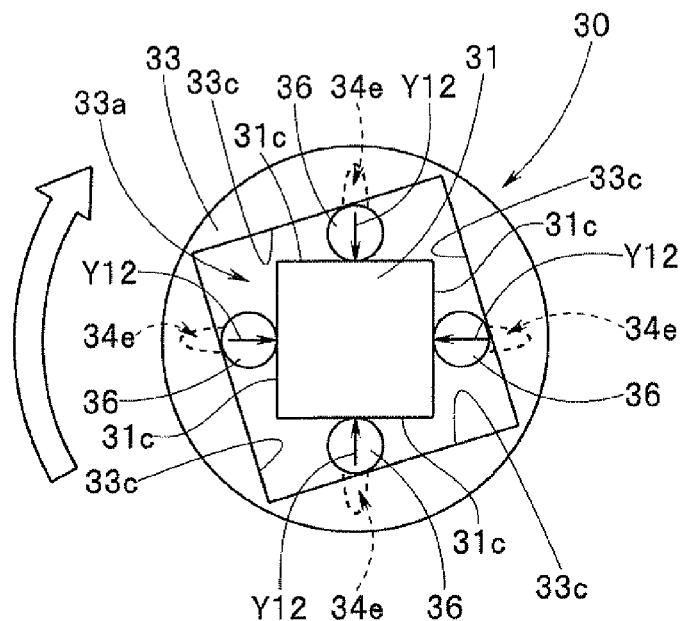

On the other hand, when the second rotation body 33 is rotated in the clockwise direction, for example, as shown by the arrow in FIG. 12, the inner surfaces 33c abut the globe portions 36. After that, each of the globe portions 36 is moved along each of the long holes 34e as shown by each of the arrows Y12 in FIG. 12 in conjunction with the rotation of the second rotation body 33, to abut each of the outer surfaces 31c.

Figure 13:
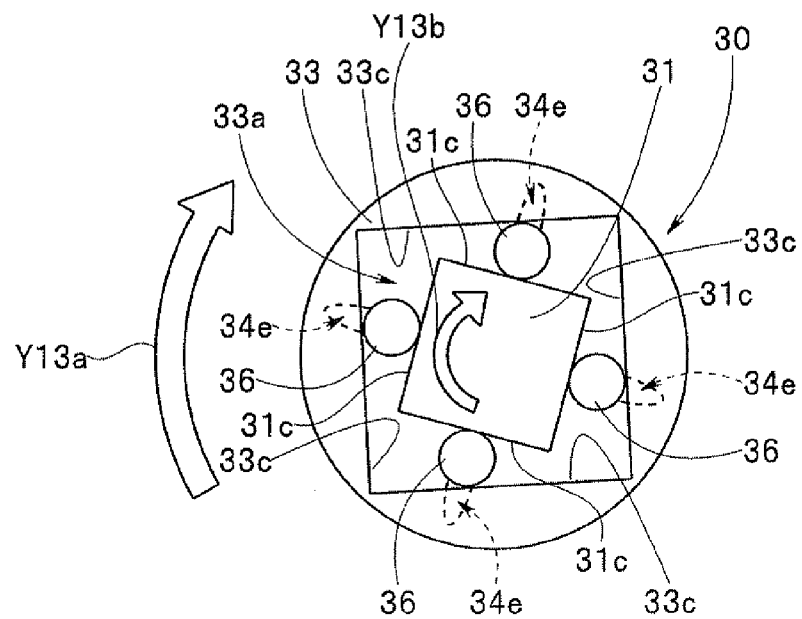

After that, the second rotation body 33 is further rotated, and thereby each of the globe portions 36 is held in a state being sandwiched by each of the inner surfaces 33c and each of the outer surfaces 31c, as shown in FIG. 13. That is, the second rotation body 33 and the first rotation body 31 are integrated by holding the globe portions 36 therebetween.

As a result, the rotational driving force of the second rotation body 33 is transmitted to the first rotation body 31 via the globe portions 36. Then, in conjunction with the clockwise rotation of the second rotation body 33 shown by the arrow Y13a, also the first rotation body 31 rotates in the clockwise direction as shown by the arrow Y13b. That is, the first rotation body 31 is rotated in conjunction with the rotation of the second rotation body 33.

As described above, the first rotation body 31 of the independent rotation/co-rotation mechanism section 30 is integrally fixed to the knob shaft 12 of the first operation device, and the second rotation body 33 of the independent rotation/co-rotation mechanism section 30 is fixed to the recessed portion 24a of the second operation device.

As a result, when the bending knob 11 is operated by the operator in the clockwise direction in FIG. 7, for example, also the knob shaft 12 and the first rotation body 31 shown in FIG. 9 are rotated in the clockwise direction in conjunction with the rotation of the knob 11. Then, as described above, the first bending part 71 is bent independently in the up direction. On the other hand, when the bending knob 11 is operated by the operator in the counterclockwise direction in FIG. 7, for example, also the knob shaft 12 and the first rotation body 31 as shown in FIG. 9 are rotated in the counterclockwise direction in conjunction with the rotation of the knob 11. As a result, as described above, the first bending part 71 is bent independently in the down direction.

When the operator operates the bending lever 21 from the position shown by the dashed line toward the direction of the arrow Y7c in FIG. 7, the lever main body 22 with which the bending lever 21 is integrally configured is rotated in the clockwise direction. At this time, the second rotation body 33, which is integrally arranged in the recessed portion 24a of the lever main body 22, rotates in the clockwise direction, and the protrusion portion 22L, which is provided integrally with the lever main body 22, rotates in the clockwise direction. As a result, the first rotation body 31 rotates in conjunction with the rotation of the second rotation body 33 as described above, which causes the second bending part 72 to bend in the up direction, and on the other hand, causes the first bending part 71 to bend in the down direction which is opposite to the bending direction of the second bending part 72.

According to the independent rotation/co-rotation mechanism section 30 of the present embodiment, when the operation of the bending knob 11 is selected, it is possible to perform operation to cause only the first bending part 71 to bend. On the other hand, when the operation of the bending lever 21 is selected, it is possible to perform operation to cause the first bending part 71 to bend in a predetermined direction in conjunction with the operation for bending the second bending part 72. That is, the independent rotation/co-rotation mechanism section 30 of the present embodiment is capable of selectively performing an independent operation for bending only the first bending part 71 by the bending knob 11 and a co-rotation operation for bending the first bending part in conjunction with the bending operation of the second bending part by the bending lever 21.

Note that, in the present embodiment, the cross-sectional shape of the first rotation body 31 is a regular tetragon. However, the cross-sectional shape of the first rotation body 31 is not limited to a regular tetragon, but may be a regular polygon such as a regular triangle, a regular hexagon, or a regular octagon. In addition, also the cross-sectional shape of the arranging recessed portion 33a in which the first rotation body 31 is disposed is not limited to the regular tetragon, and may be configured so as to coincide with the shape of the first rotation body 31.

Description will be made on the working of the two-part bending endoscope 1 configured as described above.

Figure 14:
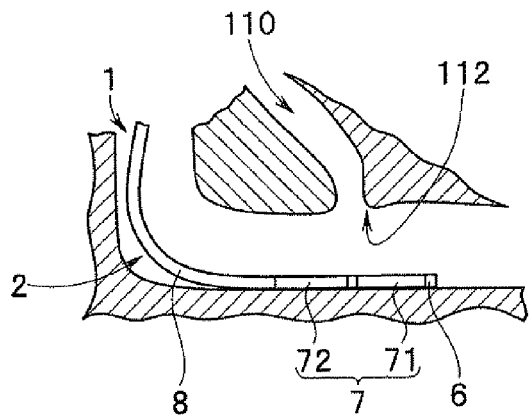

It is assumed that an operator performs a procedure for inserting the insertion portion 2 of the endoscope 1 with second bending part into the biliary tract 110 as shown in FIG. 14. At that time, the operator first inserts the distal end portion 6 of the insertion portion 2 in a desired position in the vicinity of the duodenal papilla 112.

Next, the operator obtains an endoscopic image of the biliary tract 110 by the endoscope 1 with second bending part. At that time, the operator operates the bending knob 11 of the first operation device 10 which configures the bending portion operation apparatus 9 provided in the operation portion 3. That is, the operator causes the first bending part 71 to bend in the up direction by operating the bending knob 11 in order to cause the distal end portion 6 to face the biliary tract 110.

Figure 15:
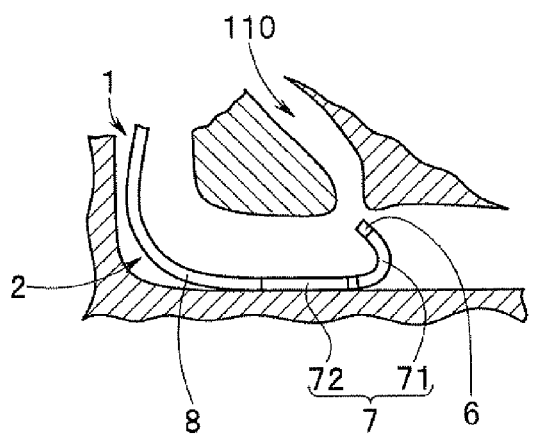

Then, in conjunction with the bending of the first bending part 71 in the up direction, an image of the biliary tract 110 is picked up by the observation optical system, not shown, provided in the distal end portion 6, and an endoscopic image including the biliary tract 110 is displayed on a screen of a display apparatus not shown. As shown in FIG. 15, the operator causes the distal end surface of the distal end portion 6 to face the orifice portion of the biliary tract to obtain a desired endoscopic image, and thereafter starts the insertion procedure of the insertion portion 2 into the biliary tract 110.

In order to insert the distal end portion 6 of the insertion portion 2 into the biliary tract 110, the operator operates the bending lever 21 of the second operation device 20 configuring the bending portion operation apparatus 9 provided in the operation portion 3. Then, in conjunction with the operation of the bending lever 21 by the operator, the second bending part 72 is caused to bend in the up direction and the first bending part 71 is caused to bend in the down direction.

Figure 16:
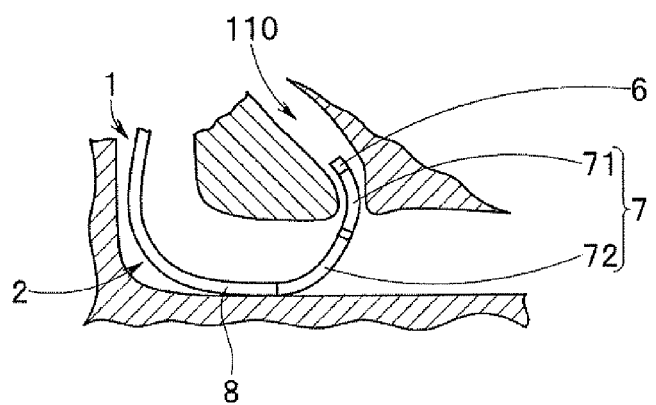

In other words, by the operation of the bending lever 21 by the operator, the second bending part 72 is gradually bent in the up direction, on the other hand, the first bending part bent in the up direction is gradually linearized. As a result, the operator causes the image of the biliary tract 110 to be constantly displayed at a desired position on the screen, thereby capable of inserting the insertion portion 2 toward the deep part of the biliary tract 110, as shown in FIG. 16.

The operation portion of the two-part bending endoscope is thus provided with the bending portion operation apparatus for bending and operating the bending portion which is provided to the insertion portion and configured by the first bending part and the second bending part. The bending portion operation apparatus includes the first operation device for bending and operating the first bending part, the second operation device for bending and operating the second bending part, and a selective power-transmitting mechanism section for causing the first operation device to perform bending operation in conjunction with the bending operation of the second operation device to bend the second bending part in one direction, and on the other hand, to bend the first bending part in a reverse direction of the one direction.

Accordingly, the bending portion is provided with the first bending part and the second bending part, thereby enabling the operator to be freed from inconvenience of bending operation of two kinds of operation devices provided in the operation portion, and capable of performing the biliary tract insertion procedure which is one of the most difficult manual operations.

Note that, in the endoscope 1 according to the present embodiment, the first bending part 71 constituting the bending portion 7 is configured to bend in the up and down directions, and the second bending part 72 is configured to bend in the up direction, as shown in FIGS. 4B and 4C. However, the configurations of the respective bending parts 71, 72 which constitute the bending portion 7 are not limited to the above configurations, and may be the configurations as shown in FIGS. 17A and 17B, or the configurations as shown in FIGS. 17C and 17D.

Figure 17A:
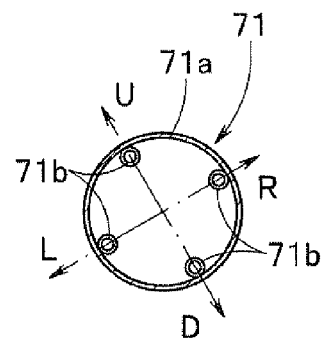
FIG. 17A and FIG. 17B are views illustrating another configuration of the first bending part and the second bending part included in the bending portion.
Figure 17B:
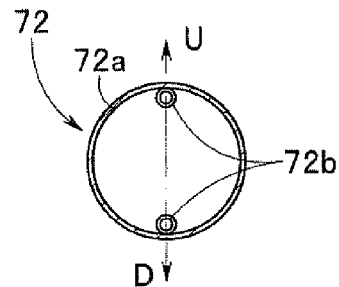
Figure 17C:
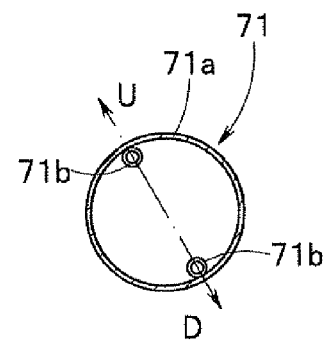
Figure 17D:
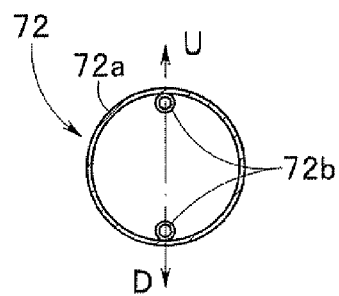

The bending portion 7 shown in FIGS. 17A and 17B is configured such that the first bending part 71 bends in four directions, that is, up, down, left and right directions, and the second bending part 72 bends in two directions, that is, up and down directions. On the other hand, the bending portion 7 shown in FIGS. 17C and 17D is configured such that the first bending part 71 and the second bending part 72 bend in two directions, that is, up and down directions.

In addition, in the above-described embodiment, the bending portion operation apparatus 9 provided with the first operation device 10 and the second operation device 20 includes, as the selective power-transmitting mechanism section, the independent rotation/co-rotation mechanism section 30 having the first rotation body 31 and the rotational force transmission switching section 32.

Figure 18:
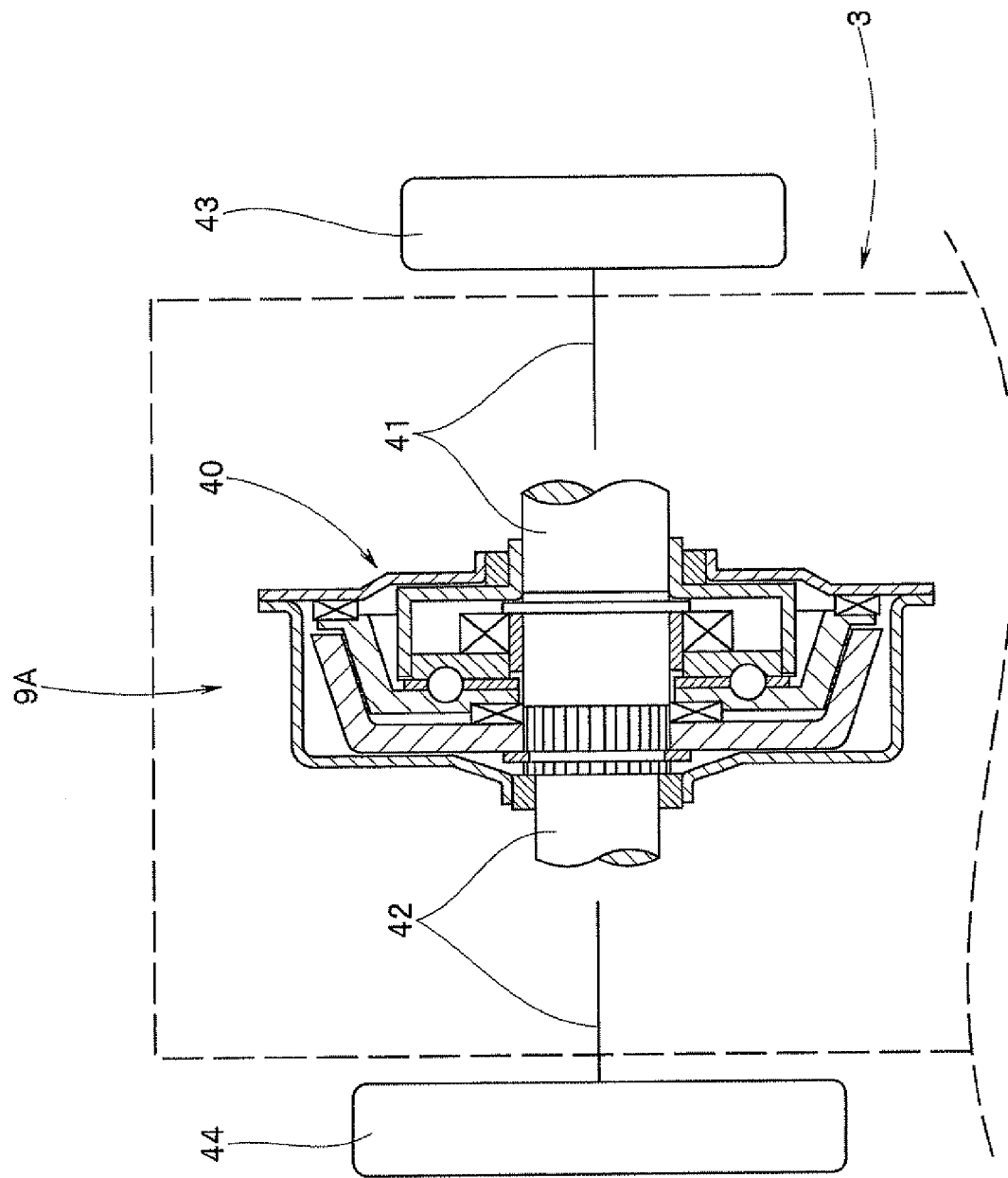
FIG. 18 is a view illustrating an exemplary configuration of an endoscope including a reverse input cutoff clutch, as the selective power-transmitting mechanism section, in the bending portion operation apparatus.
Figure 19:
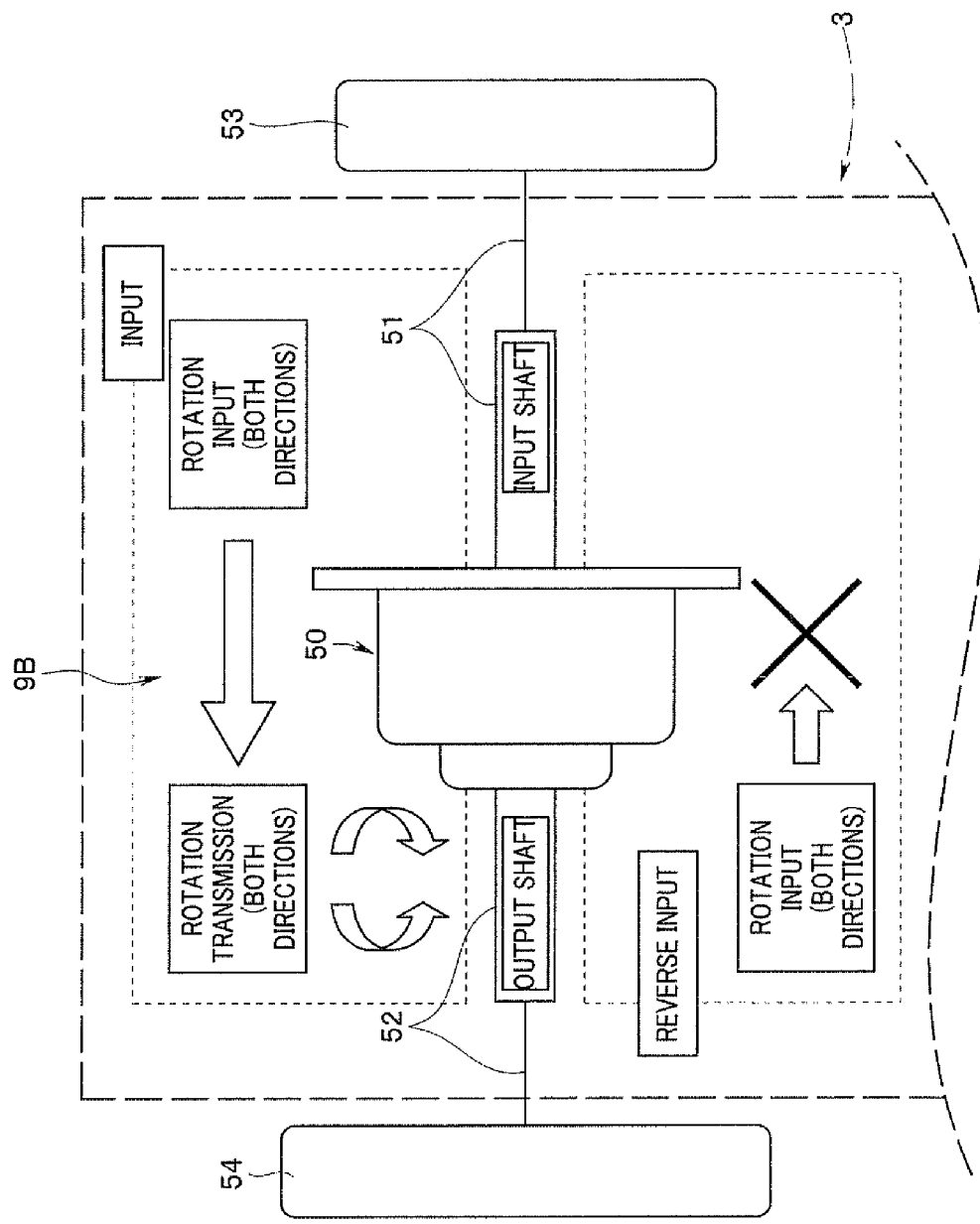
FIG. 19 is a view illustrating an exemplary configuration of an endoscope including an interactive clutch, as the selective power-transmitting mechanism section, in the bending portion operation apparatus.
Figure 20:
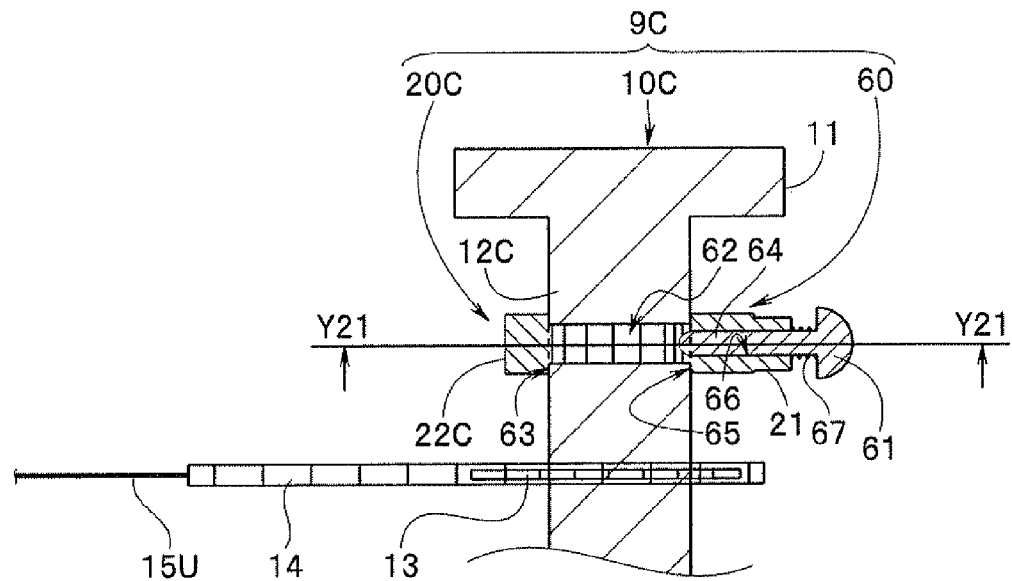
FIG. 20 and FIG. 21 are views illustrating a configuration of an endoscope provided with an action state selective switching section, as the selective power-transmitting mechanism section, in the bending portion operation apparatus.
Figure 21:
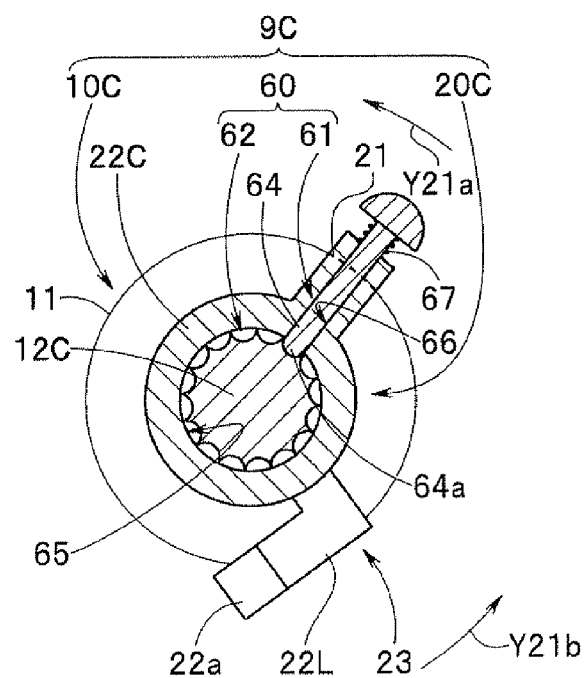

However, the configuration of the selective power-transmitting mechanism section provided in the bending portion operation apparatus 9 is not limited to the one described above, and the selective power-transmitting mechanism section may be the reverse input cutoff clutch 40 shown in FIG. 18, the interactive clutch 50 shown in FIG. 19, or an action state selective switching section 60 shown in FIGS. 20, 21.

The bending portion operation apparatus 9A according to the present embodiment as shown in FIG. 18 includes the reverse input cutoff clutch 40 as the selective power-transmitting mechanism section. The reverse input cutoff clutch 40 is a technology disclosed in the Japanese Patent Application Laid-Open Publication No. 2006-112524, and the clutch transmits the rotation torque inputted to an input shaft, but cuts off the reverse input from an output shaft to the input shaft.

In the present embodiment, a bending lever 43 for bending and operating the first bending part 71 and the second bending part 72 in conjunction with each other is fixedly provided to the input shaft 41 of the reverse input cutoff clutch 40. In addition, a bending knob 44 for independently bending and operating the first bending part 71 is provided to the output shaft 42 of the reverse input cutoff clutch 40. Therefore, in the present embodiment, the bending lever 43 and the bending knob 44 are disposed respectively on the opposed side surfaces of the operation portion 3.

The sprocket 13 to which the chain 14 is arranged in a meshed manner is pivotally attached to a predetermined position of the output shaft 42. The proximal end portion of the first up-direction wire 15U and the proximal end portion of the first down-direction wire 15D are fixed to the chain 14. On the other hand, at a predetermined position of the input shaft 41, the lever main body 22 including the linear motion link mechanism 23 for pulling the second up-direction wire 29U is fixedly provided.

According to this configuration, the same workings and effects as those of the above-described embodiment can be obtained by operating the bending lever 43 and the bending knob 44.

A bending portion operation apparatus 9B according to the present embodiment shown in FIG. 19 includes the interactive clutch 50 as the selective power-transmitting mechanism section. The interactive clutch 50 is a technology disclosed in "Development of Interactive clutch lock type (Shunichi Watanabe)" published in the document (Origin Technical Journal No. 70 (2007)). In the interactive clutch, when power is applied to the input shaft, the power is transmitted to the output shaft, but when power is applied to the output shaft, lock function works and no power is transmitted to the input shaft.

In the present embodiment, a bending lever 53 for bending and operating the first bending part 71 and the second bending part 72 in conjunction with each other is fixedly provided to the input shaft 51 of the interactive clutch 50. In addition, a bending knob 54 for independently bending and operating the first bending part 71 is fixedly provided to the output shaft 52 of the interactive clutch 50. Therefore, also in the present embodiment, similarly as in the above-described bending portion operation apparatus 9A, the bending lever 53 and the bending knob 54 are respectively disposed on the opposed side surfaces of the operation portion 3.

The sprocket 13 to which the chain 14 is arranged in a meshed manner is pivotally attached to a predetermined position of the output shaft 52. The proximal end portion of the first up-direction wire 15U and the proximal end portion of the first down-direction wire 15D are fixed to the chain 14. On the other hand, at a predetermined position of the input shaft 51, the lever main body 22 including the linear motion link mechanism 23 for pulling the second up-direction wire 29U is fixedly provided.

According to this configuration, the same workings and effects as those of the above-described embodiment can be obtained by operating the bending lever 53 and the bending knob 54.

As shown in FIGS. 20 and 21, a bending portion operation apparatus 9C according to the present embodiment includes a first operation device 10C, a second operation device 20C, and the action state selective switching section 60 as the selective power-transmitting mechanism section.

The action state selective switching section 60 includes a switching pin 61 and a groove 62. The switching pin 61 is a member to be engaged which configures a second operation device action switching section. The switching pin 61 is provided so as to be able to be pushed into the bending lever 21 protruding from the lever main body 22C. The groove 62 is an engaging portion, and provided in plural numbers at equal intervals in the circumferential direction of a knob shaft 12C.

Specifically, the first operation device 10C includes the bending knob 11, the knob shaft 12C, and the sprocket 13. A mounting portion 63 to which the lever main body 22C is rotatably mounted is provided to the knob shaft 12C. The mounting portion 63 includes the plurality of grooves 62 regularly aligned at predetermined positions.

On the other hand, the second operation device 20C includes the bending lever 21, the lever main body 22C, and the switching pin 61. The lever main body 22C is a ring-shaped member having a through hole 65. The bending lever 21, which is provided so as to be protruded from the outer circumferential surface of the lever main body 22C, includes a communicating hole 66 for communicating the through hole 65 with outside. The opening on the side of the through hole 65, where the communicating hole 66 is included, faces the grooves 62 in the state where the inner circumferential surface of the through hole of the lever main body 22C is arranged at the mounting portion 63 of the knob shaft 12C.

A shaft portion 64 of the switching pin 61 is slidably arranged in the communicating hole 66 of the bending lever 21. When the switching pin 61 is pushed in as shown in the drawing, a shaft distal end 64a is arranged in one of the grooves 62, and thereby the lever main body 22C and the knob shaft 12C are integrated with each other.

The reference numeral 67 represents a biasing member, which is a pushing spring, for example. The pushing spring 67 biases the head portion of the switching pin 61 to the outer circumferential side of the lever main body 22C. The shaft distal end 64a of the switching pin 61 is generally arranged on the outer side than the grooves 62 by the biasing force of the pushing spring 67.

Note that the switching pin 61 is configured to be holdable with a holding tab, not shown, in a state where the shaft distal end 64a is arranged in one of the grooves 62 or arranged on the outer side than the grooves 62.

Other configurations are the same as those of the above-described bending portion operation apparatus 9. The same members are attached with the same reference numerals, and description thereof will be omitted.

According to a first operation device 10C configured as described above, when the bending knob 11 is operated by the operator in a clockwise direction, for example, the knob shaft 12C and the sprocket 13 rotate in the clockwise direction in conjunction with the rotation of the knob 11. As a result, the first bending part 71 is bent in the up direction as described above.

When the bending knob 11 is operated by the operator in the counterclockwise direction, for example, the knob shaft 12C and the sprocket 13 rotate in the counterclockwise direction in conjunction with the rotation of the knob 11. As a result, the first bending part 71 is bent in the down direction as described above.

On the other hand, in the second operation device 20C configured as described above, the bending lever is operated in a state where the shaft distal end 64a of the switching pin 61 is arranged outside the grooves 62, or the shaft distal end 64a is arranged in one of the grooves 62. If the bending lever 21 is operated by the operator in the direction of the arrow Y21a in the drawing when the shaft distal end 64a is arranged outside the grooves 62, the lever main body 22C which is integrated with the bending lever 21 is rotated in the counterclockwise direction with respect to the knob shaft 12C. Then, the protrusion portion 22L which is integrated with the lever main body 22C rotates in the direction of the arrow Y21b, thereby causing the second bending part 72 to bend in the up direction, as described above.

On the other hand, when the operator moves the switching pin 61 against the biasing force of the pushing spring 67 to arrange the shaft distal end 64a in one of the grooves 62, the lever main body 22C and the knob shaft 12C are integrated with each other. At this time, when the bending lever 21 is operated by the operator in the direction of the arrow Y21a in the drawing, the lever main body 22C and the knob shaft 12C rotate in the counterclockwise direction in conjunction with the rotation operation of the bending lever 21. That is, similarly as in the above-described embodiment, the second bending part 72 is bent in the up direction, while the first bending part 71 is bent in the down direction.

That is, according to the action state selective switching section 60 of the present embodiment, the switching pin 61 is provided at the bending lever 21. As a result, an independent operation for only bending and operating the second bending part 72, and a co-rotation operation for bending and operating the first bending part 71 in a predetermined direction in conjunction with the bending operation of the second bending part 72 can be selectively performed by selecting the operation of the bending lever 21, and also an independent operation for only bending the first bending part 71 can be selectively performed by selecting the operation of the bending knob 11.

In the present embodiment, the bending portion operation apparatus 9C having the switching pin 61 is thus provided in the operation portion 3 of the endoscope 1. As a result, when rotating the bending lever 21, the operator switches the position of the shaft distal end 64a of the switching pin 61 selectively in one of the grooves 62 or outside the grooves 62, thereby capable of bending the second bending part 72 and the first bending part 71 in conjunction with each other or bending the second bending part 72 and the first bending part 71 independently of each other when operating the second operation device 20C.

Incidentally, in the procedure for inserting the insertion portion of the endoscope into the biliary tract, it is possible to consider a case in which an overtube with bending portion (hereinafter, shortly referred to as overtube) 120 and an endoscope 130 having a bending portion 132 at an insertion portion 131 are used in combination. The reference numeral 121 represents the bending portion of the overtube 120.

Figure 22A:
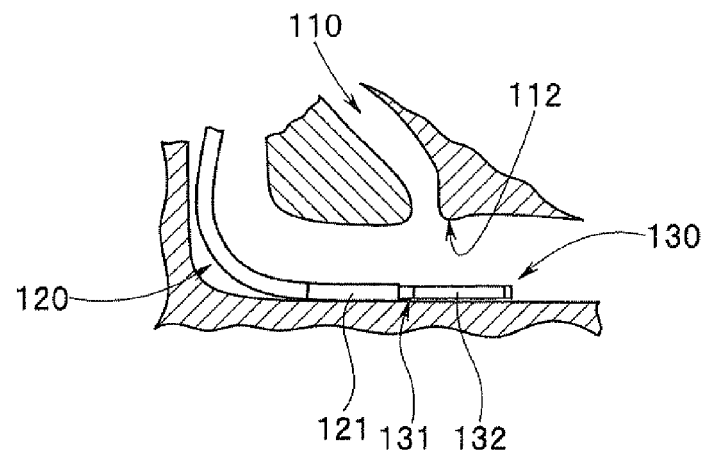
FIG. 22A is a view illustrating a state where the distal end portion of the insertion portion of the endoscope is inserted into the vicinity of the duodenal papilla through an overtube.

In this case, the operator appropriately performs manual operations of the overtube 120 and the endoscope 130. Specifically, as shown in FIG. 22A, the operator first arranges the distal end of the overtube 120 in the vicinity of the duodenal papilla 112, and causes the insertion portion 131 of the endoscope 130 to protrude from the distal end of the overtube 120. At this time, the whole of the bending portion 132 is exposed from the distal end of the overtube 120.

Figure 22B:
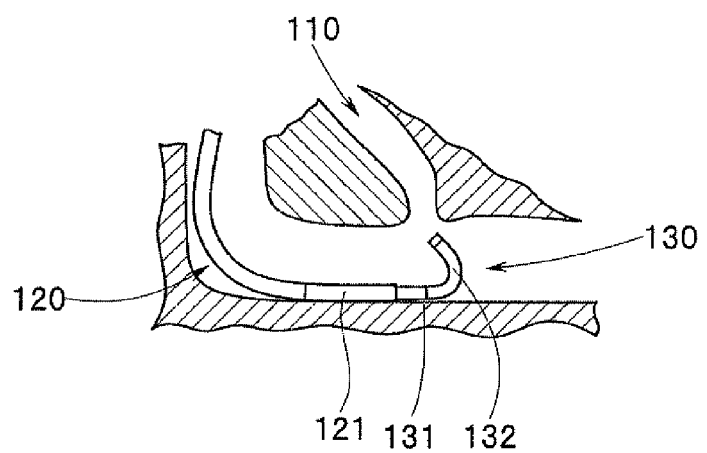
FIG. 22B is a view illustrating a procedure for bending the bending portion included in the insertion portion of the endoscope to observe the biliary tract.
Figure 22C:
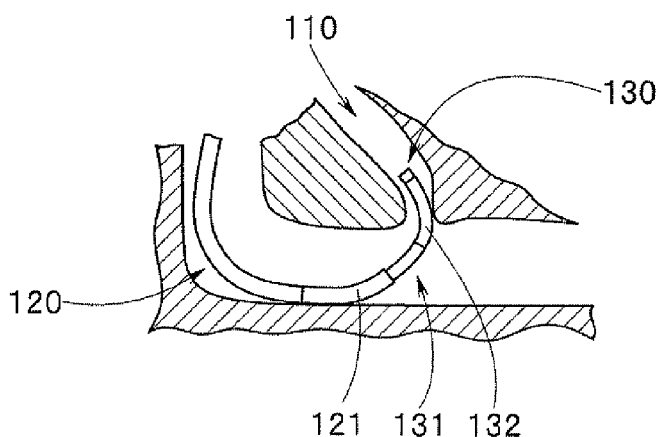
FIG. 22C is a view illustrating a procedure for respectively bending a bending portion of the overtube and the bending portion of the insertion portion of the endoscope, to insert the insertion portion into the biliary tract.

Next, as shown in FIG. 22B, the operator causes the bending portion 132 of the endoscope 130 to bend and causes an endoscopic image of the biliary tract 110 to be displayed on the screen of the display apparatus. After that, as shown in FIG. 22C, the operator starts to insert the insertion portion 2 into the biliary tract 110. At this time, the operator performs an operation for bending the bending portion 121 of the overtube 120 in the up direction and an operation for linearizing the bending portion 132 of the endoscope 130, thereby pushing the insertion portion 131 toward the deep part of the biliary tract 110.

When performing the above-described procedure, the operator grasps the operation portion of the endoscope 130 including a bending operation knob with the left hand, for example. Then, the operator grasps the grasping portion of the overtube 120 including a bending operation lever with the right hand.

However, the insertion length by which the overtube 120 is inserted into a body differs depending on the luminal length, the luminal shape, and the like of a patient. Therefore, there is a case where the operator cannot operate the bending operation lever, with the grasping portion of the overtube 120 constantly arranged in the vicinity of the mouth of the patient.

During the examination and the like, if the grasping portion of the overtube 120 is moved away from the mouth of the patient, there might be a case where the overtube 120 positioned between the mouth and the grasping portion hangs down due to own weight of the tube or the weight of the insertion portion 131 inserted in the overtube 120.

If the overtube 120 hangs down as described above, the distal end position of the overtube inserted into a body or the distal end position of the insertion portion changes. Therefore, there has been a desire for an overtube, the grasping portion of which can be always arranged in the vicinity of the mouth of the patient regardless of the insertion length.

FIG. 23 is a view describing a configuration of an overtube with bending portion.

As shown in FIG. 23, an overtube with bending portion 140 is configured mainly by a tube body 142 and a grasping portion with bending operation lever (hereinafter, shortly referred to as grasping portion) 143. The tube body 142 includes at the distal end side thereof a bending portion 141. The grasping portion 143 is arranged at the proximal end of the tube body 142.

The tube body 142 is a multi-lumen tube having flexibility, for example. The tube body 142 includes a large-diameter through hole through which the insertion portion 131 of the endoscope 130 is inserted, and a small-diameter through hole through which a bending wire 144 for bending the bending portion 141 is inserted. The distal end portion of the bending wire 144 is fixed at a predetermined position of the bending portion 141.

At the proximal end portion of the tube body 142, a circumferential projection portion 142a, what is called a flange is provided. The circumferential projection portion 142a prevents the grasping portion 143 from falling off from the proximal end side of the tube body 142.

The grasping portion 143 is formed in a shape of a rigid pipe with a resin member, for example. In the through hole of the grasping portion 143, the tube body 142 is advanceably/retractably inserted in the axis direction. That is, the grasping portion 143 is advanceable/retractable with respect to the longitudinal direction of the tube body 142, and rotatable in the circumferential direction.

The bending operation lever 146 is rotatably mounted to the grasping portion 143 through a pin 145. At one end portion of the bending operation lever 146, the proximal end portion of the bending wire 144 is fixed. The proximal end side of the bending wire 144 is extended from the through hole of the tube body 142. The reference numeral 147 represents a wire sheath. The bending wire 144 is inserted in the wire sheath 147. The distal end portion of the wire sheath 147 is integrally fixed to the small-diameter through hole of the tube body 142. The proximal end portion of the sheath 147 is integrally fixed at a predetermined position of the grasping portion 143.

The bending operation lever 146 is configured such that the pulling amount of the bending wire 144 is constant regardless of the position in the longitudinal axis direction of the tube body 142 of the grasping portion 143. When the bending operation lever 146 is rotated to the position shown by the solid line in the drawing, the bending portion 141 is brought into the maximum bending state shown in the drawing. Note that the bending portion 141 is in the linear state when the bending operation lever 146 is at the position shown by the two-dot chain line.

The grasping portion 143 includes, at predetermined positions of the outer surface thereof, a notch 148 and a communicating hole 149. The communicating hole 149 communicates the inner surface with the outer surface of the grasping portion 143. Therefore, the outer surface of the tube body 142 is exposed outside through the notch 148 and the communicating hole 149 of the grasping portion 143.

Therefore, the operator can grasp the tube body 142 exposed through the notch 148 and the communicating hole 149 together with the grasping portion 143. In such a grasped state, the grasping portion 143 is arranged integrally with respect to the tube body 142.

According to the overtube 140 configured as described above, the position of the grasping portion 143 of the overtube 140 can be moved with respect to the tube body 142 in accordance with the insertion length of the tube body 142 inserted into a body. In addition, the movable grasping portion 143 can be arranged integrally with the tube body 142.

Therefore, the operator can perform manual operations of the endoscope 130 and the overtube 140, with the grasping portion 143 always arranged at a desired position in the vicinity of the mouth 115 of the patient. In addition, in such an operation state, the overtube 140 is prevented from hanging down.

Figure 24:
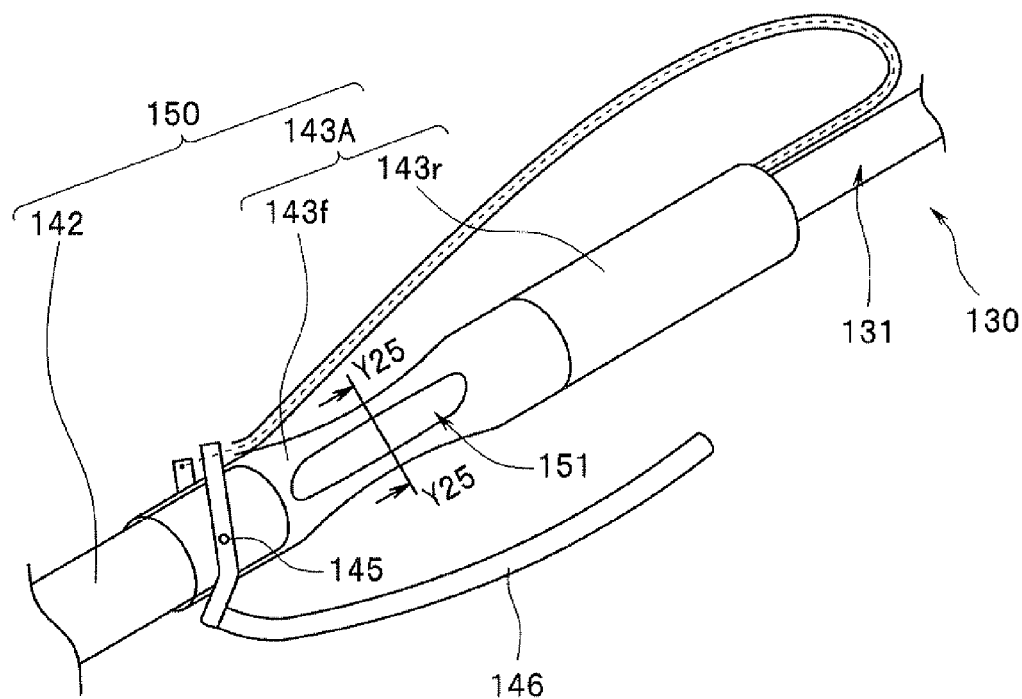
FIG. 24 to FIG. 26 relate to other exemplary configurations of the overtube with bending portion.
Figure 25:
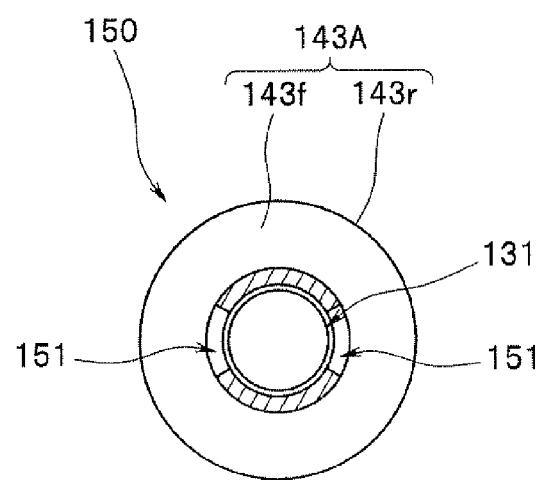
Figure 26:
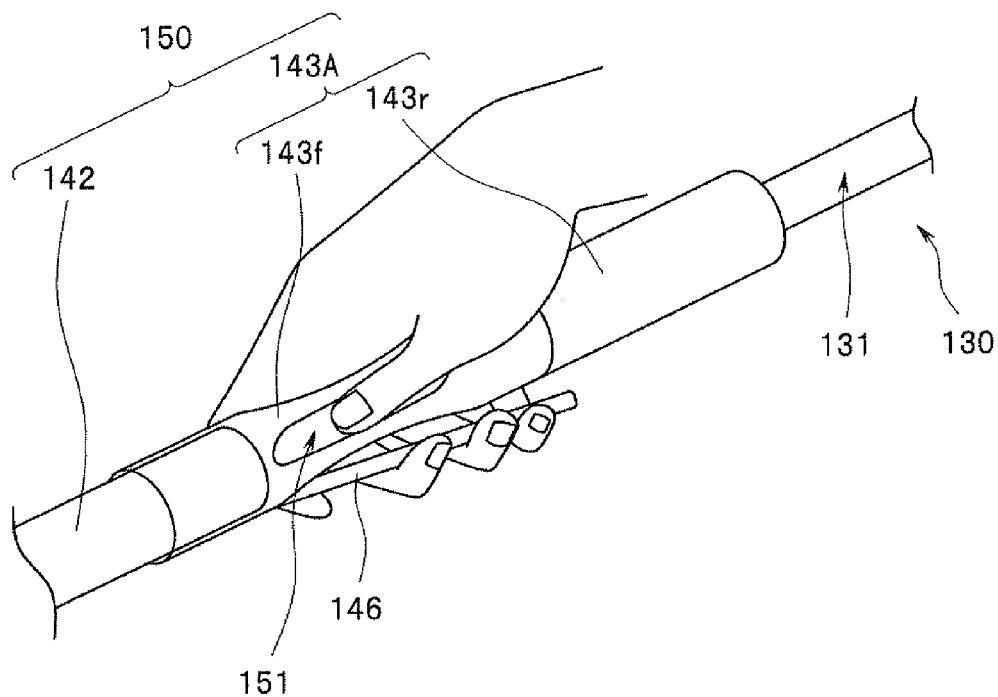

Note that the configuration of the overtube 140 is not limited to the above-described configuration in which the notch 148 and the communicating hole 149 are provided to the grasping portion 143, and the overtube may be configured as an overtube 150 having configurations shown in FIGS. 24 to 26.

FIG. 24 to FIG. 26 relate to other exemplary configurations of the overtube with bending portion in which: FIG. 24 is a view illustrating a configuration of a grasping portion of the overtube; FIG. 25 is a cross-sectional view taken along the Y25-Y25 line shown by arrows in FIG. 24; and FIG. 26 is a view illustrating a working of the overtube.

As shown in FIG. 24, a grasping portion 143A of the overtube 150 according to the present embodiment includes a first grasping portion 143f and a second grasping portion 143r. The first grasping portion 143f and the second grasping portion 143r configure the distal end side and the proximal end side of the grasping portion 143A, respectively.

The first grasping portion 143f is provided with a pair of communicating holes 151 formed in an opposed positional relationship as shown in FIG. 25, for causing the outer surface of the tube body 142 to be exposed. The second grasping portion 143r is a pipe-shaped member. Other configurations are the same as those of the overtube shown in FIG. 23. The same members are attached with the same reference numerals and the description thereof will be omitted.

According to the overtube 150 configured as described above, by grasping the grasping portion 143A as shown in FIG. 26, the action of grasping the bending operation lever 146, the manual operation of inserting the insertion portion 131 of the endoscope 130 into a body, and the action of grasping the overtube 150 can be simultaneously performed.

Other workings and effects are the same as those of the overtube in the above-described FIG. 23.

Figure 27:
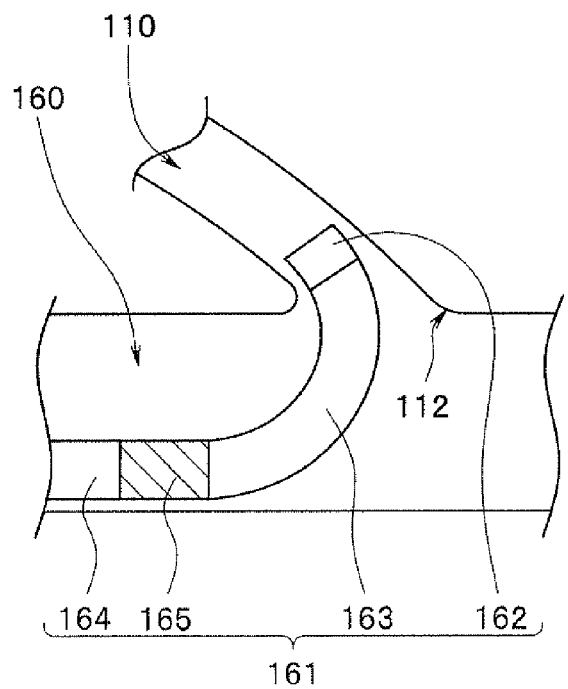
FIG. 27 is a view illustrating a state where the distal end portion of the insertion portion into the biliary tract, the insertion portion including a connecting tube which is made of a rigid member and configured to connect the proximal end side of the bending portion and the distal end side of a flexible tube portion.

Incidentally, in an insertion portion 161 of an endoscope 160 as shown in FIG. 27, the proximal end side of the bending portion 163 and the distal end side of the flexible tube portion 164 are connected by a connecting tube 165 made of a rigid member.

In the procedure for inserting the insertion portion 161 into the biliary tract 110, the operator causes the bending portion 163 to bend, to insert the distal end portion 162 into the biliary tract 110 from the vicinity of the duodenal papilla 112. After that, the operator pushes the insertion portion 161 toward the deep part of the biliary tract 110. At that time, the operator performs the pushing-in operation of the insertion portion 161 as shown by the arrow Y28a in FIG. 28.

Figure 28:
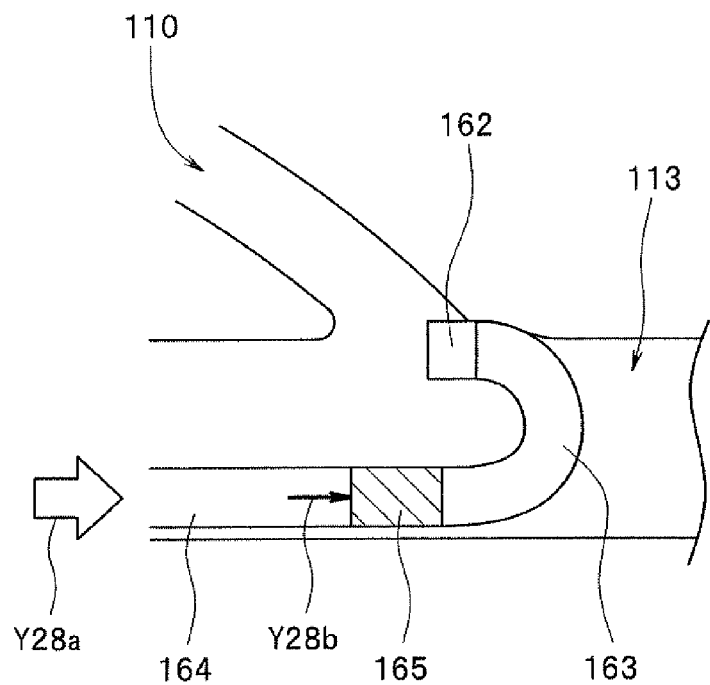
FIG. 28 is a view illustrating a problem which may occur when a pushing-in operation of the insertion portion is performed with the distal end portion of the insertion portion arranged in the biliary tract as shown in FIG. 27.

At this time, as shown in FIG. 28, when a force as shown by the arrow Y28b acts on the connecting tube 165 as a rigid portion, the insertion portion 161 is pushed toward the side of the small intestine 113. As a result, there is a possibility that the distal end portion 162 inserted in the biliary tract 110 falls off from inside of the biliary tract 110. When the distal end portion 162 falls off from inside of the biliary tract 110, the operator has to perform insertion procedure of the insertion portion 161 into the biliary tract 110 all over again.

Figure 29:
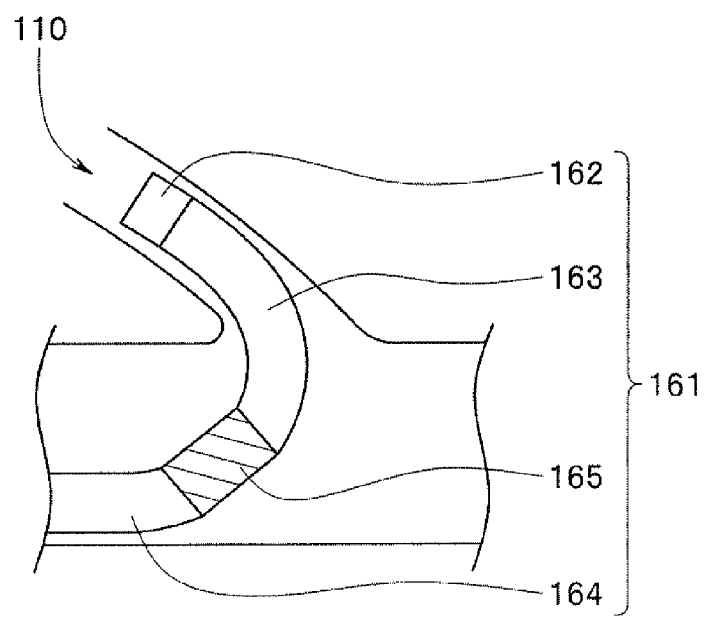
FIG. 29 is a view showing an expected insertion state of the insertion portion into the biliary tract, when the pushing-in operation of the insertion portion is performed with the distal end portion of the insertion portion arranged in the biliary tract as shown in FIG. 27.

Therefore, as shown in FIG. 29, in the endoscope 160 including, at the insertion portion 161, the connecting tube 165 which is made of rigid member and connects the bending portion 163 and the flexible tube portion 164 as shown in FIG. 29, there is a desire for an endoscope enabling the introduction of the insertion portion 161 into the biliary tract 110 to be easily performed.

Figure 30:
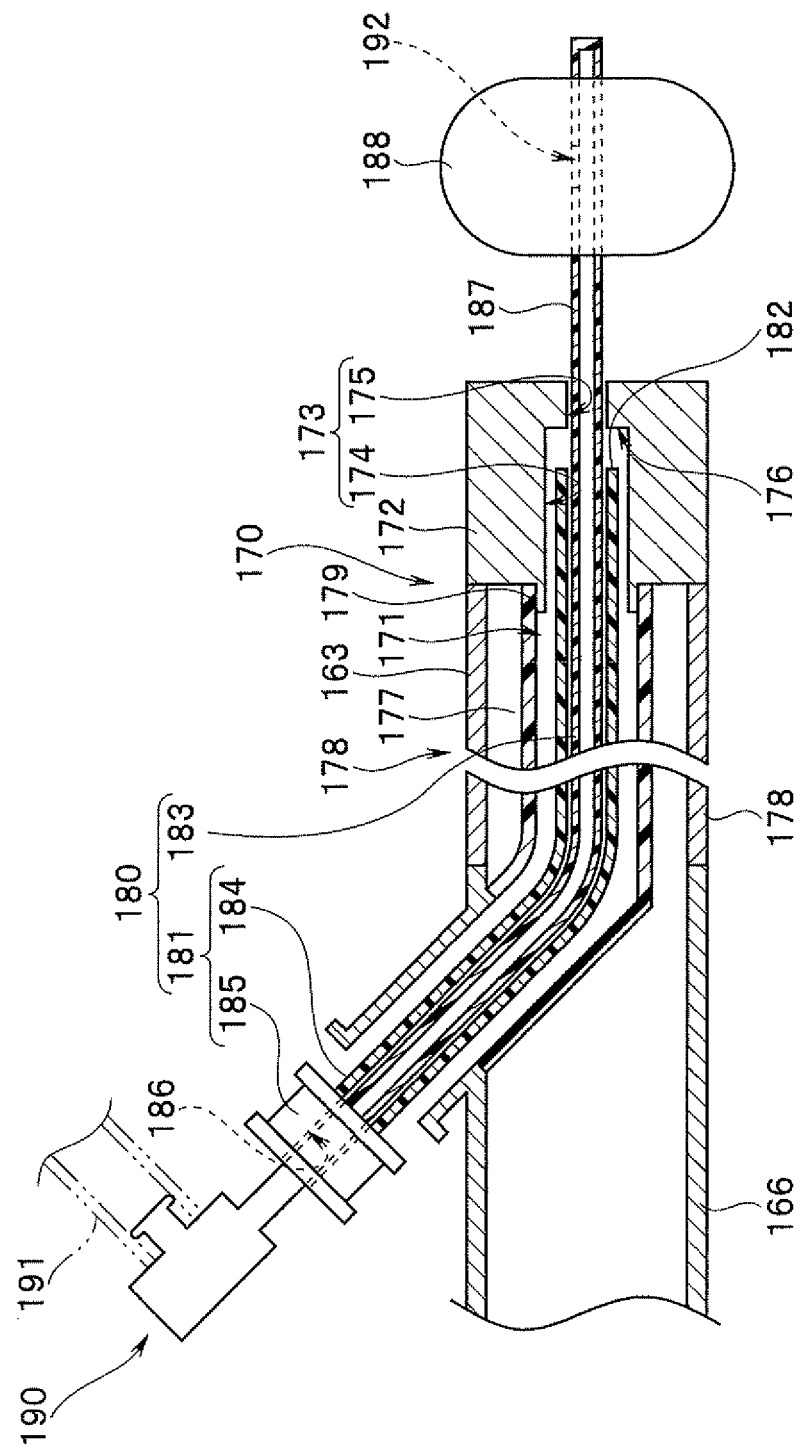
FIG. 30 is a view illustrating an endoscope system including: an endoscope having a treatment instrument channel; and an endoscope insertion assisting instrument configured to be inserted into the treatment instrument channel.
Figure 31:
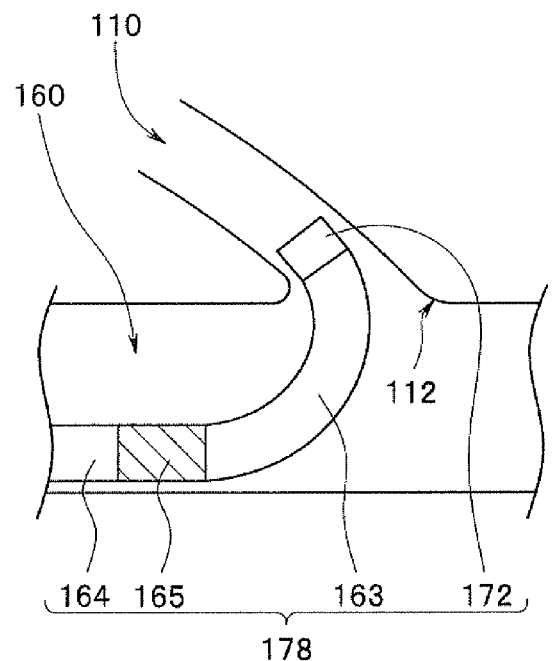
FIG. 31 to FIG. 34 relate to views illustrating a procedure for inserting the insertion portion of the endoscope into the biliary tract.
Figure 32:
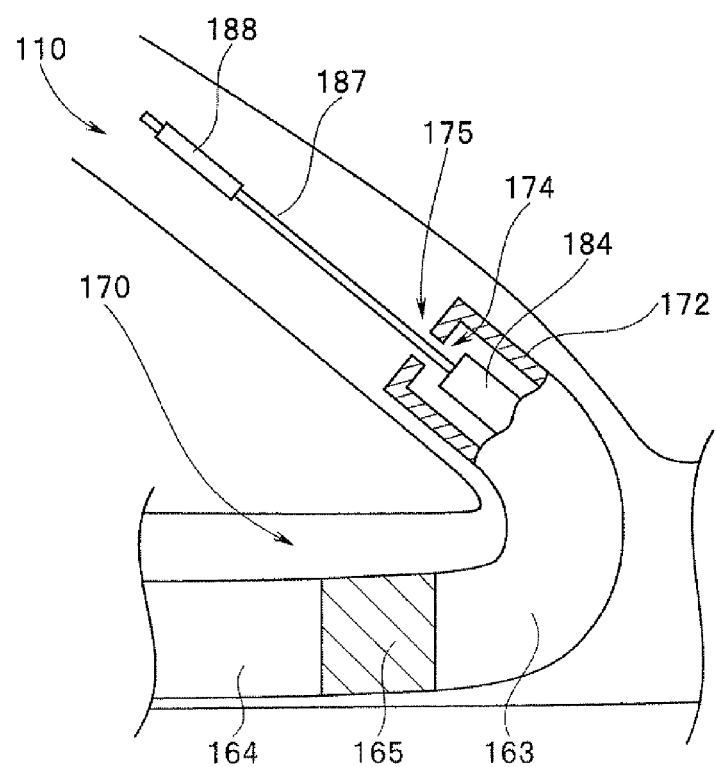
Figure 33:
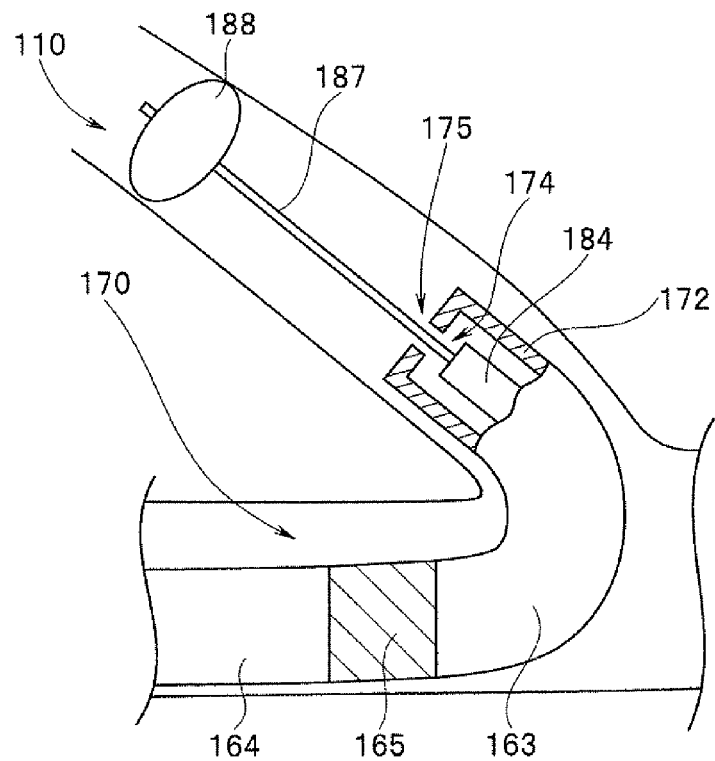
Figure 34:
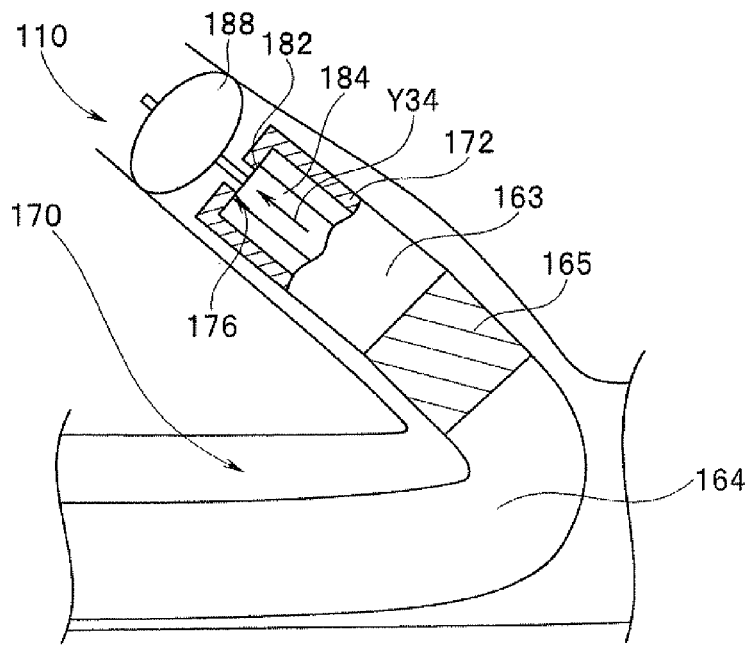
Figure 35A:
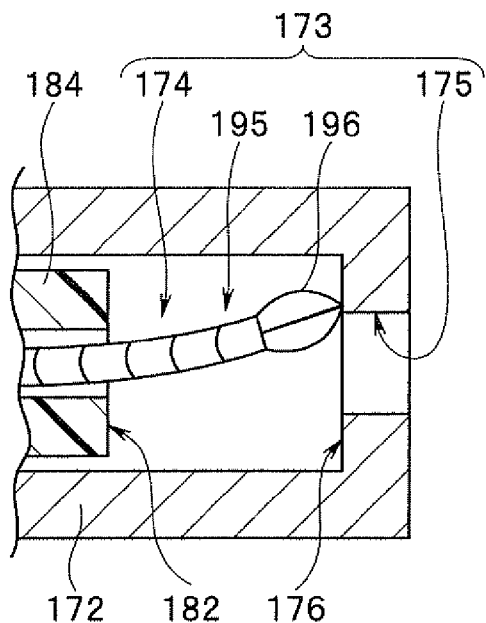
FIG. 35A is a view describing a problem of the treatment instrument in a state where the distal end surface of an outer tube is separated away from the abutting surface.
Figure 35B:
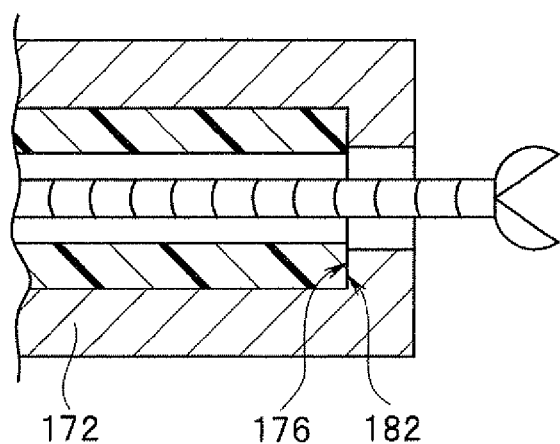
FIG. 35B is a view illustrating the treatment instrument which is smoothly led out from the treatment instrument outlet hole by causing the distal end surface of the outer tube to abut the abutting surface.

FIG. 30 is a view illustrating an endoscope system including: an endoscope having a treatment instrument channel; and an endoscope insertion assisting instrument configured to be inserted into the treatment instrument channel. FIG. 31 to FIG. 34 relate to views illustrating a procedure for inserting the insertion portion of the endoscope into the biliary tract in which: FIG. 31 is a view illustrating a state where the distal end portion of the insertion portion is inserted into the biliary tract; FIG. 32 is a view illustrating a state where a catheter main body is led out from a treatment instrument outlet hole of the endoscope into the biliary tract and a balloon in a deflated state is arranged at the deep part of the biliary tract; FIG. 33 is a view illustrating a state where the balloon inflated by sending air thereinto is retained at the deep part of the biliary tract; FIG. 34 is a view illustrating a state where the pushing-in operation of the insertion portion is performed with a distal end surface of a pusher tube being abutted an abutting surface of a channel hole and the insertion portion has been moved to the vicinity of the retained balloon; FIG. 35A is a view describing a problem of the treatment instrument in a state where the distal end surface of an outer tube is separated away from the abutting surface; and FIG. 35B is a view illustrating the treatment instrument which is smoothly led out from the treatment instrument outlet hole by causing the distal end surface of the outer tube to abut the abutting surface.

As shown in FIG. 30, the endoscope system according to the present embodiment includes an endoscope 170 and a balloon catheter with pusher which is an endoscope insertion assisting instrument (hereinafter, shortly referred to as catheter with pusher) 180. The endoscope 170 includes a treatment instrument channel 171. The catheter with pusher 180 is inserted in a treatment instrument channel 171.

The endoscope 170 includes a channel hole 173 configuring a treatment instrument channel 171 at a distal end portion 172 configuring the insertion portion distal end. The channel hole 173 according to the present embodiment includes a treatment instrument insertion hole 174 and a treatment instrument outlet hole 175.

The treatment instrument outlet hole 175 is a through hole which communicates the treatment instrument insertion hole 174 with outside. The inner diameter of the treatment instrument outlet hole 175 is smaller than the inner diameter of the treatment instrument insertion hole 174. Therefore, an abutting surface 176 configured by a plane is provided around the treatment instrument outlet hole 175. A distal end surface 182 of a pusher tube 181, to be described later, which configures the catheter with pusher 180, is arranged on the abutting surface 176 in an abutted manner.

The reference numeral 177 represents a treatment instrument channel tube and configures the treatment instrument channel 171. The distal end portion of the treatment instrument channel tube 177 is fixed to a connecting portion 179 provided at the distal end portion 172. The proximal end portion of the treatment instrument channel tube 177 is fixed to an operation portion 166. The reference numeral 163 represents a bending portion.

The catheter with pusher 180 includes a pusher tube 181 and a balloon catheter 183.

The pusher tube 181 includes an outer tube 184 having a through hole in an axis direction, and a tube-side grasping portion 185.

The outer tube 184 has an elasticity. The outer tube 184 is configured to be insertable in the treatment instrument channel 171. The tube-side grasping portion 185 is a ring-shaped member made of a rigid member, and includes a flange at both end portions. The tube-side grasping portion 185 includes at a center portion thereof a through hole 186 in the longitudinal direction. The end portion of the outer tube 184 communicates with one side opening of the through hole 186, to be fixed thereto.

The balloon catheter 183 includes a catheter main body 187, an inflatable/deflatable balloon 188, and a catheter-side grasping portion 190 having an air-sending port 189. The catheter main body 187 includes an axis direction through hole. The catheter main body 187 includes at the distal end side portion thereof a balloon 188 and includes at the proximal end side portion thereof the catheter-side grasping portion 190. The air-sending port 189 is connected with an air-sending tube 191 as shown by the two-dot chain lines.

The catheter main body 187 is configured to pass through the through hole 186 of the tube-side grasping portion 185, the through hole of the outer tube 184, and the treatment instrument outlet hole 175, to be protruded by a predetermined length from the distal end surface of the distal end portion 172.

In addition, the balloon 188 inflates by air, as a fluid, for example, sent thereinto through the air-sending tube 191. The air sent through the air-sending tube 191 is sent into the balloon 188 through the air-sending port 189, the through hole of the catheter main body 187, and an air-sending hole 192 formed at the catheter main body 187.

Note that, in the present embodiment, the inner diameter dimension of the through hole of the outer tube 184 is set to be smaller than the inner diameter dimension of the treatment instrument outlet hole 175 by a predetermined dimension.

Description will be made on the working of the endoscope system configured as described above.

In an insertion portion 178 of the endoscope 170, the proximal end side of the bending portion 163 and the distal end side of the flexible tube portion 164 are connected to each other with the connecting tube 165 made of a rigid member. In the procedure for inserting the insertion portion 178 into the biliary tract 110, the operator first causes the bending portion 163 to bend to insert the distal end portion 172 into the biliary tract 110 from the vicinity of the duodenal papilla 112, as shown in FIG. 31.

Next, the operator pushes the catheter-side grasping portion 190 with respect to the endoscope operation portion 166. Then, as shown in FIG. 32, the catheter main body 187 of the catheter with pusher 180 inserted in the treatment instrument channel 171 of the insertion portion 178 is led out in the biliary tract 110 through the treatment instrument outlet hole 175. After that, the operator moves the catheter-side grasping portion 190 until the catheter-side grasping portion abuts the tube-side grasping portion 185. As a result, as shown in the drawing, the balloon 188 which is in a deflated state is arranged at the deep part of the biliary tract 110.

Next, the operator sends air into the balloon 188 through the air-sending tube 191. Then, air is sent into the balloon 188, and the balloon 188 gradually inflates. Then, as shown in FIG. 33, the inflated balloon 188 is retained at the deep part of the biliary tract 110.

Next, the operator gives an instruction to an assistant, for example, to perform an operation for moving the pusher tube 181 forward. The distal end surface 182 of the pusher tube 181 which has been moved forward abuts the abutting surface 176, as shown in FIG. 34. When the pusher tube 181 is moved further forward in such an abutted state, a propulsive force for moving the insertion portion 178 in the direction of the arrow Y34 acts on the insertion portion.

The assistant performs the operation for moving the pusher tube 181 forward, while the operator performs a manual operation for moving the insertion portion 178 forward. Then, the insertion portion 178 moves forward toward the retained balloon 188. The distal end surface of the distal end portion 172 reaches the vicinity of the balloon 188, thereby causing the connecting tube 165 as a rigid portion to be arranged in the biliary tract 110.

After that, the operator performs, for example, the manual operation for moving the insertion portion 178 forward, to cause the distal end portion 172 to reach a target region. Then, the operator performs a suction of the air in the balloon 188 through the air-sending tube 191. Then the air is removed from the inflated balloon 188, which brings the balloon 188 into a deflated state.

When the balloon 188 is changed into a predetermined deflated state, the operator withdraws the balloon catheter 183 from the through hole of the outer tube 184. After that, the operator, when needed, leads out a treatment instrument such as grasping forceps into the biliary tract 110 from the distal end surface of the insertion portion 178, through the through hole 186 of the tube-side grasping portion 185, the through hole of the outer tube 184, and the treatment instrument outlet hole 175, to perform treatment and the like.

Note that, when the treatment instrument is led out into the biliary tract 110, the distal end surface 182 of the outer tube 184 is caused to abut the abutting surface 176. This prevents the state as shown in FIG. 35A in which the grasping portion 196 and the like of the grasping forceps 195 abuts the abutting surface 176 to interfere with the leading-out into the biliary tract 110. As a result, the grasping forceps 195 is smoothly led outside the channel as shown in FIG. 35B.

Thus, the endoscope system is configured by the endoscope having the abutting surface 176 in the channel hole 173 of the distal end portion 172, which configures the treatment instrument channel 171, and the catheter with pusher 180 including the pusher tube 181 and the balloon catheter 183 which are inserted in the treatment instrument channel 171. According to such a configuration, the catheter main body 187 of the balloon catheter 183 is led out in a body, and the balloon 188 is inflated to be retained in the body, and thereafter pushing-in operation is performed with the distal end surface 182 of the pusher tube 181 being abutted the abutting surface 176, thereby capable of applying to the insertion portion 178 a propulsive force for moving the insertion portion 178 in the distal end direction. As a result, the insertion portion 178 can be easily inserted into the biliary tract 110 and the like.

Note that the configuration of the endoscope insertion assisting instrument is not limited to the configuration described above, and may be configurations shown in FIGS. 36 to 41.

Figure 36:
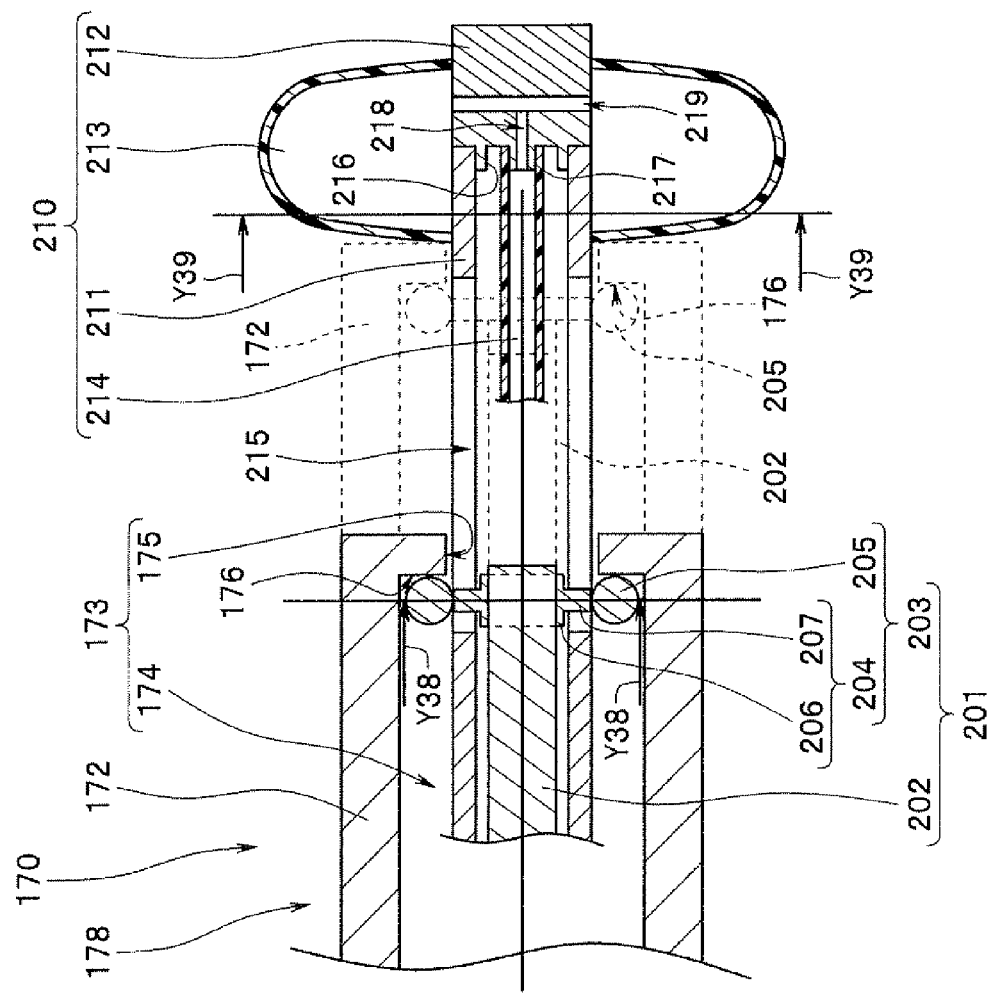
FIG. 36 to FIG. 41 relate to views illustrating other exemplary configurations of the endoscope insertion assisting instrument.
Figure 37:
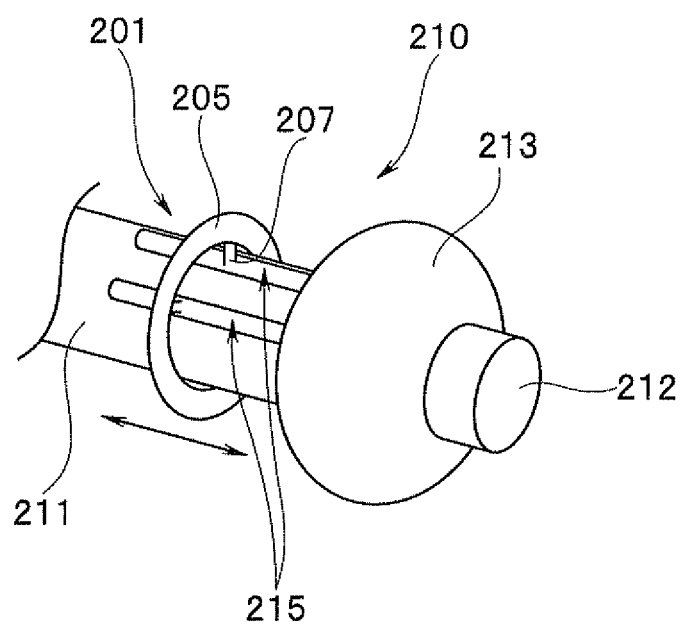
Figure 38:
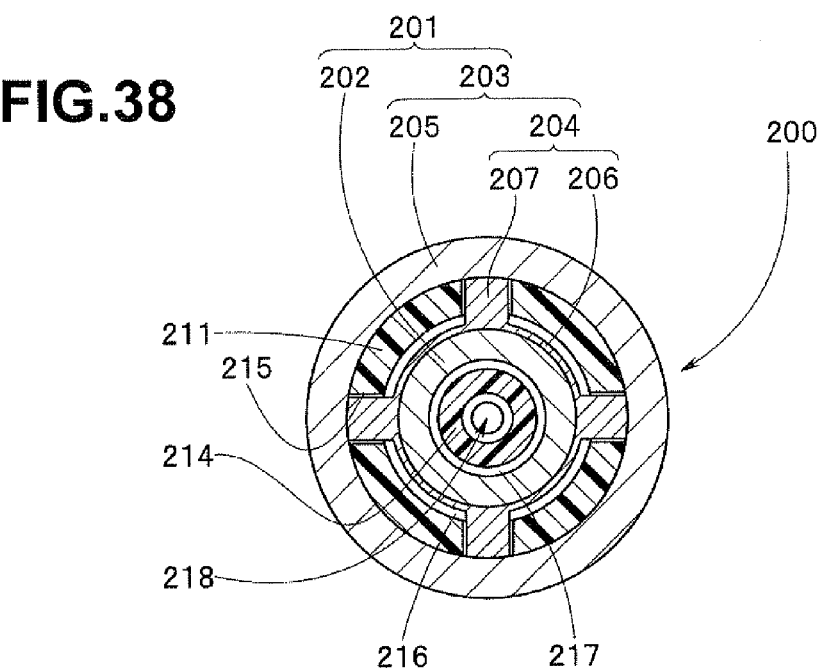
Figure 39:
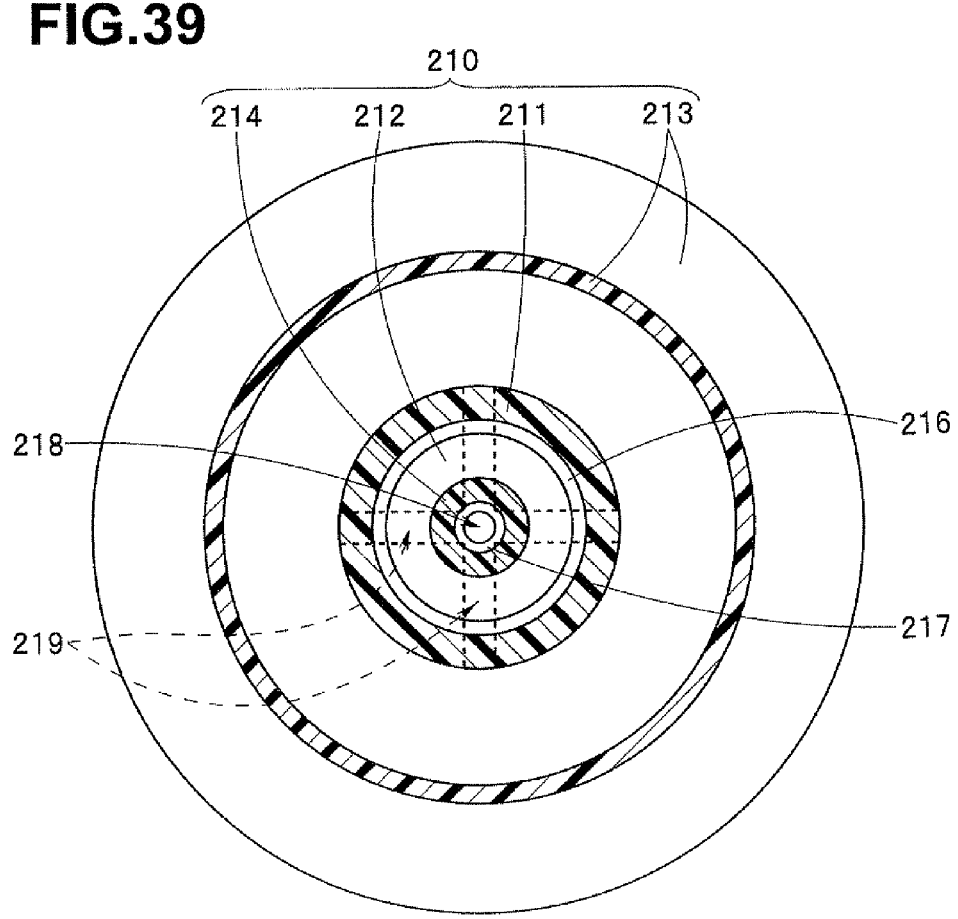
Figure 40:
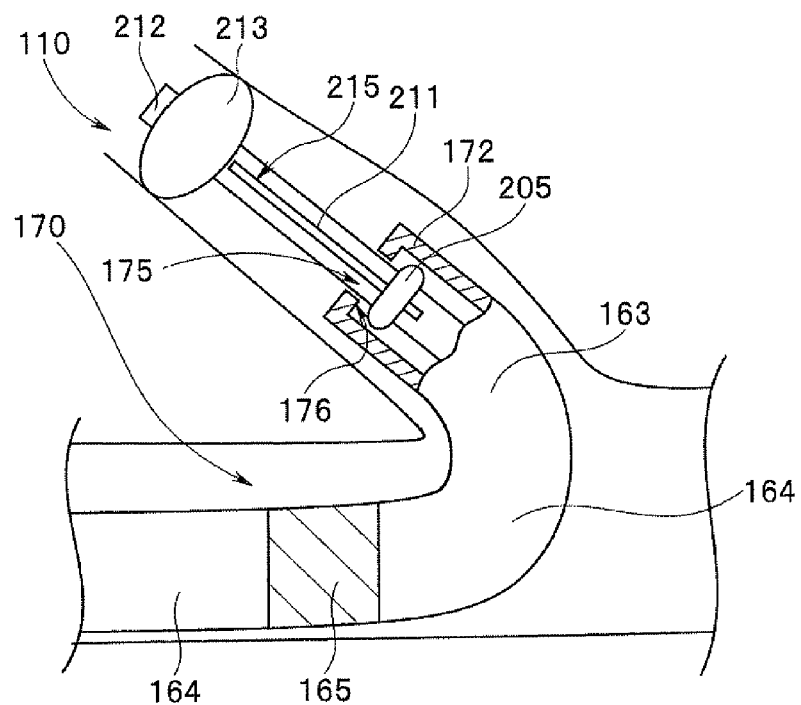
Figure 41:
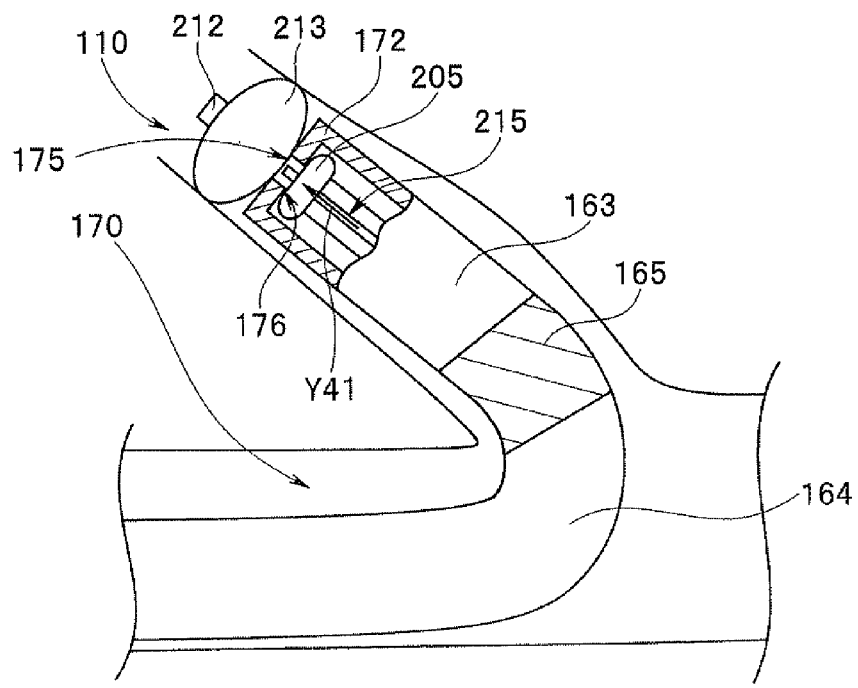

FIG. 36 to FIG. 41 relate to views illustrating other exemplary configurations of the endoscope insertion assisting instrument in which: FIG. 36 is a view illustrating another configuration of the endoscope insertion assisting instrument; FIG. 37 is a perspective view illustrating a configuration of a distal end portion of a balloon sheath; FIG. 38 is a cross-sectional view taken along the Y38-Y38 line shown by the arrows in FIG. 36; FIG. 39 is a cross-sectional view taken along the Y39-Y39 line shown by the arrows in FIG. 36; FIG. 40 is a view illustrating a state where air is sent into the balloon led out into the deep part of the biliary tract to retain the balloon at the deep part of the biliary tract; and FIG. 41 is a view illustrating a state where pushing-in operation is performed with a pressing ring of a pusher portion being abutted an abutting surface of a channel hole and the insertion portion has been moved to the vicinity of the retained balloon.

As shown in FIG. 36, the endoscope insertion assisting instrument according to the present embodiment is a catheter with pusher 200. The catheter with pusher 200 is inserted in the treatment instrument channel 171 of the endoscope 170. The catheter with pusher 200 includes a pusher portion 201 and a balloon catheter 210.

As shown in FIGS. 36 to 39, the pusher portion 201 includes an operation coil 202 and a pressing portion 203. The operation coil 202 includes a through hole in the axis direction. The pressing portion 203 is fixed to the distal end portion of the operation coil 202.

The pressing portion 203 includes a ring-shaped fixing member 204 and a pressing ring 205. The ring-shaped fixing member 204 is made of metal. The ring-shaped fixing member 204 includes a coil fixing ring 206 and four supporting poles 207, for example. The supporting poles 207 are radially erected from the ring 206 and arranged at intervals of 90 degrees in the circumferential direction.

The coil fixing ring 206 is arranged on the outer circumferential surface of the distal end portion of the operation coil 202, and integrally fixed thereto by adhesive bonding, welding, or the like. The pressing ring 205 is made of metal. The pressing ring 205 is arranged on the distal end surfaces of the respective supporting poles 207 and integrally fixed thereto by adhesive bonding, welding, or the like.

On the other hand, the balloon catheter 210 includes a sheath 211, a distal end cap 212, a balloon 213, and an air-sending tube 214. The sheath 211 is inserted in the treatment instrument channel 171.

The sheath 211 is a resin tube body having flexibility. Elongated slits 215 are formed in the axis direction at the distal end portion of the sheath 211. The supporting poles 207 are arranged so as to be advanceable and retractable in the slits 215. The length dimension of each of the slits 215 is set by taking the moving amount of the distal end portion 172 of the insertion portion 178 into consideration. That is, the operation coil 202 configuring the pusher portion 201 is caused to move forward with respect to the sheath 211 of the balloon catheter 210. Then, the supporting poles 207 of the pressing portion 203 move in the slits 215, thereby causing the pressing ring 205 to move forward.

The distal end cap 212 closes the distal end opening of the sheath 211. The distal end cap 212 is a cylindrical shape. The distal end cap 212 includes, on one surface side thereof, a sheath fixing projection portion 216 and an air-sending tube fixing projection portion 217. In addition, the distal end cap 212 includes an axis direction hole 218 as a flow passage and a perpendicular hole 219.

The axis direction hole 218 is formed around the longitudinal axis of the air-sending tube fixing projection portion 217 so as to have a predetermined depth dimension. On the other hand, the perpendicular hole 219 intersects the axis direction hole 218 at a right angle, and communicates the axis direction hole 218 with outside on the outer circumferential surface side of the distal end cap.

The balloon 213 is an inflatable/deflatable tube body. The distal end side of the balloon 213 is integrally fixed onto the outer circumferential surface of the distal end cap 212 and the proximal end side of the balloon 213 is integrally fixed onto the distal-end-side outer circumferential surface of the sheath 211.

The air-sending tube 214 is a tube body having a longitudinal direction through hole as a fluid passage. The distal end portion of the air-sending tube 214 is arranged on the outer circumferential surface of the air-sending tube fixing projection portion 217 and integrally fixed thereto by adhesive bonding, for example. The proximal end side of the air-sending tube 214 passes through the through hole of the operation coil 202 to be connected to the air-sending port 189.

Note that, the distal end portion of the sheath 211 is arranged on the outer circumferential surface of the sheath fixing projection portion 216 and integrally fixed thereto by adhesive bonding, for example.

Description will be made on the working of the endoscope system including the catheter with pusher 200 configured as described above.

In the procedure for inserting the insertion portion 178 of the endoscope 170 into the biliary tract 110, the operator causes the bending portion 163 to bend to insert the distal end portion 172 from the vicinity of the duodenal papilla 112 into the biliary tract 110, as shown in FIG. 31.

Next, the operator leads out the balloon catheter 210 of the catheter 200 with pusher, which is inserted in the treatment instrument channel 171 of the insertion portion 178, into the biliary tract 110 through the treatment instrument outlet hole 175, as shown in FIG. 40. The operator arranges the balloon 213 in the deflated state at the deep part of the biliary tract 110.

Next, the operator sends air into the balloon 213 through the air-sending tube 214. Then, air is sent into the balloon 213, and thereby the balloon 213 gradually inflates to be retained at the deep part of the biliary tract.

Next, the operator gives an instruction to an assistant to perform an operation for moving the pusher portion 201 forward, for example. The pressing ring 205 configuring the pusher portion 201 which has been moved forward abuts the abutting surface 176 around the treatment instrument outlet hole 175. When the pusher portion 201 is moved further forward in such an abutted state, a propulsive force for moving the insertion portion 178 in the direction of the arrow Y41 acts on the insertion portion, as shown in FIG. 41.

The assistant performs the operation for moving the pusher portion 201 forward, while the operator performs manual operation for moving the insertion portion 178 forward. Then, the insertion portion 178 moves forward toward the retained balloon 213. The distal end surface of the distal end portion 172 reaches the vicinity of the balloon 213, and thereby the connecting tube 165 as a rigid portion is arranged in the biliary tract 110.

After that, the operator causes the distal end portion 172 of the insertion portion 178 to reach the target region as described above. Then, the operator causes the balloon 213 to be changed into a deflated state, and withdraws the catheter with pusher 200 from the treatment instrument channel 171. After that, the operator, when needed, leads out the treatment instrument into the biliary tract 110 through the treatment instrument channel 171, to perform treatment and the like.

Thus, the endoscope system is configured by the endoscope having the abutting surface 176 in the channel hole 173 of the distal end portion 172, which configures the treatment instrument channel 171, and the catheter with pusher 200 including the pusher portion 201 and the balloon catheter 210 which are inserted in the treatment instrument channel 171. According to such a configuration, the balloon catheter 210 is led out in a body, and the balloon 213 is inflated to be retained in the body, and thereafter pushing-in operation is performed with the pressing ring 205 of the pusher portion 201 being abutted the abutting surface 176, thereby capable of applying to the insertion portion 178 a propulsive force for moving the insertion portion 178 in the distal end direction. As a result, the insertion portion 178 can be easily inserted into the biliary tract 110 and the like.

Incidentally, in recent years, a procedure for inserting a small-diameter front-view endoscope into a biliary tract using a balloon catheter as a guide has been proposed. In this procedure, when inserting a front-view endoscope into the biliary tract, first, endoscopic sphincterotomy, what is called EST, for dissecting a duodenal papilla sphincter is performed by using a high-frequency dissection instrument for endoscope. Next, the balloon catheter is inserted into a biliary tract to retain the balloon at the deep part of the biliary tract. Then, the insertion portion of the front-view endoscope is pushed forward to the deep part of the biliary tract where the balloon is retained by using the balloon catheter as a guide.

However, a high-frequency dissection instrument for endoscope is generally designed on the assumption that such an instrument is used with a lateral-view endoscope having a raising stand. Therefore, when performing EST by inserting the high-frequency dissection instrument for endoscope into a treatment instrument channel of a front-view endoscope, the operator may have a difficulty in performing EST as he or she desires. Therefore, there is a desire for a high-frequency dissection instrument for front-view endoscope which is optimal to be used in a front-view endoscope.

Figure 42:
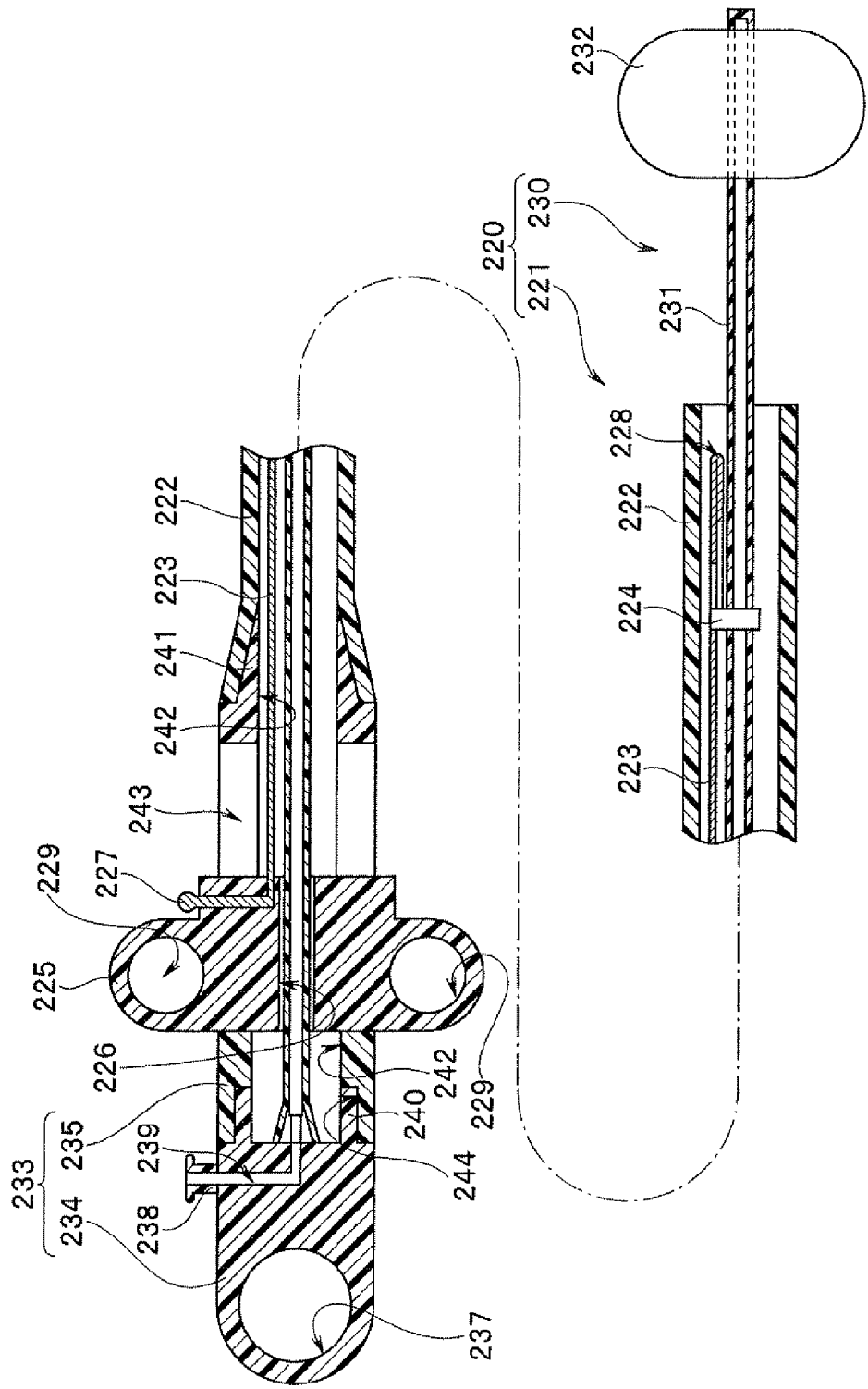
Figure 43:
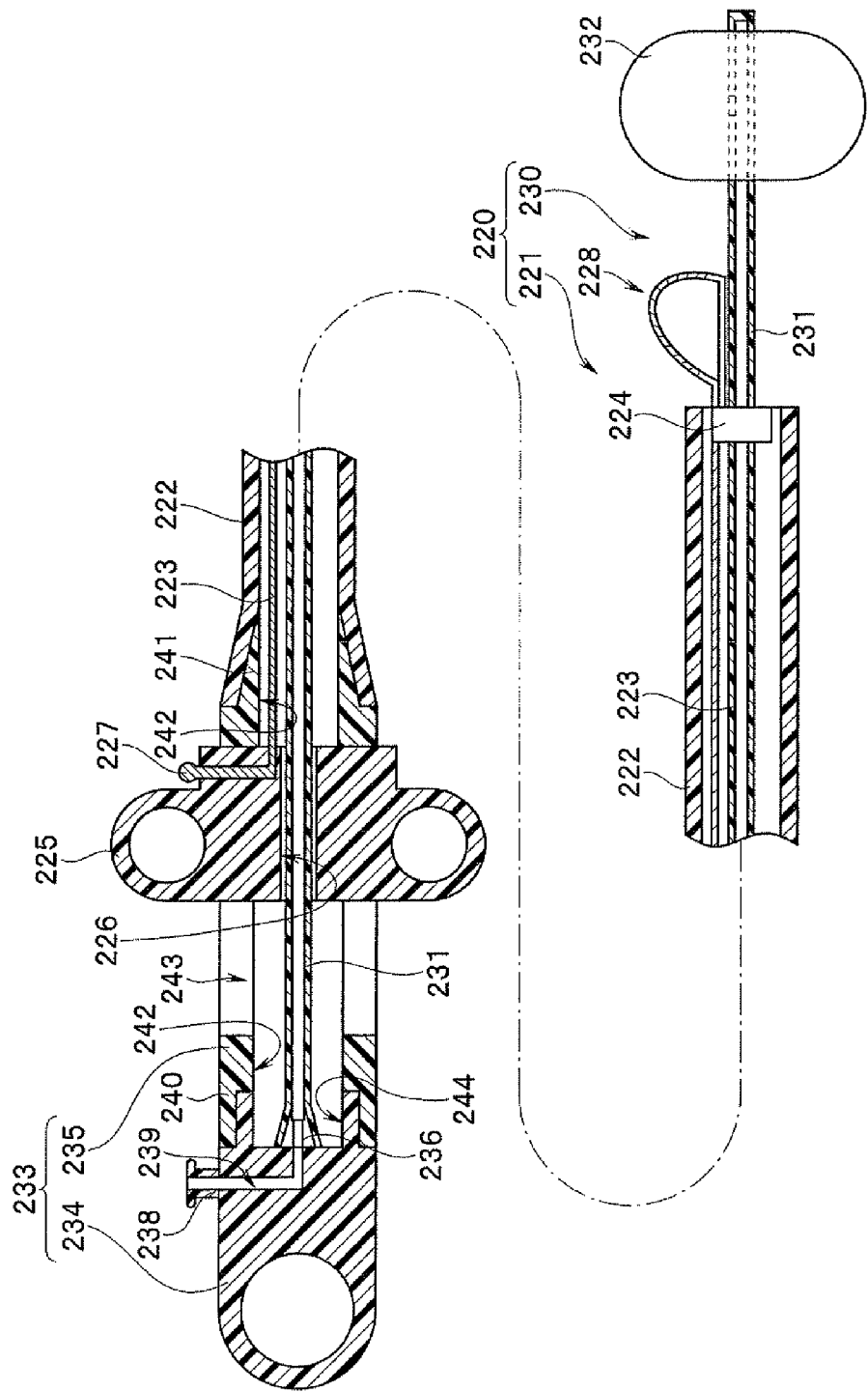
Figure 44A:
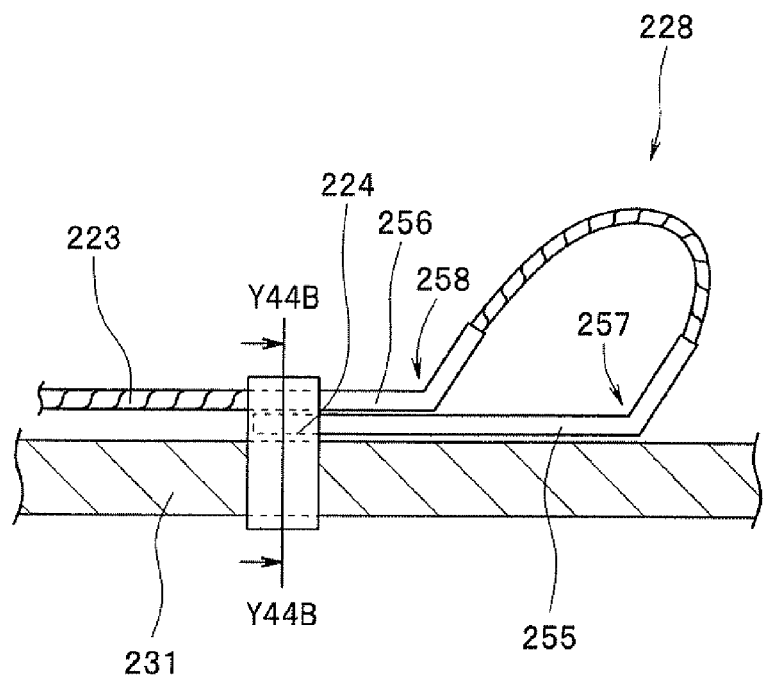
FIG. 44A is a view illustrating a configuration of the knife portion.
Figure 44B:
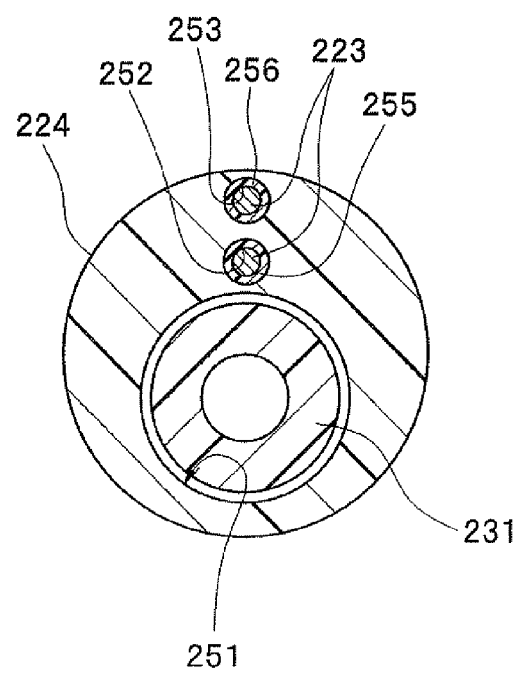
FIG. 44B is a cross-sectional view taken along the Y44B-Y44B line shown by the arrows in FIG. 44A.
Figure 45A:
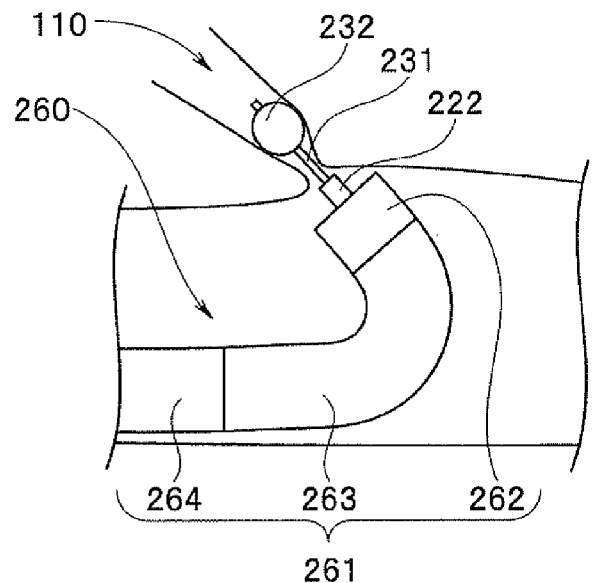
Figure 45B:
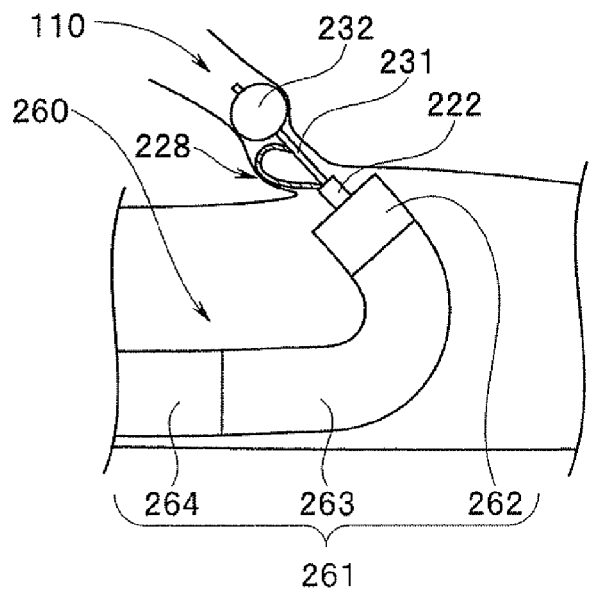
Figure 45C:
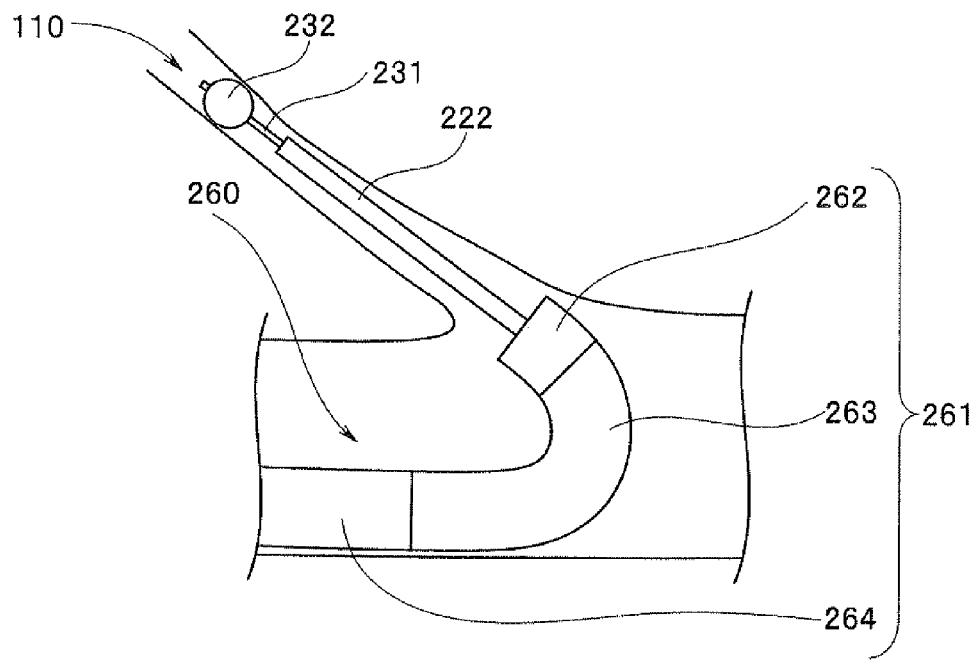
Figure 45D:
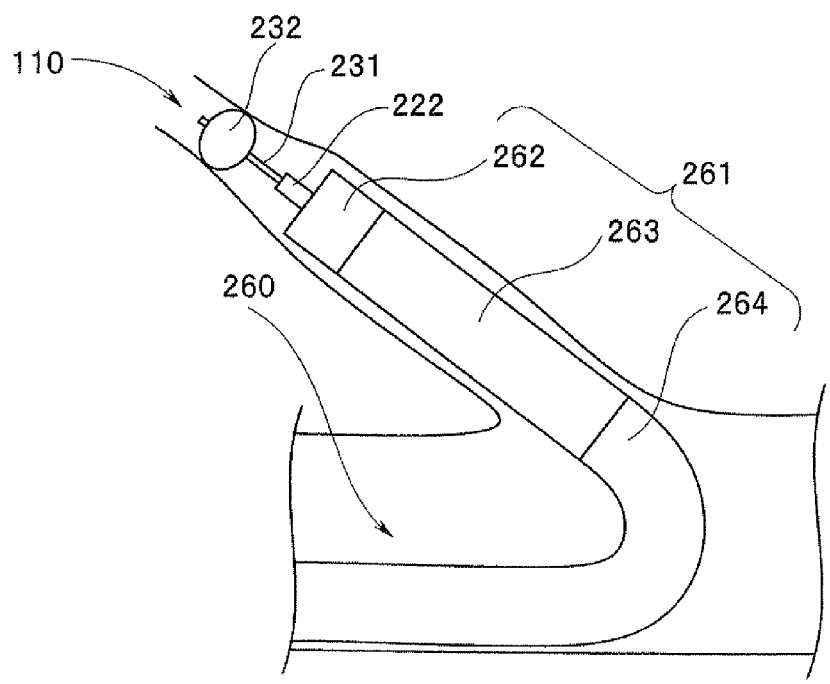

FIGS. 42 to 45D relate to views illustrating configurations and workings of a high-frequency dissection instrument for front-view endoscope in which: FIG. 42 is a view illustrating the high-frequency dissection instrument for front-view endoscope which includes a high-frequency dissection portion, a balloon catheter portion, and a knife portion housed in an outer-layer sheath; FIG. 43 is a view illustrating a high-frequency dissection instrument for front-view endoscope having a knife portion protruded outside of the outer-layer sheath; FIG. 44A is a view illustrating the configuration of the knife portion; and FIG. 44B is a cross-sectional view taken along the Y44B-Y44B line shown by the arrows in FIG. 44A. FIGS. 45A to 45D relate to views illustrating the workings of the high-frequency dissection instrument for front-view endoscope in which: FIG. 45A is a view illustrating a state where the bending portion of the endoscope insertion portion is bent, the distal end portion is caused to face the orifice portion of the biliary tract, the balloon sheath is inserted in the biliary tract, and thereafter the balloon is retained in the biliary tract; FIG. 45B is a view illustrating EST performed with the balloon retained in the biliary tract; FIG. 45C is a view illustrating the state where, after the EST is finished, the balloon sheath is inserted into the deep part of the biliary tract and the balloon is retained at the deep part of the biliary tract; and FIG. 45D is a view illustrating the endoscope insertion portion to be inserted by using the balloon sheath as a guide, with the balloon retained at the deep part of the biliary tract.

As shown in FIGS. 42 and 43, a high-frequency dissection instrument for front-view endoscope (hereinafter, shortly referred to as front-view high frequency knife) 220 includes a high-frequency dissection portion 221 and a balloon catheter portion 230.

The high-frequency dissection portion 221 is configured by mainly including an outer-layer sheath 222, an operation wire 223, a sliding ring 224, and a slider 225. The operation wire 223 serves also as a knife portion.

On the other hand, the balloon catheter portion 230 is mainly configured by a balloon sheath 231, a balloon 232, and an operation portion main body 233. The operation portion main body 233 has a two-body structure, for example. The operation portion main body 233 includes a balloon constituting part (hereinafter referred to as a first constituting part) 234, and a knife constituting part (hereinafter, referred to as a second constituting part) 235.

The balloon sheath 231 is a tube body having flexibility. The balloon sheath 231 is inserted in a through hole included in the outer-layer sheath 222. At the distal end portion of the balloon sheath 231, the balloon 232 is fixed so as to be inflatable/deflatable. On the other hand, the proximal end portion of the balloon sheath 231 is integrally fixed to a balloon sheath base 236 formed at the first constituting part 234. The balloon sheath 231 passes through a balloon sheath insertion hole 226 formed at the slider 225 to reach the first constituting part 234.

The first constituting part 234 includes, in addition to the balloon sheath base 236, an operation hole 237, an air-sending port 238, a fluid passage 239 and an engagement projection portion 240.

The operation hole 237 is a finger-hooking hole on which the thumb of the operator is placed, for example. The air-sending port 238 is a connecting port to which an air-sending tube extended from the air-sending apparatus (not shown) is connected.

The fluid path 239 is a conduit which communicates the air-sending port 238 with the balloon sheath base 236. Air sent from the air-sending apparatus through the air-sending tube is supplied to the balloon sheath 231 through the fluid path 239.

The engagement projection portion 240 is an engagement portion with the second constituting part 235. The engagement projection portion 240 is arranged in the engagement recessed portion, to be described later, of the second constituting part 235.

The outer-layer sheath 222 of the high-frequency dissection portion 221 is a flexible sheath having electric insulation properties. The high-frequency dissection portion 221 is introduced into a body through the treatment instrument channel of the endoscope. The length dimension of the outer-layer sheath 222 is made to be shorter than the length of the balloon sheath 231 by a predetermined dimension. As a result, the distal end side portion of the balloon sheath 231 where the balloon 232 is provided protrudes from the distal end surface of the outer-layer sheath 222 by a predetermined distance.

The proximal end portion of the outer-layer sheath 222 is integrally attached to an outer-layer sheath base 241. The outer-layer sheath base 241 is formed at the second constituting part 235.

At the second constituting part 235, a balloon sheath insertion hole 242, a slider slit 243, and an engagement recessed portion 244 are formed, in addition to the outer-layer sheath base 241.

The balloon sheath insertion hole 242 is a through hole in which the balloon sheath 231 is inserted and arranged. The slider slit 243 forms an elongated slider sliding space in the longitudinal axis direction. The slider 225 is slidably arranged in the longitudinal axis direction in the slider slit 243.

The engagement recessed portion 244 is an engagement portion with the first constituting part 234, with which the engagement projection portion 240 of the first constituting part 234 is engaged.

Note that the first constituting part 234 and the second constituting part 235 are fixed integrally with each other in a state where the engagement projection portion 240 is engaged with the engagement recessed portion 244, to configure the operation portion main body 233. In addition, the first constituting part 234 and the second constituting part 235 are made of resin having insulation properties, for example.

The operation wire 223 is a conductive member and has a predetermined elasticity. The proximal end portion of the operation wire 223 is electrically connected to the electric connection portion 227 provided at the slider 225. The electric connection portion 227 is connected with a high-frequency power supply cable (not shown) extended from a high-frequency power supply apparatus (not shown). High-frequency current supplied from the high-frequency power supply apparatus is conducted to the operation wire 223 through a high-frequency power supply cable, and the electric connection portion 227.

The distal end portion of the operation wire 223 is slidably arranged in a gap between the inner surface of the outer-layer sheath 222 and the outer surface of the balloon sheath 231, to be led out to the distal end side. The distal end portion of the operation wire 223 is folded back to form a knife portion 228, and fixed to the sliding ring 224.

The sliding ring 224 is a ring-shaped member and slidably arranged in the through hole of the outer-layer sheath 222.

As shown in FIGS. 44A and 44B, the sliding ring 224 includes a balloon sheath insertion hole 251, and operation wire fixing holes 252, 253. The centers of the holes 251, 252 and 253 and the center of the sliding ring 224 are arranged on a straight line. The second operation wire fixing hole 253 is formed so as to be located closest to the outer circumferential surface of the sliding ring 224.

The balloon sheath insertion hole 251 is a through hole for allowing the balloon sheath 231 to insert therethrough. The inner diameter of the balloon sheath insertion hole 251 is lager than the outer diameter of the balloon sheath 231 by a predetermined dimension. That is, the sliding ring 224 is slidable also with respect to the balloon sheath 231.

Inside the operation wire fixing holes 252, 253, insulating tubes 255, 256 for covering and wrapping the operation wire 223 are fixedly provided. Specifically, the first insulating tube 255 and the distal end portion of the operation wire 223 which is covered with the tube 255 are fixed to the first operation wire fixing hole 252.

On the other hand, the second insulating tube 256 and the middle portion of the operation wire 223 which is covered with the tube 256 are fixed to the second operation wire fixing hole 253.

The first insulating tube 255 and the second insulating tube 256 are knife forming members which cause the distal end side of the operation wire 223 to form the knife portion 228. The first insulating tube 255 and the second insulating tube 256 are made of an insulating member having a predetermined elasticity and set to a predetermined length dimension.

The length of the first insulating tube 255 is set to be longer than the length of the second insulating tube 256. The respective tubes 255, 256 include folded parts 257, 258 to which folding tendencies of predetermined shapes are given.

The sliding ring 224 is fixed to a predetermined position of the operation wire 223.

As shown in FIG. 42, when the slider 225 is located on the proximal end side of the slit 243, the sliding ring 224 is arranged on the inner side than the distal end surface of the outer-layer sheath 222 by a predetermined distance. In this arrangement position, the first insulating tube 255 and the second insulating tube 256 are both housed in the outer-layer sheath 222. Therefore, the knife portion 228 is folded and housed in the outer-layer sheath 222.

In contrast, when the slider 225 is moved to the distal end side of the slit 243, also the sliding ring 224 is moved in the distal end direction. Then, as shown in FIG. 43, when the distal end surface of the outer-layer sheath 222 surface-coincides with the distal end surface of the sliding ring 224, for example, both the first insulating tube 255 and the second insulating tube 256 are exposed outside from the distal end surface of the outer-layer sheath 222.

Then, the folded parts 257, 258 of the insulating tubes 255, 256 deform into the predetermined shapes. As a result, the folded operation wire 223 is deformed to form the knife portion 228 in an expanded shape on the distal end side. The shapes of the folded parts 257, 258 and the size of the knife portion 228 are set such that the distal end of the knife portion 228 is arranged spaced apart from the hand side of the inflated balloon 232 by a predetermined distance at this time.

Note that the reference numeral 229 represents a finger-hooking hole. On the finger-hooking hole 229, an index finger and a middle finger, or a medicinal finger and a little finger of the operator are hooked, for example.

With reference to FIGS. 45A to 45D, the working of the front-view high-frequency knife 220 as described above will be described.

An insertion portion 261 of a front-view endoscope 260 includes in the following order from the distal end side: a distal end portion 262, a bending portion 263, and a flexible tube portion 264 in a linked manner.

In the procedure for inserting the insertion portion 261 into the biliary tract 110, the operator first bends the bending portion 263 to cause the distal end surface of the distal end portion 262 to face the orifice portion of the biliary tract, as shown in FIG. 45A. After that, the operator inserts the front-view high-frequency knife 220 from the distal end opening of the treatment instrument channel into the biliary tract 110, while observing the endoscopic image displayed on the screen of the display apparatus.

Then, when confirming on the endoscopic observation image that the distal end surface of the outer-layer sheath 222 of the front-view high-frequency knife 220 is arranged at a desired position with respect to the orifice portion of the biliary tract, the operator stops the insertion into the biliary tract 110. Then, the operator sends air into the balloon 232 through an air-sending tube, not shown, to inflate the balloon 232 and retain the balloon 232 in the biliary tract 110.

Next, the operator moves the slider 225 to the distal end side of the slit 243 in order to perform EST. Then, as shown in FIG. 45B, the knife portion 228 is fowled in front of the distal end surface of the outer-layer sheath 222. At this time, since high-frequency current is supplied from the high-frequency power supply apparatus to the operation wire 223, the operator can perform EST. Since the inflated balloon 232 is retained in the biliary tract 110 at this time, EST can be stably performed, which enables excellent dissection.

After EST is finished, the operator moves the slider 225 to the proximal end side of the slit 243 to house the knife portion 228 in the outer-layer sheath 222 and deflates the balloon 232 once. After that, the operator inserts the front-view high-frequency knife 220 into the deep part of the biliary tract 110.

After the insertion into the deep part is finished, the operator inflates the balloon 232 again to retain the balloon at the deep part of the biliary tract, as shown in FIG. 45C.

Next, the operator pushes the insertion portion 261 of the front-view endoscope 260 toward the deep part of the biliary tract where the balloon 232 is retained, by using the balloon sheath 231 as a guide, as shown in FIG. 45D.

The front-view high-frequency knife 220 including the high-frequency dissection portion 221 and the balloon catheter portion 230 is thus configured. According to this configuration, EST and introduction of the insertion portion 261 of the front-view endoscope 260 into the deep part of the biliary tract can be performed without exchanging the front-view high-frequency knife 220 inserted in the treatment instrument channel.

Figure 46:
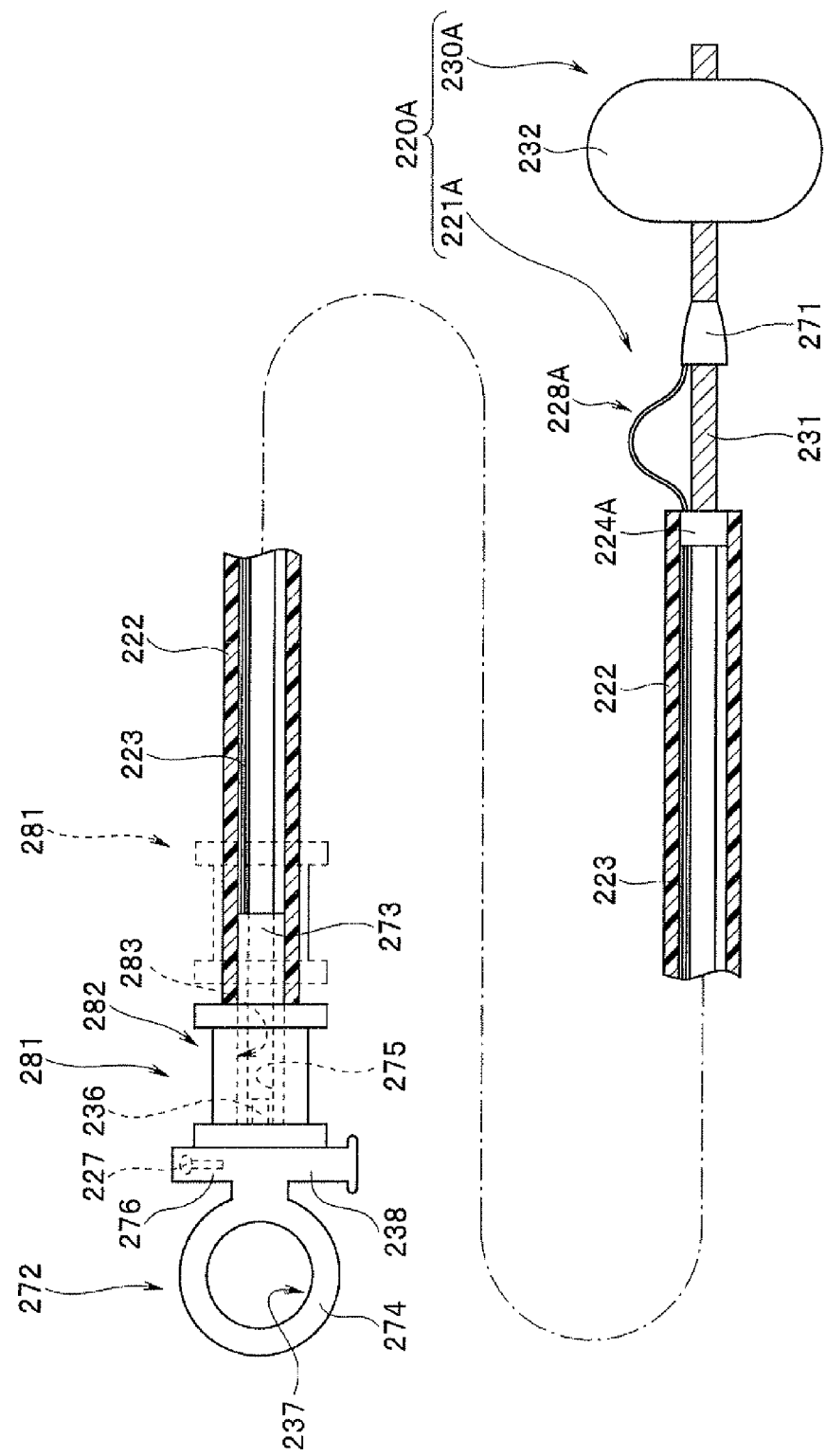
Figure 47:
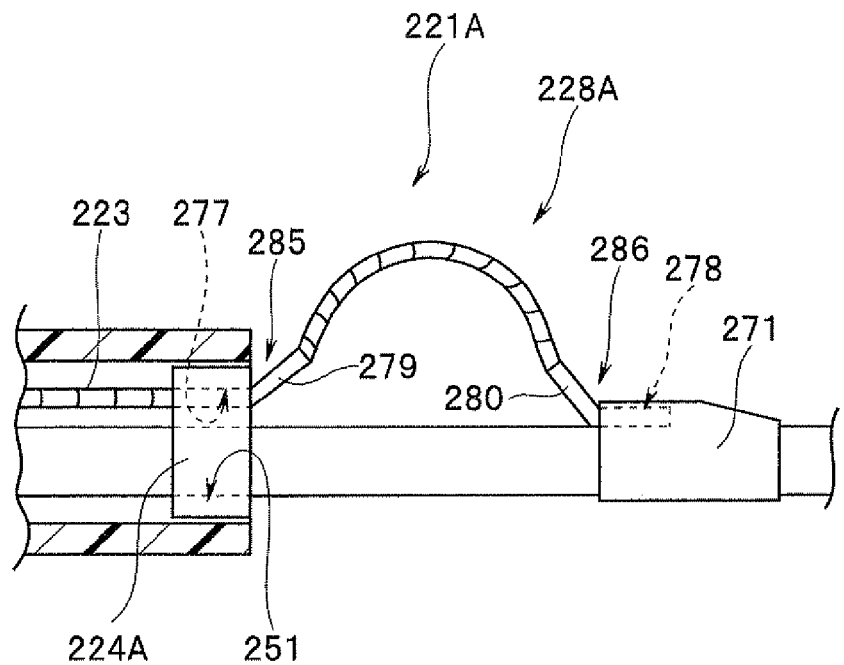
Figure 48:
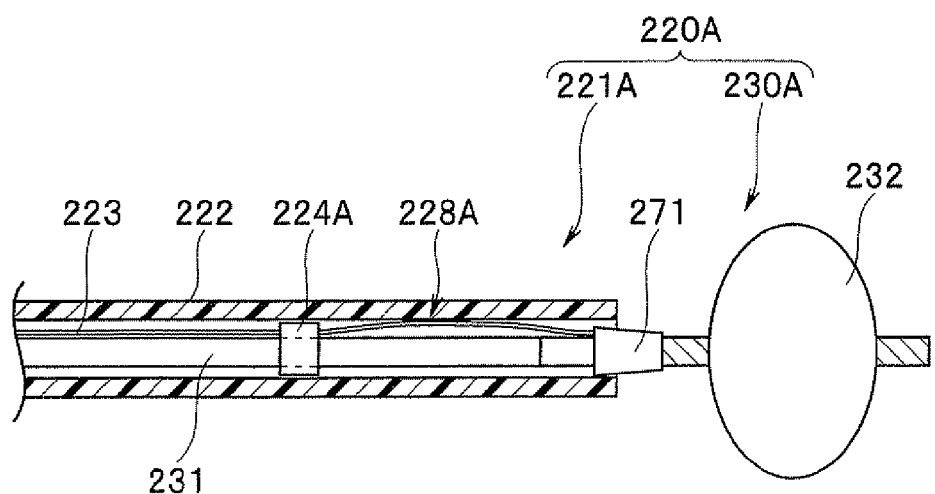

Note that the configuration of the front-view high-frequency knife is not limited to the above-described configuration and may be the configurations shown in FIGS. 46 to 48.

Figure 49A:
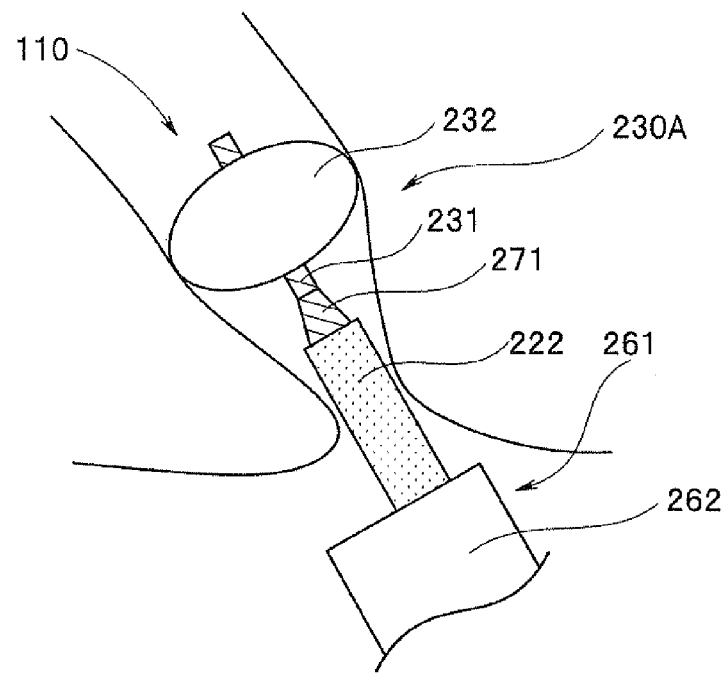
Figure 49B:
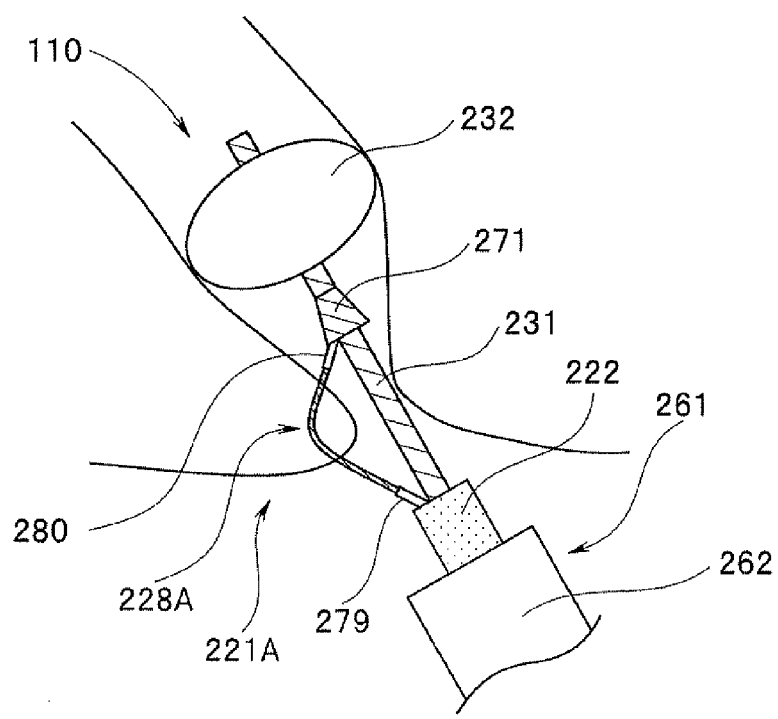

FIG. 46 to FIG. 49B relate to views illustrating other exemplary configurations and workings of the high-frequency dissection instrument for front-view endoscope. FIG. 46 is a view illustrating the high-frequency dissection instrument for front-view endoscope having another configuration, FIG. 47 is a view illustrating a configuration of the knife portion, and FIG. 48 is a view illustrating a state where the knife portion is housed in the outer-layer sheath. FIG. 49A and FIG. 49B relate to views illustrating the workings of the high-frequency knife for front-view endoscope, in which FIG. 49A is a view illustrating a positional relationship between the balloon and the outer-layer sheath when the balloon is retained in the biliary tract, and FIG. 49B is a view illustrating the EST performed with the balloon retained in the biliary tract.

As shown in FIG. 46, a front-view high-frequency knife 220A includes a high-frequency dissection portion 221A and a balloon catheter portion 230A.

The high-frequency dissection portion 221A is configured by mainly including the outer-layer sheath 222, the operation wire 223, a sliding ring 224A, a fixing ring 271A, and a slider 272. The operation wire 223 also serves as a knife portion. On the other hand, the balloon catheter portion 230A is configured by mainly including the balloon sheath 231, the balloon 232, and an operation portion main body 281.

The slider 272 according to the present embodiment is configured by including a shaft portion 273 and a ring portion 274. The ring portion 274 includes the operation hole 237. The shaft portion 273 includes a sheath arranging hole 275 and a wire insertion hole (not shown). The operation wire 223 is inserted through the wire insertion hole. The balloon sheath 231 is inserted and arranged in the sheath arranging hole 275. The sheath arranging hole 275 is a hole having a bottom surface. The balloon sheath base 236 to which the proximal end portion of the balloon sheath 231 is fixed is provided on the bottom surface of the sheath arranging hole 275.

On the side surfaces of the shaft portion 273, a first protrusion 276 to which the electric connection portion 227 is provided, and the air-sending port 238 as a second protrusion are provided. The operation wire 223 inserted in the wire insertion hole is electrically connected to the electric connection portion 227 disposed at the first protrusion 276.

The operation portion main body 281 is a ring-shaped member made of insulating member. Each of a pair of flanges is provided on both end portions of the operation portion main body 281. A groove 282 between the flanges of the operation portion main body 281 is a finger-hooking portion on which the index finger, the middle finger or the like of the operator is hooked.

The operation portion main body 281 includes a shaft insertion hole 283 which penetrates in the longitudinal axis direction. The shaft portion 273 is slidably arranged in the shaft insertion hole 283. The operation portion main body 281 includes an outer-layer base (not shown). The proximal end portion of the outer-layer sheath 222 is fixed to the outer-layer base.

The distal end portion of the operation wire 223 whose proximal end portion is fixed to the electric connection portion 227 is slidably arranged in a gap between the inner surface of the outer-layer sheath 222 and the outer surface of the balloon sheath 231 to be led out to the distal end side.

As shown in FIG. 47, the distal end portion of the operation wire 223 according to the present embodiment is fixed inside of a wire fixing hole 278 provided to the fixing ring 271. The operation wire 223 passes through the operation wire fixing hole 277 of the sliding ring 224A to reach inside of the wire fixing hole 278.

The sliding ring 224A of the present embodiment includes the balloon sheath insertion hole 251 and the operation wire fixing hole 277. The centers of the holes 241 and 277 and the center of the sliding ring 224A are arranged on a straight line.

Inside the operation wire fixing hole 277, the second insulating tube 279 and the middle portion of the operation wire 223 are fixed. The second insulating tube 279 covers and wraps the operation wire 223, and the operation wire 223 is covered with the tube 279. The first insulating tube 280 and the distal end portion of the operation wire 223 which is covered with the tube 280 are fixed to the wire fixing hole 278.

The first insulating tube 280 and the second insulating tube 279 are knife forming members which cause the distal end side of the operation wire 223 to form the knife portion 228A. The first insulating tube 280 and the second insulating tube 279 are made of an insulating member having a predetermined elasticity and set to a predetermined length dimension. The respective tubes 279, 280 include folded parts 285, 286 to which folding tendencies of predetermined shapes are given.

The sliding ring 224A is fixed to a predetermined position of the operation wire 223.

In the present embodiment, when the slider 272 and the operation portion main body 281 are brought into contact with each other, as shown by the solid lines in FIG. 46, the distal end surface of the outer-layer sheath 222 and the distal end surface of the sliding ring 224A surface-coincide with each other.

At this time, the fixing ring 271, the first insulating tube 280 and the second insulating tube 279 are exposed outside from the distal end surface of the outer-layer sheath 222. As a result, the folded parts 285, 286 of the insulating tubes 280, 279 respectively deform into the predetermined shapes, thereby forming the knife portion 228 in an expanded shape on the distal end side of the wire.

On the other hand, in the initial state in which the operation portion main body 281 is arranged at the position shown by the dashed lines in FIG. 46 and the operation portion main body 281 and the slider 272 are separated from each other, the sliding ring 224A is arranged on the inner side than the distal end surface of the outer-layer sheath 222 by a predetermined distance, as shown in FIG. 48.

At this time, the sliding ring 224A, the first insulating tube 280 and the second insulating tube 279 are housed in the outer-layer sheath 222, and the proximal end portion of the fixing ring 271 is arranged in the distal end portion of the outer-layer sheath 222. As a result, the knife portion 228A is housed in the outer-layer sheath 222 in a linear state without being folded.

With reference to FIGS. 49A, 49B, description will be made on the working of the front-view high-frequency knife 220A configured as described above.

In the procedure for inserting the insertion portion 261 of the front-view endoscope 260 into the biliary tract 110, the operator causes the bending portion 263 to bend and causes the distal end surface of the distal end portion 262 to face the orifice portion of the biliary tract. Next, the operator inserts the front-view high-frequency knife 220A in which the operation portion main body 281 and the slider 272 are in the initial state into the biliary tract 110, while observing the endoscopic image displayed on the screen of the display apparatus. After that, the operator sends air into the balloon 232 through an air-sending tube, not shown, to retain the inflated balloon 232 in the biliary tract 110 as shown in FIG. 49A.

Next, the operator moves the operation portion main body 281 toward the slider 272 in order to perform EST. Then, the outer-layer sheath 222 moves backward in conjunction with the movement of the operation portion main body 281. Then, as shown in FIG. 49B, for example, the fixing ring 271 and the first insulating tube 280 are arranged in the biliary tract 110, while the second insulating tube 279 is arranged in the vicinity of the orifice portion of the biliary tract 110, thereby forming the knife portion 228 in an expanded shape in front of the distal end surface of the outer-layer sheath 222.

The operator can perform EST by supplying high-frequency current from the high-frequency power supply apparatus to the operation wire 223. At this time, since the inflated balloon 232 is retained in the biliary tract 110, the position of the knife portion 228 does not change with respect to the balloon 232, thereby capable of performing stable dissection.

Note that, after the EST is finished, the operator performs manual operation for housing the knife portion 228 in the outer-layer sheath 222, and thereafter deflates the balloon 232 once, similarly as in the above-described embodiment. After that, the operator inserts the front-view high-frequency knife 220A into the deep part of the biliary tract 110. After the insertion to the deep part is finished, the operator retains the balloon 232 at the deep part of the biliary tract, and pushes the insertion portion 261 of the front-view endoscope 260 into the deep part of the biliary tract by using the balloon sheath 231 as a guide.

The front-view high-frequency knife 220A including the high-frequency dissection portion 221A and the balloon catheter portion 230A is thus configured. According to such a configuration, the knife portion 228 is housed in the outer-layer sheath 222 in a linear state without being folded.

In addition, the fixing ring 271 is provided, thereby capable of setting the positional relationship between the distal end side of the knife portion 228 and the proximal end side of the balloon 232 is set to a certain interval. As a result, it is possible to perform stable dissection. Other workings and the effects are the same as those in the embodiment shown in FIGS. 42 to 45D.

Incidentally, when widening the duodenal papilla and the orifice portion of the biliary tract by dissection, it is necessary to dissect the duodenal papilla in the direction in which the biliary tract extends. In addition, in order to reduce bleeding at the time of dissection, the dissection direction and the dissection length have to be set appropriately. The appropriate dissection direction and the dissection length are generally determined depending on the anatomical biliary tract direction and the positions of blood vessels around the biliary tract.

Specifically, if it is supposed that the duodenal orifice side is the twelve o'clock direction and the anus side is the six o'clock direction when the duodenal papilla is seen from the front, the dissection direction is between the 11 o'clock direction and the 12 o'clock direction with the orifice of the duodenal papilla set as a center.

In conventional high-frequency knives, it has been necessary to adjust a direction and length of dissection by slightly operating the endoscope during the input of the high-frequency current, that is, during the dissection. Therefore, there has been a problem that the procedure for dissecting the duodenal papilla and the orifice portion of the biliary tract requires a skill.

Therefore, there is a desire for a front-view high-frequency knife which enables easy setting of dissection direction which is difficult for a less-experienced operator.

Figure 50:
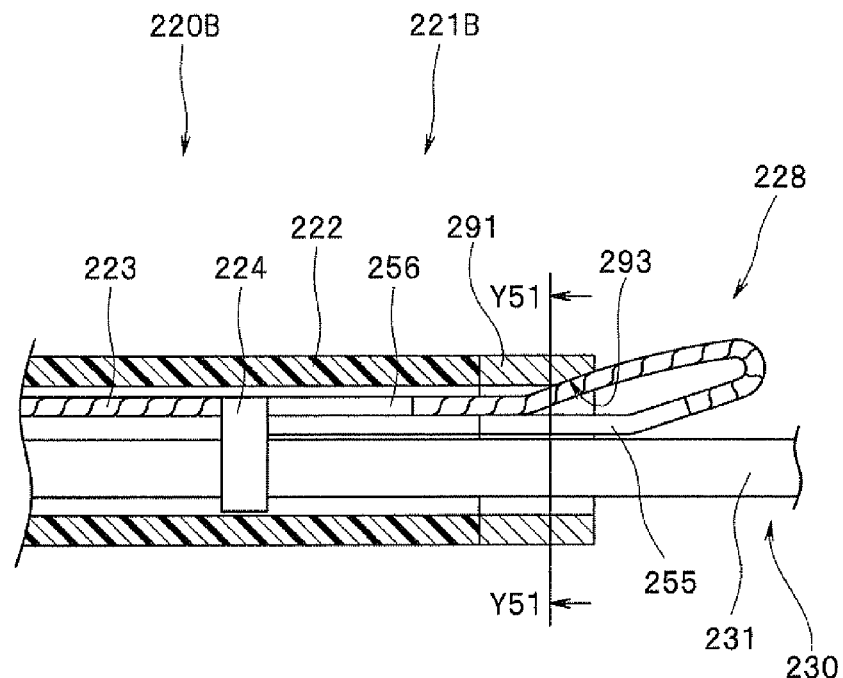
Figure 51:
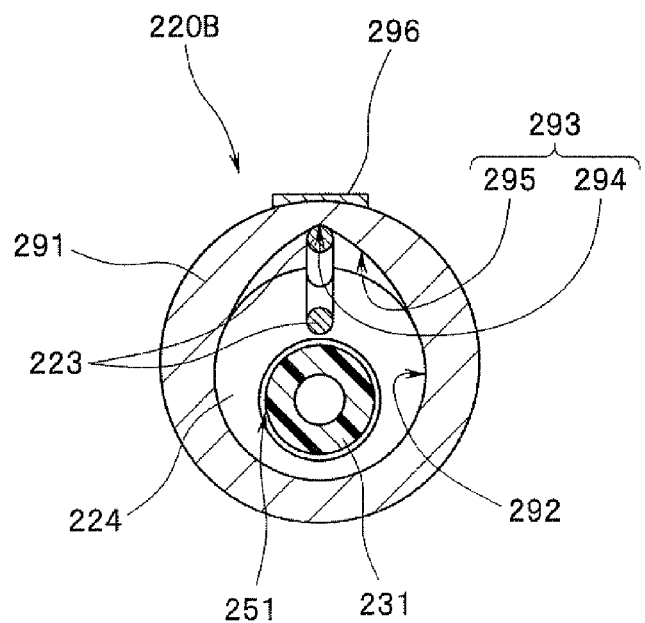
Figure 52A:
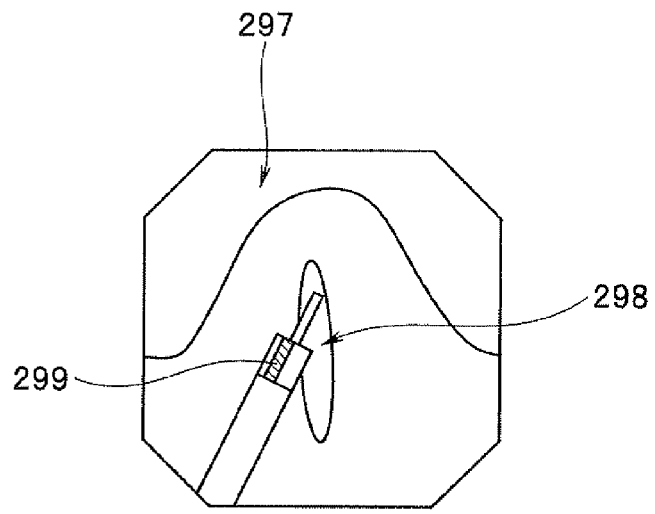
Figure 52B:
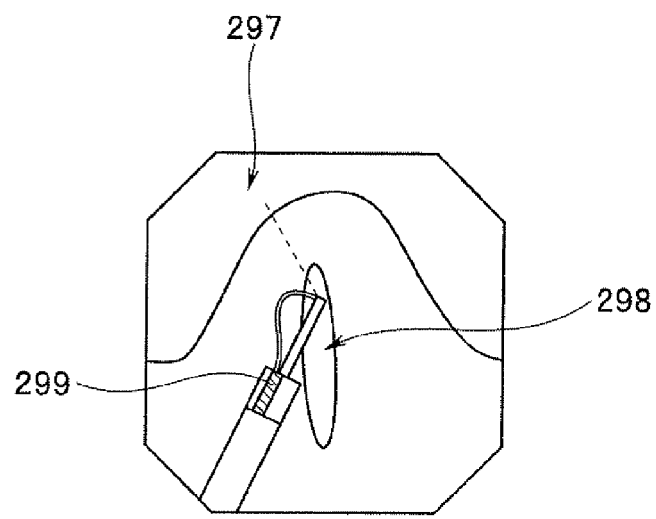

FIG. 50 to FIG. 52B relate to views illustrating exemplary configurations and workings of a front-view high-frequency knife which is capable of easily setting a dissection section. FIG. 50 is a view illustrating a front-view high-frequency knife having a rotation direction restricting member at a distal end of the outer-layer sheath. FIG. 51 is a cross-sectional view taken along the Y51-Y51 line shown by the arrows in FIG. 50. FIG. 52A and FIG. 52B relate to views illustrating workings of the high-frequency knife for front-view endoscope in which: FIG. 52A is a view illustrating a best positional relationship between the orifice portion of the biliary tract and the marker which are displayed on a screen of a display apparatus; and FIG. 52B is a view illustrating the orifice portion of the biliary tract and the knife portion protruded in a desired direction which are displayed on the screen of the display apparatus.

A front-view high-frequency knife 220B as shown in FIG. 50 includes a high-frequency dissection portion 221B and a balloon catheter portion 230. The high-frequency dissection portion 221B is configured by including the outer-layer sheath 222, a rotation direction restricting member 291, the operation wire 223, the sliding ring 224, and a slider not shown. Note that the reference numeral 231 represents the balloon sheath 231 which configures the balloon catheter portion 230.

As shown in FIGS. 50 and 51, the rotation direction restricting member 291 is a ring-shaped member and includes a knife position restricting recessed portion 293 in an inner hole 292. The knife position restricting recessed portion 293 is configured by including a recessed summit portion 294 and a guiding surface 295. As shown in FIG. 50, in the rotation direction restricting member 291, the thickness of the region where the knife position restricting recessed portion 293 is formed is set to be gradually thinner from the proximal end side toward the distal end side.

The recessed summit portion 294 is provided at the position corresponding to the twelve o'clock position in the drawing. The guiding surface 295 is an inclined surface formed both sides of the recessed summit portion 294. According to such a configuration, due to the elastic force generated from the operation wire 223 when the operation wire 223 is deformed in conjunction with the movement of the slider, the operation wire 223 is caused to move on the guiding surface 295, to be placed in the recessed summit portion 294.

The reference numeral 296 represents a marker. The marker 296 is provided on the outer surface of the rotation direction restricting member 291. The marker 296 indicates the position of the knife position restricting recessed portion 293.

According to the front-view high-frequency knife 220B configured as described above, when performing the procedure for widening the duodenal papilla and the orifice portion of the biliary tract by dissection, a biliary tract orifice portion image 298 is displayed on the screen 297 of the display apparatus as shown in FIG. 52A, and a marker image 299 is displayed with respect to the biliary tract orifice portion image 298 as shown in the drawing. After that, the operator moves the slider to allow the knife portion 228 to protrude. According to this operation, the dissection direction of the knife portion in an expanded shape is a desired dissection direction as shown by the dashed line, as shown in FIG. 52B.

The rotation direction restricting member 291 having the knife position restricting recessed portion 293 is provided at the distal end portion of the outer-layer sheath 222, and the marker 296 for indicating the position of the knife position restricting recessed portion 293 is provided on the outer surface of the rotation direction restricting member 291. Then, the marker image 299 is arranged so as to be located at a predetermined position with respect to the biliary tract orifice portion image 298 displayed on the screen 297. As a result, it is possible to easily perform setting of the dissection direction which has been difficult for a less-experienced operator.

Figure 53:
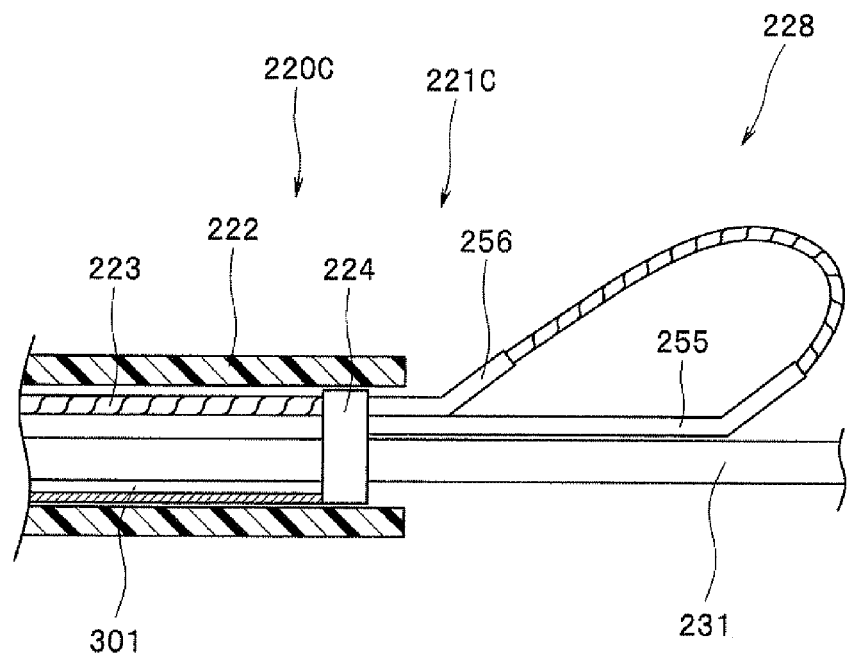
FIG. 53 is a view illustrating another configuration of the high-frequency knife for front-view endoscope which is capable of easily setting the dissection direction.
Figure 54:
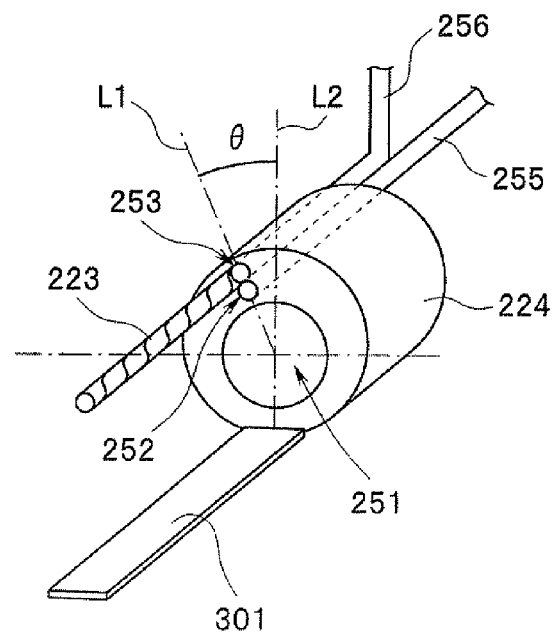
FIG. 54 is a view illustrating an arranging relationship between a sliding ring and a thin-plate member.

Note that the configuration of the front-view high-frequency knife capable of easily performing the setting of the dissection direction is not limited to the configuration in which the rotation direction restricting member 291 is disposed at the distal end of the outer-layer sheath 222, and may be the configurations of the front-view high-frequency knife shown in FIG. 53 and FIG. 54.

A front-view high-frequency knife 220C shown in FIG. 53 includes a high-frequency dissection portion 221C and a balloon catheter portion 230. The high-frequency dissection portion 221C is configured by including the outer-layer sheath 222, the operation wire 223, the sliding ring 224, a thin-plate member 301, and a slider not shown. Note that the reference numeral 231 represents the balloon sheath 231.

As shown in FIG. 54, the thin-plate member 301 has a predetermined elasticity and is fixed to the sliding ring 224. The fixing position of the thin-plate member 301 with respect to the sliding ring 224 is set to a predetermined position. The present embodiment sets a virtual line L1 passing through the center of the balloon sheath insertion hole 251, the center of the first operation wire fixing hole 252 and the center of the second operation wire fixing hole 253 so as to intersect with the normal line L2 of the thin-plate member 301 at a predetermined angle θ. Note that the angle θ is within a range between 15 degrees to 30 degrees.

According to this configuration, when the front-view high-frequency knife 220C including the sliding ring 224 to which the thin-plate member 301 is fixed passes through the bending portion which is bent in the up direction, for example, the thin-plate member 301 is rotated such that the normal line direction of the member 301 coincides with the up direction. This makes the up/down positional relationship of the insertion portion coincide with the up/down positional direction of the front-view high-frequency knife 220C.

Therefore, the knife portion 228 protruded from the outer-layer sheath 222 in the above-described state is protruded inclined by a predetermined amount.

According to the front-view high-frequency knife 220C having the thin-plate member 301 fixed to the sliding ring 224 in a predetermined positional relationship, it is possible to easily perform setting of the dissection direction which is difficult for a less-experienced operator by allowing the high-frequency knife to pass through the bending portion in a bent state.

Incidentally, in the knife portion 228 configured as described above, the shape of the knife portion 228 is set depending on the lengths of the insulation tubes, and the shapes of the folded parts provided to the insulating tubes. In other words, by allowing the insulating tubes housed in the outer-layer sheath 222 to expose outside the outer-layer sheath 222, the operation wire 223 is deformed and the knife portion 228 having a predetermined shape is formed.

Therefore, there is a desire for a front-view high-frequency knife capable of changing the shape of the knife portion 228 in accordance with the shape of the papilla and the like.

Figure 55:
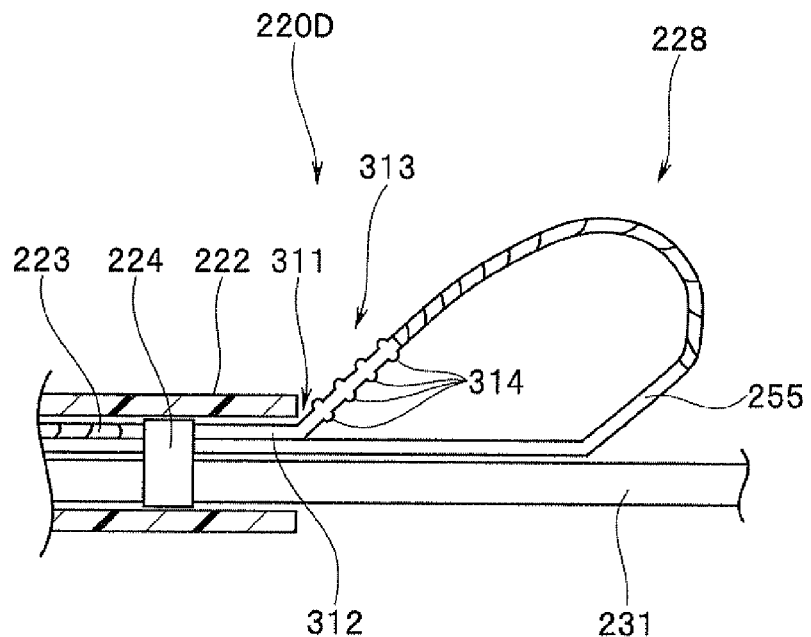
FIG. 55 is a view illustrating the high-frequency knife for front-view endoscope which has a positioning portion on a second insulating tube.

A front-view high-frequency knife 220D shown in FIG. 55 is provided with a positioning portion 313 on the more distal end side than a folded part 311 of the second insulating tube 312 having the folded part 311. The positioning portion 313 is configured by a plurality of projection portions which are regularly aligned, for example.

Figure 56:
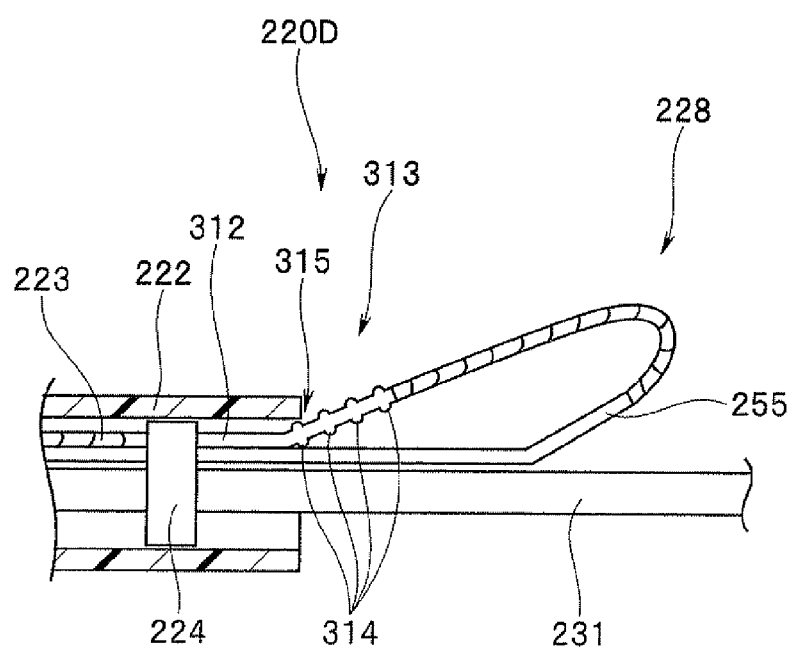
FIG. 56 is a view illustrating the working of the positioning portion provided on the second insulating tube.

According to such a configuration, the angle of the knife portion 228 can be adjusted by allowing the distal end of the outer-layer sheath 222 to get caught in a groove 315 between a pair of projection portions 314, as shown in FIG. 56.

Thus, by appropriately changing the position of the groove 315 by which the distal end of the outer-layer sheath 222 is get caught, a knife portion optimal for the shape of the papilla is obtained, thereby capable of performing a stable dissection procedure.

Note that, a saw-edged projection and recess may be provided to the operation wire 223 instead of providing the positioning portion 313 to the second insulating tube 312.

The present invention is not limited to the above embodiments but various modifications thereof are possible without departing from the gist of the invention.

What is claimed is:

1. A two-part bending endoscope comprising:
   an insertion portion;
   a bending portion arranged on the insertion portion, the bending portion including a first bending part and a second bending part, wherein
   the first bending part is arranged on one side of the bending portion, and
   the seconds bending part is arranged on an other end side of the bending portion and linked with the first bending part;
   an operation portion; and
   a bending portion operation apparatus which is provided on the operation portion so as to be linked with a proximal end of the insertion portion, the bending portion operation apparatus including a first operation device for causing the first bending part to perform a bending action and a second operation device for causing the second bending part to perform a bending action, wherein:
   the bending portion operation apparatus includes a selective power-transmitting mechanism section which enables at least a bending action of the first bending part by the first operation device, and an interlocking operation of the second bending part and the first bending part by the second operation device;
   the selective power-transmitting mechanism section is an independent rotation/co-rotation mechanism section; and
   the independent rotation/co-rotation mechanism section includes:
   a shaft arranged on the first operation device;
   a first rotation body whose cross-sectional shape is a regular polygon, the first rotation body being integrally fixed to the shaft;
   a ring-shaped member arranged on the second operation device;
   a second rotation body which is integrally fixed to the ring-shaped member, the second rotation body including a first rotation body arranging recessed portion in which the first rotation body is rotatably arranged and whose cross-sectional shape is a regular polygon, and a hole through which the shaft passes;
   a plurality of stepped pillar members, each including: a globe portion which has a predetermined diameter and which is arranged in a gap formed by an inner surface of the first rotation body arranging recessed portion and an outer surface of the first rotation body; a small-diameter portion to which the globe portion is integrally fixed; and a large-diameter portion as a sliding portion; and
   a rotational force transmission switching section including a through hole through which the shaft passes, long holes in which the respective small-diameter portions of the stepped pillar members are slidable, the long holes being formed in an elongated shape in a central axis direction of the through hole, and a case body having a space portion in which the respective large-diameter portions of the stepped pillar members are slidably arranged.

2. The two-part bending endoscope according to claim 1, comprising:
   a first bending part pulling wire to be operated to bend the first bending part by being pulled;
   a second bending part pulling wire to be operated to bend the second bending part by being pulled;
   the first operation device provided so as to be linked with the proximal end of the insertion portion and configured to cause the first bending part to perform a bending action by pulling the first bending part pulling wire;
   the second operation device configured to cause the first bending part and the second bending part to perform a bending action at the same time by pulling both of the first bending part pulling wire and the second bending part pulling wire at the same time; and
   the independent rotation/co-rotation mechanism section which is configured to be able to transmit a bending operation of the first operation device only to the first bending part pulling wire when the first operation device is operated, and transmit a bending operation of the second operation device to both of the first bending part pulling wire and the second bending part pulling wire when the second operation device is operated.

3. The two-part bending endoscope according to claim 1, wherein the selective power-transmitting mechanism section further includes a second operation device action switching section,
   wherein the second operation device action switching section includes:

an engaging portion formed at a predetermined position on an outer circumferential surface of the shaft of the first operation device, a lever portion protruded from the ring-shaped member of the second operation device, and a member to be engaged which is configured to be engaged with the engaging portion and slidable with respect to the lever portion.

4. The two-part bending endoscope according to claim 3, wherein when the member to be engaged is arranged in the engaging portion, the second operation device action switching section transmits a driving force generated in conjunction with the bending operation of the second operation device to the second bending part and also to the first bending part, and when the member to be engaged is arranged outside the engaging portion, the second operation device action switching section transmits the driving force generated in conjunction with the bending operation of the second operation device to the second bending part.

5. The two-part bending endoscope according to claim 1, wherein when the first bending part is arranged on a distal end side of the bending portion, and the second bending part is arranged on a proximal end side of the bending portion, the first bending part has a phase difference with respect to the second bending part in a counterclockwise direction in a circumferential direction, when the bending portion is viewed from the operation portion side.

6. The two-part bending endoscope according to claim 5, wherein the phase difference is within a range between 5 degrees to 45 degrees.

7. The two-part bending endoscope according to claim 1, wherein the first bending part bends in at least two or more directions, and the second bending part bends in at least one or more directions.

8. The two-part bending endoscope according to claim 1, wherein rotation of the ring-shaped member is transmitted to the second bending part pulling wire through a linear motion link mechanism.

* * * * *

UNITED STATES PATENT AND TRADEMARK OFFICE
CERTIFICATE OF CORRECTION

| | |
|---|---|
| PATENT NO. | : 8,652,030 B2 |
| APPLICATION NO. | : 13/286906 |
| DATED | : February 18, 2014 |
| INVENTOR(S) | : Wataru Matsuura et al. |

It is certified that error appears in the above-identified patent and that said Letters Patent is hereby corrected as shown below:

In the Claims

Column 35, line 52 (Claim 1, line 8) should read,

"the second bending part is arranged on an other end side of the bending portion and linked with the first bending part;"

Signed and Sealed this
Twenty-seventh Day of May, 2014

Michelle K. Lee
*Deputy Director of the United States Patent and Trademark Office*